(12) United States Patent
Desai

(10) Patent No.: US 10,265,313 B2
(45) Date of Patent: Apr. 23, 2019

(54) PLASMODIAL SURFACE ANION CHANNEL INHIBITORS FOR THE TREATMENT OR PREVENTION OF MALARIA

(71) Applicant: The United States of America, as represented by the Secretary, Department of Health and Human Services, Washington, DC (US)

(72) Inventor: Sanjay A. Desai, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/723,677

(22) Filed: Oct. 3, 2017

(65) Prior Publication Data

US 2018/0015086 A1    Jan. 18, 2018

Related U.S. Application Data

(62) Division of application No. 15/072,902, filed on Mar. 17, 2016, now Pat. No. 9,808,458, which is a division
(Continued)

(51) Int. Cl.
| | |
|---|---|
| *A61K 31/4985* | (2006.01) |
| *A61K 31/501* | (2006.01) |
| *A61K 31/496* | (2006.01) |
| *C07D 413/14* | (2006.01) |
| *C07D 409/04* | (2006.01) |
| *C07D 409/14* | (2006.01) |
| *C07D 239/84* | (2006.01) |
| *C07D 417/06* | (2006.01) |
| *C07D 241/44* | (2006.01) |
| *C07D 263/57* | (2006.01) |
| *C07D 491/048* | (2006.01) |
| *C07D 498/04* | (2006.01) |
| *C07D 277/54* | (2006.01) |
| *C07D 513/04* | (2006.01) |

(Continued)

(52) U.S. Cl.
CPC ............ *A61K 31/501* (2013.01); *A61K 31/42* (2013.01); *A61K 31/422* (2013.01); *A61K 31/423* (2013.01); *A61K 31/427* (2013.01); *A61K 31/433* (2013.01); *A61K 31/437* (2013.01); *A61K 31/4355* (2013.01); *A61K 31/4439* (2013.01); *A61K 31/4741* (2013.01); *A61K 31/495* (2013.01); *A61K 31/496* (2013.01); *A61K 31/498* (2013.01); *A61K 31/50* (2013.01); *A61K 31/517* (2013.01); *A61K 31/519* (2013.01); *A61K 31/554* (2013.01); *A61K 39/015* (2013.01); *A61K 45/06* (2013.01); *C07D 239/84* (2013.01); *C07D 241/44* (2013.01); *C07D 263/57* (2013.01); *C07D 277/54* (2013.01); *C07D 281/16* (2013.01); *C07D 409/04* (2013.01); *C07D 409/14* (2013.01); *C07D 413/14* (2013.01); *C07D 417/06* (2013.01); *C07D 491/048* (2013.01); *C07D 498/04* (2013.01); *C07D 513/04* (2013.01); *C07K 14/445* (2013.01); *C07K 16/205* (2013.01); *C07K 2319/21* (2013.01); *C07K 2319/43* (2013.01); *Y02A 50/411* (2018.01)

(58) Field of Classification Search
CPC .......................... A61K 31/522; A61K 31/4985
See application file for complete search history.

(56) References Cited

U.S. PATENT DOCUMENTS

| | | |
|---|---|---|
| 2,895,956 A | 7/1959 | Tuppy |
| 6,602,865 B1 | 8/2003 | Andrasi et al. |

(Continued)

FOREIGN PATENT DOCUMENTS

| | | |
|---|---|---|
| WO | WO 00/27851 A1 | 5/2000 |
| WO | WO 2007/008541 A2 | 1/2007 |

(Continued)

OTHER PUBLICATIONS

Whitelaw, Can Malaria be Prevented, retrieved from https://www.health24.com/Medical/Malaria/Overview/Can-malaria-be-prevented-20130205 on Jul. 6, 2018, p. 1-2. (Year: 2018).*
(Continued)

*Primary Examiner* — Rebecca L Anderson
*Assistant Examiner* — Karen Cheng
(74) *Attorney, Agent, or Firm* — Leydig, Voit & Mayer, Ltd.

(57) ABSTRACT

The invention provides methods of treating or preventing malaria comprising administering to an animal an effective amount of a compound of formula I:

$$Q-Y-R^1-R^2 \qquad (I),$$

wherein Q, Y, $R^1$, and $R^2$ are as described herein. Methods of inhibiting a plasmodial surface anion channel of a parasite in an animal are also provided. The invention also provides pharmaceutical compositions comprising a compound represented by formula I in combination with any one or more compounds represented by formulas II, V, and VI. Use of the pharmaceutical compositions for treating or preventing malaria or for inhibiting a plasmodial surface anion channel in animals including humans are also provided. Also provided by the invention are clag3 amino acid sequences and related nucleic acids, vectors, host cells, populations of cells, antibodies, and pharmaceutical compositions.

13 Claims, 5 Drawing Sheets
Specification includes a Sequence Listing.

Related U.S. Application Data of application No. 14/111,256, filed as application No. PCT/US2012/033072 on Apr. 11, 2012, now Pat. No. 9,320,786.

(60) Provisional application No. 61/474,583, filed on Apr. 12, 2011.

(51) Int. Cl.

| | |
|---|---|
| *C07D 281/16* | (2006.01) |
| *A61K 31/42* | (2006.01) |
| *A61K 31/433* | (2006.01) |
| *A61K 31/495* | (2006.01) |
| *A61K 31/498* | (2006.01) |
| *A61K 31/50* | (2006.01) |
| *A61K 31/519* | (2006.01) |
| *A61K 31/554* | (2006.01) |
| *C07K 14/445* | (2006.01) |
| *A61K 31/422* | (2006.01) |
| *A61K 31/4741* | (2006.01) |
| *A61K 31/517* | (2006.01) |
| *A61K 39/015* | (2006.01) |
| *C07K 16/20* | (2006.01) |
| *A61K 45/06* | (2006.01) |
| *A61K 31/423* | (2006.01) |
| *A61K 31/427* | (2006.01) |
| *A61K 31/4355* | (2006.01) |
| *A61K 31/437* | (2006.01) |
| *A61K 31/4439* | (2006.01) |

(56) References Cited

U.S. PATENT DOCUMENTS

| | | |
|---|---|---|
| 2006/0135447 A1 | 6/2006 | Chupak et al. |
| 2011/0144107 A1 | 6/2011 | Chatterjee et al. |

FOREIGN PATENT DOCUMENTS

| | | |
|---|---|---|
| WO | WO 2009/137081 A2 | 11/2009 |
| WO | WO 2009/152356 A2 | 12/2009 |
| WO | WO 2010/011537 A1 | 1/2010 |

OTHER PUBLICATIONS

National Institute of Allergy and Infectious Diseases, Malaria Prevention, Treatment and Control Strategies, retrieved from https://www.niaid.nih.gov/diseases-conditions/malaria-strategies on Jul. 6, 2018, p. 1-2. (Year: 2011).*
U.S. Appl. No. 15/072,902, filed Mar. 17, 2016.
U.S. Appl. No. 14/111,256, filed Nov. 7, 2013.
Alkhalil et al., "Plasmodium falciparum likely encodes the principal anion channel on infected human erythrocytes," *Blood*, 104, 4279-86 (2004).
Asahi et al, "Hypoxanthine: a low molecular weight factor essential for growth of erythrocytic plasmodium falciparum in a serum-free medium," *Parasitology*, 113, 19-23 (1996).
Balu et al., "High-efficiency transformation of plasmodium falciparum by the lepidopteran transposable element piggyback," *PNAS*, 102 (45), 16391-96 (2005).
Balu et al., "PiggyBac is an effective tool for functional analysis of the plasmodium falciparum genome," *BMC Microbiology*, 9, 83 (2009).
Baumeister et al., "Evidence for the involvement of plasmodium falciparum proteins in the formation of new permeability pathways in the erythrocyte membrane," *Mol. Microbiol.*, 60(2), 493-504 (2006).
Bokhari et al., "Two distinct mechanisms of transport through the plasmodial surface anion channel," *J. Membr. Biol.*, 226, 27-34 (2008).
Broman et al., "QTL mapping in experimental crosses," *Bioinformatics*, 19, 889-890 (2003).
Chen et al, "Developmental selection of var gene expression in plasmodium falciparum," *Nature*, 394, 392-95 (1998).
Cortes et al, "Epigenetic silencing of plasmodium falciparum genes linked to erythrocyte invasion," *PLoS Pathog.*, 3, e107 (2007).
"Cytoadherence linked asexual protein 3.1, [Plasmodium falciparum 3D7]," GenBank XP_001351099(124504713) (2010).
"Cytoadherence linked asexual protein 3.1, [Plasmodium falciparum 3D7]," GenBank XP_001351100(CAB10572.2) (2010).
Desai et al., "A nutrient-permeable channel on the intraerythrocytic malaria parasite," *Nature*, 362, 643-646 (1993).
Desai et al., "Open and closed states of the plasmodial surface anion channel," *Nanomedicine*, 1(1), 58-66 (2005).
Desai et al., "Pore size of the malaria parasite's nutrient channel," PNAS, 94(5), 2045-2049 (1997).
Desai et al., "A voltage-dependent channel involved in nutritent uptake by red blood cells infected with the malaria parasite," *Nature*, 406, 1001-05 (2000).
Dickerman et al., "Identification of inhibitors that dually target the new permeability pathway and dihydroorotate dehydrogenase in the blood stage of *Plasmodium falciparum*," *Scientific Reports*, 6: 37502 (pp. 1-15) (2016).
European Patent Office, Supplementary Search Report in European Patent Application No. 12770599.4 (dated Jul. 22, 2014).
Fidock et al., "Transformation with human dihydrofolate reductase renders malaria parasites insensitive to WR99210 but does not affect the intrinsic activity of proguanil," *PNAS*, 94, 10931-36 (1997).
Freitas-Junior et al., "Frequent ectopic recombination of virulence factor genes in telomeric chromosome clusters of *P. falciparum*," Nature, 407, 1018-22 (2000).
Fujiki et al., "Isolation of intracellular membranes by means of sodium carbonate treatment: application to endoplasmic reticulum," *J. Cell Biol.*, 93, 97-102 (1982).
Gemma et al., "Malaria Chemotherapy: Recent Advances in Drug Development," *Recent Patents on Anti-Infective Drug Discovery*, 5, 195-225 (2010).
Gero et al., "New nucleoside transport pathways induced in the host erythrocyte membrane of malaria and babesia infected cells," *Adv. Exp. Med. Biol.*, 309A, 169-172 (1991).
Ginsburg et al., "Characterization of permeation pathways appearing in the host membrane of plasmodium falciparum infected red blood cells," *Mol. Biochem. Parasitol.*, 14, 313-22 (1985).
Howitt et al., "Clonally variant gene families in plasmodium falciparum share a common activation factor," *Mol. Microbiol.*, 73, 1171-85 (2009).
International Search Report, International Application No. PCT/US 12/33072, dated Oct. 16, 2012.
Kall et al., "An HMM posterior decoder for sequence feature prediction that includes homology information," *Bioinformatics*, 21, i251-51 (2005).
Kaneko et al., "Apical expression of three RhopH1/Clag proteins as components of the plasmodium falciparum RhopH complex," *Mol. Biochem. Parasitol.*, 143(1), 20-8 (2005).
Kang et al., "Malaria parasites are rapidly killed by dantrolene derivatives specific for the plasmodial surface anion channel," *Mol. Pharmacol*, 68, 34-40 (2005).
Kelly et al., "Selective killing of the human malaria parasite plasmodium falciparum by a benzylthiazolium dye," *Exp. Parasitol.* 116(2), 103-110 (2007).
Kilejian et al., "Selective association of a fragment of the knob protein with spectrin, actin and the red cell membrane," *Mol. Biochem. Parasitol.*, 44(2), 175-81 (1991).
Krogh et al., "Predicting transmembrane protein topology with a hidden Markov model: application to complete genomes,"*J. Mol. Biol.*, 305, 567-80 (2001).
Krungkrai et al., "Malaria parasite carbonic anhydrase: inhibition of aromatic/heterocyclic sulfonamides and its therapeutic potential," *Asian Pacific Journal of Tropical Biomedicine*, 233-242 (2011).

(56) References Cited

OTHER PUBLICATIONS

Kumar et al., "Discovery of a Rhodanine Class of Compounds as Inhibitors of *Plasmodium falciparum* Enoyl-Acyl Carrier Protein Reductase" *J Med. Chem.* 50, 2665-2675 (2007) with supporting information, pp. 1-14.

Lambros et al, "Synchronization of plasmodium falciparum erythrocytic stages in culture," *J. Parasitol.*, 65(3), 418-20 (1979).

Lavazec et al., "Expression switching in the stevor and Pfmc-2TM superfamilies in Plasmodium falciparum," *Mol. Microbiol.*, 64(6), 1621-34 (2007).

Lisk et al., "The plasmodial surface anion channel is functionally conserved in divergent malaria parasites," Eukaryotic Cell, 4, 2153-2159 (2005).

Lisk et al., "Changes in the plasmodial surface anion channel reduce leupeptin uptake and can confer drug resistance in plasmodium falciparum-infected erythrocytes," *Antimicrob. Agents Chemother.*, 52, 2346-54 (2008).

Liu et al., "Functional profiling, identification, and inhibition of plasmepsins in intraerythrocytic malaria parasites," *Angew. Chem. Int. Ed.*, 48, 8293-8297 (2009).

Marshall et al, "A critical assessment of the use of microculture tetrazolium assays to measure cell growth and function," *Growth Regul.*, 5(2), 69-84 (1995).

Marti et al., "Targeting malaria virulence and remodeling proteins to the host erythrocyte," *Science*, 306, 1930-33 (2004).

Matsuhisa et al, "Binary solute adsorption of dosed drugs on serum albumin," *Chem. Engineering J.*, 34, B21-B27 (1987).

Nguitragool et al., "Malaria parasite clag3 genes determine channel-mediated nutrient uptake by infected red blood cells," *Cell*, 145, 665-677 (2011).

Olepu et al., "2-Oxo-tetrahydro-1,8-naphthyridines as selective inhibitors of malarial protein farnesyltransferase and as antimalarials," *Bioorg. Med. Chem. Lett.*, 18, 494-497 (2008).

Pillai et al, "A cell-based high-throughput screen validates the plasmodial surface anion channel as an antimalarial target," *Mol. Pharmacol.*, 77, 724-33 (2010).

Pillai et al., "Solute restriction reveals an essential role for clag3-associated channels in malaria parasite nutrient acquisition," *Mol. Pharmacol.*, 82(6), 1104-14 (2012).

"Plasmodium falciparum 3D7 Cytoadherence linked asexual protein 3.1 (RhopH1(3.1)) mRNA, complete cds," GenBank XM_001351063(124504712) (2010).

"Plasmodium falciparum 3D7 Cytoadherence linked asexual protein 3.1 (RhopH1(3.1)) mRNA, complete cds," GenBank XM_001351064(124504714) (2010).

Price et al., "FastTree: computing large minimum evolution trees with profiles instead of distance matrix," *Mol. Biol. Evol.*, 26, 1641-50 (2009).

Saliba et al., "Transport and metabolism of the essential vitamin pantothenic acid in human erythrocytes infected with the malaria parasite plasmodium falciparum," *J. Biol. Chem.*, 273 (17), 10190-95 (1998).

Sato et al., "Media for culture of mammalian cells," *Curr. Protoc. Cell Biol.*, 1, Unit 1.2 (2001).

Sherf et al, "Antigenic variation in plasmodium falciparum," *Annu. Rev. Microbiol.*, 62, 445-470 (2008).

Sigworth et al., "Data transformations for improved display and fitting of single-channel dwell time histograms," *Biophys. J.*, 52, 1047-54 (1987).

Spielmann et al., "Protein export in malaria parasites: do multiple export motifs add up to multiple export pathways?" *Trends Parasitol.*, 26(1), 6-10 (2010).

Su et al., "A genetic map and recombination parameters of the human malaria parasite plasmodium falciparum," *Science*, 286, 1351-53 (1999).

Vinsensini et al., "The RhopH complex is transferred to the host cells cytoplasm following red blood cell invasion by plasmodium falciparum," *Mol. Biochem. Parrasitol.*, 160, 81-89 (2008).

Wagner et al., "A two-compartment model of osmotic lysis in plasmodium faciparum-infected erythrocytes," *Biophysical J.*, 84, 116-23 (2003).

Wellems et al., "Chloroquine resistance not linked to mdr-like genes in a plasmodium falciparum cross," *Nature*, 345, 253-55 (1990).

Written Opinion, International Application No. PCT/US 12/33072, dated Oct. 16, 2012.

Bokhari et al., "High Guanidinium Permeability Reveals Dehydration-Dependent Ion Selectivity in the Plasmodial Surface Anion Channel" *BioMed Research International* pp. 1-8 (2014).

Ito et al., "An essential dual-function complex mediates erythrocyte invasion and channel-mediated nutrient uptake in malaria parasites" *eLife*, pp. 1-24, published Feb. 21, 2017.

\* cited by examiner

SEQUENCE LISTING

```
<160> NUMBER OF SEQ ID NOS: 79

<210> SEQ ID NO 1
<211> LENGTH: 4254
<212> TYPE: DNA
<213> ORGANISM: Plasmodium falciparum

<400> SEQUENCE: 1
atggtttcat tttttaaaac tccaatcttt attttaatta tcttttttata cttaaatgaa      60 aaggtaatat gttcaataaa tgaaaatcaa aatgaaaatg ataccattag tcaaaatgtc     120
aaccaacatg aaaatattaa tcaaaatgta aatgataatg acaatattga acaattaaaa     180
tccatgattg gaaatgatga actacataag aatttaacaa tattagaaaa attaatttta     240
gagtctttag aaaaagataa attaaaatat cctctcctta aacaaggaac tgaacaattg     300
atagatatat caaaatttaa taaaaaaaat attacagatg cggatgatga aacgtacatc     360
atacccaccg tccaatcaac gtttcacgat attgtgaaat acgaacatct tataaaagaa     420
caatcaatag aaatttacaa ttctgatata tcagataaaa ttaagaaaaa aattttata      480 gtaagaacat tgaaaaccat aaaattaatg cttataccat taaactcgta caaacaaaat     540
aatgacttga atctgcact cgaagaatta aataatgtat ttacaaacaa agaagctcaa      600
gaggaaagca gtccaatagg cgaccatggg acattcttta gaaaattgtt aacacatgtt     660
agaacaatta aagaaaatga agatatagaa aataaaggag aaacacttat attaggcgat     720
aataaaatag atgtaatgaa ttcaaacgat ttcttttta caaccaactc aaatgtaaaa     780
tttatggaaa atttagatga tataacaaat caatatggat taggtttgat taatcatcta     840
ggtcctcatt taatagcctt gggtcatttt accgtattaa aattagcact aaaaaattac     900
aaaaactatt ttgaagcaaa aagtattaaa tttttttagtt ggcaaaaaat tttagagttc     960
tccatgtctg atagatttaa agttcttgat atgatgtgtg accatgaatc tgtatactat    1020
tccgaaaaaa aacgtagaaa aacatattta aaagttgaca gatcaaatac atctatggaa    1080
tgtaatatat tggaatattt attacattat tttaataaat accaactaga aataattaaa    1140
actacacaag atactgattt tgacttacat ggtatgatgg aacataaata tataaaagat    1200
tatttctttt catttatgtg taatgatcct aaagaatgta ttatttatca tacgaatcaa    1260
tttaaaaaag aagccaacga agaaaacaca tttcctgaac aagaagaacc taaccgtcaa    1320
ataagtgcat ttaatttata tttaaattat tattatttca tgaaacgtta tagttcatat    1380
ggagtaaaaa agacattata tgttcatttta ttaaatttaa ctggactttt aaattatgat    1440
acaagagcat acgtgacatc actttatta ccaggatatt acaacgctgt cgaaatgtct     1500
tttacggaag aaaaagagtt ttccaaactt tttgaaagct taatacaatg tattgaaaaa    1560
tgccattcag accaagcaag gcaaatatca aaagatagta atttacttaa taatataaca    1620
aaatgtgatt tgtgtaaagg agcctttttta tatgctaata tgaaattcga tgaagttcct    1680
```

-continued

```
tcaatgttgc aaaaatttta cgtatatttta actaaaggtc tcaaaataca aaaagtatca    1740
tcactaatca aaacgctaga tatatatcaa gattacagca attacttatc acatgatatt    1800
aattggtaca cattcctatt tttatttaga cttacaagtt ttaaagaaat tgcaaagaaa    1860
aatgttgctg aagcaatgta tttaaatata aaagatgaag acacattcaa caaaacggta    1920
gtaacaaact attggtaccc atctcctata aaaaaatatt atacattata tgttagaaaa    1980
catataccaa ataatttagt agatgaattg gagaaattaa tgaaaagtgg cactttagaa    2040
aaaatgaaaa aatctctcac cttttagta catgtgaatt cattttaca attagatttt      2100
ttccatcaat taaatgaacc acctcttgga ttacctcgat catatccatt atcgttagtt    2160
ctcgaacata aatttaaaga atggatgaac agttcgccag caggtttcta ttttcaaat     2220
tatcaaaatc catatatcag aaaagatttg catgataaag ttttatcaca aaaatttgaa    2280
ccacctaaaa tgaatcagtg gaacaaagtt ttgaaatcat taattgaatg cgcatatgat    2340
atgtattttg aacagagaca tgttaaaaat ttatataaat atcataacat ttataatata    2400
aataacaaat taatgttaat gcgagattca atcgatttgt ataaaaacaa ttttgacgat    2460
gtgttatttt ttgcggatat atttaatatg agaaaatata tgacagctac accagtatat    2520
aaaaaagtaa aagacagagt gtaccataca ttgcatagta ttacaggaaa ttctgtcaat    2580
ttttataaat atggtattat atatggattt aaagtaaaca aagaaatatt aaaagaagtt    2640
gtcgatgaat tgtattccat ctataatttt aacaccgaca tatttacgga tacttccttt    2700
ttacaaaccg tttatttatt atttagaaga atagaagaaa cctataggac ccaaagaaga    2760
gatgataaaa ttagtgtgaa taacgttttt ttcatgaatg ttgctaataa ttattccaaa    2820
ttaaacaaag aagaaagaga atcgaaata cataattcca tggcatcaag atattatgca     2880
aaaacgatgt tgcagcatt tcaaatgtta ttttcaacaa tgttgagcaa caatgtagat     2940
aatcttgata aagcatatgg attaagtgaa aatatccaag tagcaacaag tacttccgct    3000
tttcttactt ttgcatatgt atataacgga agtataatgg atagtgtgac taacagttta    3060
ttgccaccat atgcgaagaa acctataaca caattaaaat atggaaaaac cttcgttttc    3120
tcaaactatt tcatgctagc atccaaaatg tatgatatgt taaattataa aaatttaagt    3180
cttttatgtg aatatcaggc tgtggcaagt gccaatttct actctgctaa aaaggtaggt   3240
cagtttcttg aagaaaaatt tttacccata actacatatt ttctagtaat gagaattagt    3300
tggacacatg cttttacaac tggacaacat ttgattagcg cttttggttc cccaagttct   3360
actgctaatg gtaaaagtaa tgctagtggt tataaatccc ctgaaagttt tttcttcact    3420
cacggacttg ctgctgaagc atccaaatat ttatttttt attttttcac aaatttatac    3480
cttgatgcct acaaatcttt tcctggagga tttggtcctg caataaaaga acaaactcaa    3540
catgttcaag aacaaaccta cgaacgcaaa ccgtcagttc atagttttaa tagaaatttt    3600
ttcatggaac tcgtaaatgg attcatgtat gccttttgtt ttttgcaat ttctcaaatg     3660
tatgcatatt ttgaaaatat taatttttat attacaagta atttccgttt cttggataga    3720
tattatggtg tattcaataa atattttata aactatgcca taattaaact taaagaaatt    3780
actagtgatc ttttaataaa atatgaacgt gaggcttatt aagtatgaa aaaatatggt    3840
tatttaggtg aagttattgc agctagactt tctccaaaag ataaaattat gaattatgtg    3900
cacgaaacta acgaagatat catgagtaat ttaagaagat atgatatgga aaatgctttc    3960
aaaaacaaaa tgtcaacata tgtagatgat tttgcttttt ttgatgattg cggaaaaaat    4020
gaacaatttt taaatgagag atgtgattat tgtcctgtaa ttgaagaggt cgaagaaaca    4080
```

```
caattattta ctaccactgg tgataaaaac actaataaga ccacggaaat aaaaaaacaa    4140
actagtacat atattgatac tgaaaaaatg aatgaagcgg attctgctga tagcgacgat    4200
gaaaaggatt ctgatactcc tgacgatgaa ttaatgatat cacgatttca ctaa          4254
```

<210> SEQ ID NO 2
<211> LENGTH: 1417
<212> TYPE: PRT
<213> ORGANISM: Plasmodium falciparum

<400> SEQUENCE: 2

```
Met Val Ser Phe Phe Lys Thr Pro Ile Phe Ile Leu Ile Ile Phe Leu
1               5                   10                  15

Tyr Leu Asn Glu Lys Val Ile Cys Ser Ile Asn Glu Asn Gln Asn Glu
            20                  25                  30

Asn Asp Thr Ile Ser Gln Asn Val Asn Gln His Glu Asn Ile Asn Gln
        35                  40                  45

Asn Val Asn Asp Asn Asp Asn Ile Glu Gln Leu Lys Ser Met Ile Gly
    50                  55                  60

Asn Asp Glu Leu His Lys Asn Leu Thr Ile Leu Glu Lys Leu Ile Leu
65                  70                  75                  80

Glu Ser Leu Glu Lys Asp Lys Leu Lys Tyr Pro Leu Leu Lys Gln Gly
                85                  90                  95

Thr Glu Gln Leu Ile Asp Ile Ser Lys Phe Asn Lys Lys Asn Ile Thr
            100                 105                 110

Asp Ala Asp Asp Glu Thr Tyr Ile Ile Pro Thr Val Gln Ser Thr Phe
        115                 120                 125

His Asp Ile Val Lys Tyr Glu His Leu Ile Lys Glu Gln Ser Ile Glu
    130                 135                 140

Ile Tyr Asn Ser Asp Ile Ser Asp Lys Ile Lys Lys Ile Phe Ile
145                 150                 155                 160

Val Arg Thr Leu Lys Thr Ile Lys Leu Met Leu Ile Pro Leu Asn Ser
                165                 170                 175

Tyr Lys Gln Asn Asn Asp Leu Lys Ser Ala Leu Glu Glu Leu Asn Asn
            180                 185                 190

Val Phe Thr Asn Lys Glu Ala Gln Glu Glu Ser Ser Pro Ile Gly Asp
        195                 200                 205

His Gly Thr Phe Phe Arg Lys Leu Leu Thr His Val Arg Thr Ile Lys
    210                 215                 220

Glu Asn Glu Asp Ile Glu Asn Lys Gly Glu Thr Leu Ile Leu Gly Asp
225                 230                 235                 240

Asn Lys Ile Asp Val Met Asn Ser Asn Asp Phe Phe Thr Thr Asn
                245                 250                 255

Ser Asn Val Lys Phe Met Glu Asn Leu Asp Asp Ile Thr Asn Gln Tyr
            260                 265                 270

Gly Leu Gly Leu Ile Asn His Leu Gly Pro His Leu Ile Ala Leu Gly
        275                 280                 285

His Phe Thr Val Leu Lys Leu Ala Leu Lys Asn Tyr Lys Asn Tyr Phe
    290                 295                 300

Glu Ala Lys Ser Ile Lys Phe Phe Ser Trp Gln Lys Ile Leu Glu Phe
305                 310                 315                 320

Ser Met Ser Asp Arg Phe Lys Val Leu Asp Met Met Cys Asp His Glu
                325                 330                 335

Ser Val Tyr Tyr Ser Glu Lys Lys Arg Arg Lys Thr Tyr Leu Lys Val
```

```
            340                 345                 350
Asp Arg Ser Asn Thr Ser Met Glu Cys Asn Ile Leu Glu Tyr Leu Leu
            355                 360                 365
His Tyr Phe Asn Lys Tyr Gln Leu Glu Ile Ile Lys Thr Thr Gln Asp
            370                 375             380
Thr Asp Phe Asp Leu His Gly Met Met Glu His Lys Tyr Ile Lys Asp
385                 390                 395                 400
Tyr Phe Phe Ser Phe Met Cys Asn Asp Pro Lys Glu Cys Ile Ile Tyr
                405                 410                 415
His Thr Asn Gln Phe Lys Lys Glu Ala Asn Glu Asn Thr Phe Pro
            420                 425             430
Glu Gln Glu Glu Pro Asn Arg Gln Ile Ser Ala Phe Asn Leu Tyr Leu
        435                 440                 445
Asn Tyr Tyr Tyr Phe Met Lys Arg Tyr Ser Ser Tyr Gly Val Lys Lys
    450                 455                 460
Thr Leu Tyr Val His Leu Leu Asn Leu Thr Gly Leu Leu Asn Tyr Asp
465                 470                 475                 480
Thr Arg Ala Tyr Val Thr Ser Leu Tyr Leu Pro Gly Tyr Tyr Asn Ala
                485                 490                 495
Val Glu Met Ser Phe Thr Glu Glu Lys Glu Phe Ser Lys Leu Phe Glu
            500                 505                 510
Ser Leu Ile Gln Cys Ile Glu Lys Cys His Ser Asp Gln Ala Arg Gln
            515                 520                 525
Ile Ser Lys Asp Ser Asn Leu Leu Asn Ile Thr Lys Cys Asp Leu
        530                 535             540
Cys Lys Gly Ala Phe Leu Tyr Ala Asn Met Lys Phe Asp Glu Val Pro
545                 550                 555                 560
Ser Met Leu Gln Lys Phe Tyr Val Tyr Leu Thr Lys Gly Leu Lys Ile
                565                 570                 575
Gln Lys Val Ser Ser Leu Ile Lys Thr Leu Asp Ile Tyr Gln Asp Tyr
            580                 585                 590
Ser Asn Tyr Leu Ser His Asp Ile Asn Trp Tyr Thr Phe Leu Phe Leu
            595                 600                 605
Phe Arg Leu Thr Ser Phe Lys Glu Ile Ala Lys Lys Asn Val Ala Glu
        610                 615             620
Ala Met Tyr Leu Asn Ile Lys Asp Glu Asp Thr Phe Asn Lys Thr Val
625                 630                 635                 640
Val Thr Asn Tyr Trp Tyr Pro Ser Pro Ile Lys Lys Tyr Tyr Thr Leu
                645                 650                 655
Tyr Val Arg Lys His Ile Pro Asn Asn Leu Val Asp Glu Leu Glu Lys
            660                 665                 670
Leu Met Lys Ser Gly Thr Leu Glu Lys Met Lys Lys Ser Leu Thr Phe
            675                 680                 685
Leu Val His Val Asn Ser Phe Leu Gln Leu Asp Phe Phe His Gln Leu
        690                 695             700
Asn Glu Pro Pro Leu Gly Leu Pro Arg Ser Tyr Pro Leu Ser Leu Val
705                 710                 715                 720
Leu Glu His Lys Phe Lys Glu Trp Met Asn Ser Ser Pro Ala Gly Phe
                725                 730                 735
Tyr Phe Ser Asn Tyr Gln Asn Pro Tyr Ile Arg Lys Asp Leu His Asp
            740                 745                 750
Lys Val Leu Ser Gln Lys Phe Glu Pro Pro Lys Met Asn Gln Trp Asn
            755                 760                 765
```

Lys Val Leu Lys Ser Leu Ile Glu Cys Ala Tyr Asp Met Tyr Phe Glu
770                 775                 780

Gln Arg His Val Lys Asn Leu Tyr Lys Tyr His Asn Ile Tyr Asn Ile
785                 790                 795                 800

Asn Asn Lys Leu Met Leu Met Arg Asp Ser Ile Asp Leu Tyr Lys Asn
            805                 810                 815

Asn Phe Asp Asp Val Leu Phe Phe Ala Asp Ile Phe Asn Met Arg Lys
            820                 825                 830

Tyr Met Thr Ala Thr Pro Val Tyr Lys Lys Val Lys Asp Arg Val Tyr
            835                 840                 845

His Thr Leu His Ser Ile Thr Gly Asn Ser Val Asn Phe Tyr Lys Tyr
850                 855                 860

Gly Ile Ile Tyr Gly Phe Lys Val Asn Lys Glu Ile Leu Lys Glu Val
865                 870                 875                 880

Val Asp Glu Leu Tyr Ser Ile Tyr Asn Phe Asn Thr Asp Ile Phe Thr
            885                 890                 895

Asp Thr Ser Phe Leu Gln Thr Val Tyr Leu Leu Phe Arg Arg Ile Glu
            900                 905                 910

Glu Thr Tyr Arg Thr Gln Arg Arg Asp Asp Lys Ile Ser Val Asn Asn
            915                 920                 925

Val Phe Phe Met Asn Val Ala Asn Asn Tyr Ser Lys Leu Asn Lys Glu
930                 935                 940

Glu Arg Glu Ile Glu Ile His Asn Ser Met Ala Ser Arg Tyr Tyr Ala
945                 950                 955                 960

Lys Thr Met Phe Ala Ala Phe Gln Met Leu Phe Ser Thr Met Leu Ser
            965                 970                 975

Asn Asn Val Asp Asn Leu Asp Lys Ala Tyr Gly Leu Ser Glu Asn Ile
            980                 985                 990

Gln Val Ala Thr Ser Thr Ser Ala Phe Leu Thr Phe Ala Tyr Val Tyr
            995                 1000                1005

Asn Gly Ser Ile Met Asp Ser Val Thr Asn Ser Leu Leu Pro Pro
    1010                1015                1020

Tyr Ala Lys Lys Pro Ile Thr Gln Leu Lys Tyr Gly Lys Thr Phe
    1025                1030                1035

Val Phe Ser Asn Tyr Phe Met Leu Ala Ser Lys Met Tyr Asp Met
    1040                1045                1050

Leu Asn Tyr Lys Asn Leu Ser Leu Leu Cys Glu Tyr Gln Ala Val
    1055                1060                1065

Ala Ser Ala Asn Phe Tyr Ser Ala Lys Lys Val Gly Gln Phe Leu
    1070                1075                1080

Gly Arg Lys Phe Leu Pro Ile Thr Thr Tyr Phe Leu Val Met Arg
    1085                1090                1095

Ile Ser Trp Thr His Ala Phe Thr Thr Gly Gln His Leu Ile Ser
    1100                1105                1110

Ala Phe Gly Ser Pro Ser Ser Thr Ala Asn Gly Lys Ser Asn Ala
    1115                1120                1125

Ser Gly Tyr Lys Ser Pro Glu Ser Phe Phe Thr His Gly Leu
    1130                1135                1140

Ala Ala Glu Ala Ser Lys Tyr Leu Phe Phe Tyr Phe Phe Thr Asn
    1145                1150                1155

Leu Tyr Leu Asp Ala Tyr Lys Ser Phe Pro Gly Gly Phe Gly Pro
    1160                1165                1170

| Ala | Ile | Lys | Glu | Gln | Thr | Gln | His | Val | Gln | Glu | Gln | Thr | Tyr | Glu |
|---|---|---|---|---|---|---|---|---|---|---|---|---|---|---|
| 1175 | | | | 1180 | | | | | 1185 | | | | | |

Arg Lys Pro Ser Val His Ser Phe Asn Arg Asn Phe Phe Met Glu
1190                    1195                    1200

Leu Val Asn Gly Phe Met Tyr Ala Phe Cys Phe Phe Ala Ile Ser
1205                    1210                    1215

Gln Met Tyr Ala Tyr Phe Glu Asn Ile Asn Phe Tyr Ile Thr Ser
1220                    1225                    1230

Asn Phe Arg Phe Leu Asp Arg Tyr Tyr Gly Val Phe Asn Lys Tyr
1235                    1240                    1245

Phe Ile Asn Tyr Ala Ile Ile Lys Leu Lys Glu Ile Thr Ser Asp
1250                    1255                    1260

Leu Leu Ile Lys Tyr Glu Arg Glu Ala Tyr Leu Ser Met Lys Lys
1265                    1270                    1275

Tyr Gly Tyr Leu Gly Glu Val Ile Ala Ala Arg Leu Ser Pro Lys
1280                    1285                    1290

Asp Lys Ile Met Asn Tyr Val His Glu Thr Asn Glu Asp Ile Met
1295                    1300                    1305

Ser Asn Leu Arg Arg Tyr Asp Met Glu Asn Ala Phe Lys Asn Lys
1310                    1315                    1320

Met Ser Thr Tyr Val Asp Asp Phe Ala Phe Phe Asp Asp Cys Gly
1325                    1330                    1335

Lys Asn Glu Gln Phe Leu Asn Glu Arg Cys Asp Tyr Cys Pro Val
1340                    1345                    1350

Ile Glu Glu Val Glu Glu Thr Gln Leu Phe Thr Thr Thr Gly Asp
1355                    1360                    1365

Lys Asn Thr Asn Lys Thr Thr Glu Ile Lys Lys Gln Thr Ser Thr
1370                    1375                    1380

Tyr Ile Asp Thr Glu Lys Met Asn Glu Ala Asp Ser Ala Asp Ser
1385                    1390                    1395

Asp Asp Glu Lys Asp Ser Asp Thr Pro Asp Asp Glu Leu Met Ile
1400                    1405                    1410

Ser Arg Phe His
    1415

```
<210> SEQ ID NO 3
<211> LENGTH: 4251
<212> TYPE: DNA
<213> ORGANISM: Plasmodium falciparum

<400> SEQUENCE: 3
atggtttcat tttttaagac tccgatcatt atttttttt tcctcttatg tttaaatgaa    60
aaggtattat gttcaataaa tgaaaatgaa aatttaggcg aaaataaaaa cgaaaatgca   120
aatgtaaaca cacctgaaaa tttaaataaa cttctaaatg agtatgacaa tattgaacaa   180
ttaaaatcca tgataggaaa tgatgaacta cataagaatt taacaatatt agaaaaatta   240
attttagagt ctctagaaaa agataaatta aaatatcctc tccttaaaca aggaactgaa   300
caattgatag atatatcaaa atttaataaa aaaatatatt cagatgcgga tgatgaaacg   360
tacatcatac ctaccgtcca atcaagcttt cacgatattg taaatatga acatcttata   420 aagaacaat caatagaaat ttataattct gatatatcag ataaaattaa gaaaaaata   480 tttattgtaa gaacattgaa acaataaaaa ttaatgctta taccattaaa ttcatacaaa   540
caaaataatg atttgaaatc tgcgctcgaa gaattaaata atgtatttac aaacaaagaa   600
```

```
gctcaaaagg aaagcagtcc aataggcgac catgggacat tctttagaaa attgttaaca      660
catgttagaa caattaaaga aaatgaagat atagaaaata aaggagaaac acttatatta      720
ggcgataata aaatagatgt aatgaattca aacgatttct tttttacaac caactcaaat      780
gtaaaattta tggaaaattt agatgatata acaaatcaat atggattagg tttgattaat      840
catttgggtc ctcatttaat agccttggga cattttgttg tattaaaatt agcactaaaa      900
aattacaaaa attattttga agcaaaaaat ataaaatttt ttagttggca aaaaatttta      960
gagttctcca tgtctgatag atttaaggtt cttgatatga tgtgtaacca tgaatctgta     1020
tattattccg aaaaaaaacg tagaaagaca tatttaaaag tcgacagatc aagcacatct     1080
atggaatgta atatattgga atattttatta cattatttta ataaatacca actagaaata     1140
attaaaacta cacaagatac agatttcgat ttacatggta tgatggaaca taaatatata     1200
aaagattatt tcttttcatt tatgtgtaac gatcctaaag aatgtattat ttatcatacg     1260
aatcaattta aaaagaagc taacgaagaa aacactttc ctgaacaaga agaacctaac     1320
cgtcaaataa gtgcatttaa tttatattta aattattatt atttcatgaa acgttatagt     1380
tcatatggaa caaaaaaaac attatatgtt catttattaa atttaactgg acttttaaac     1440
catgatacaa gagcatacgt gacatccctt tatttaccag atattacaa cgctgtcgaa     1500 atgtctttta cggacgataa agagttttcc cacttttttg aaagcttaat acaatgtatt     1560
gaaaaatgcc attcagacca agcaaggcaa atatcaaaag atagtaattt acttaataat     1620
ataacaaaat gtgatttgtg taaggagcc ttttatatg ctaatatgaa attcgatgaa     1680
gttccttcaa tgttgcaaaa attttacgta tatttaacta aaggtctcaa aatacaaaaa     1740
gtatcatcac taatcaaaac gctagatata tatcaagatt acagtaattt cttatcacat     1800
gatattaatt ggtacacatt cctattttta tttagactta caagttttaa agaaattgca     1860
aataaaaatg ttgctgaagc aatgtattta aatataaaag atgaagacac attcaacaaa     1920
acgatagtaa caaactattg gtacccatct cctataaaaa aatattatac attatatgtt     1980
agaaaacata taccaaataa tttagtagat gaattagaga aattaatgaa aagtggcact     2040
ttagaaaaaa tgaaaaaatc tctcaccttt ttagtacatg tgaattcatt tttacaatta     2100
gattttttcc atcaattaaa tgaaccacct cttggattac ctcgatcata tccattatcg     2160
ttagttctcg aacataaatt taaagaatgg atggacagtt cgccagcagg tttctatttt     2220
tcaaattatc aaaatccata tatcagaaaa gatttgcatg ataaagttttt atcacaaaaa     2280 tttgaaccac ctaaaatgaa tcagtggaac aaagttttga aatcattaat tgaatgcgca     2340
tatgatatgt attttgaaca gagacatgtt aaaaatttat ataaatatca taacatttat     2400
aatataaata acaaattaat gttaatgcga gattcaatcg atttgtataa aaacaatttt     2460
gacgatgtgt tattttttgc ggatatattt aatatgagaa aatatatgac agctacacca     2520
gtatataaaa aagtaaaaga ccgagtgtac catacattgc atagtattac aggaaattct     2580
gtcaattttt ataaatatgg tattatatat ggatttaaag taaacaaaga aatattaaaa     2640
gaagttgtcg atgaattgta ttccatctat aattttaaca ccgacatatt tacggatact     2700 tccttttttac aaaccgtttta tttattattt agaagaatga aagaaaccta taggacccaa     2760
agaagagatg ataaaattag tgtgaataac gtttttttca tgaatgttgc taataattat     2820
tccaaattaa acaagaaga aagagaaatc gaaatacata attccatggc atcaagatat     2880
tatgcaaaaa cgatgtttgc agcatttcaa atgttatttt caacaatgtt gagcaacaat     2940
gtagataatc ttgataaagc atatggatta agtgaaaata tccaagtagc aacaagtact     3000
```

```
tccgctttc ttactttgc atatgtatat aacggaagta taatggatag tgtgactaac    3060
agtttattgc caccatatgc gaagaaacct ataacacaat taaatatgg aaaaaccttc    3120
gttttctcaa actatttcat gctagcatcc aaaatgtatg atatgttaaa ttataaaaat    3180
ttaagtcttt tatgtgaata tcaggctgtg gcaagtgcca atttctactc tgctaaaaag    3240
gtaggtcagt tcttggaag aaaattttta cccataacta catattttct agtaatgaga    3300
attagttgga cacatgcttt tacaactgga caacatttga tttgcgcttt tgatcccaaa    3360
agatgtactc ctgattgtaa aaatagtact agttataaat ctcctcaaag ttttttttac    3420
ggttggcctc ctagttcaga aacatatttg ttctttattt ttttcacaaa tttatacctt    3480
gatgcctata aatctttcc tggaggattt ggtcctgcaa taaaagaaca aactcaacat    3540
gttcaagaac aaacctacga acgcaaaccg tcagttcata gttttaatag aaattttttc    3600
atggaactcg taaatggatt catgtatgcc ttttgttttt ttgcaatttc tcaaatgtat    3660
gcatattttg aaaatattaa ttttatatt acaagtaatt tccgtttctt ggatagatat    3720
tatggtgtat tcaataaata ttttataaac tatgccataa ttaaacttaa agaaattact    3780
agtgatcttt taataaaata tgaacgtgag gcttatttaa gtatgaaaaa atatggttat    3840
ttaggtgaag ttattgcagc tagactttct ccaaaagata aaattatgaa ttatgtgcac    3900
gaaactaacg aagatatcat gagtaattta agaagatatg atatgaaaaa tgctttcaaa    3960
aacaaaatgg ttacttatgt ggatgacttt gctttttttg atgattgtgg caaaaatgaa    4020
caatttttaa atgaaagatg tgattattgc cctgtaattg aagaggtgga agaaacacaa    4080
ttatttacta ccactggtga taaaaatact aatgagacca cggaaataaa aaaacaaact    4140
agtacatata ttgatactga aaaaatgaat gaagcggatt ctgctgatag cgacgatgaa    4200
aaggattttg atactcctga caatgaatta atgatcgcac gatttcatta a    4251
```

<210> SEQ ID NO 4
<211> LENGTH: 1416
<212> TYPE: PRT
<213> ORGANISM: Plasmodium falciparum

<400> SEQUENCE: 4

```
Met Val Ser Phe Phe Lys Thr Pro Ile Ile Phe Phe Phe Leu Leu
1               5                   10                  15

Cys Leu Asn Glu Lys Val Leu Cys Ser Ile Asn Glu Asn Glu Asn Leu
            20                  25                  30

Gly Glu Asn Lys Asn Glu Asn Ala Asn Val Asn Thr Pro Glu Asn Leu
        35                  40                  45

Asn Lys Leu Leu Asn Glu Tyr Asp Asn Ile Glu Gln Leu Lys Ser Met
    50                  55                  60

Ile Gly Asn Asp Glu Leu His Lys Asn Leu Thr Ile Leu Glu Lys Leu
65                  70                  75                  80

Ile Leu Glu Ser Leu Glu Lys Asp Lys Leu Lys Tyr Pro Leu Leu Lys
                85                  90                  95

Gln Gly Thr Glu Gln Leu Ile Asp Ile Ser Lys Phe Asn Lys Lys Asn
            100                 105                 110

Ile Thr Asp Ala Asp Asp Glu Thr Tyr Ile Ile Pro Thr Val Gln Ser
        115                 120                 125

Ser Phe His Asp Ile Val Lys Tyr Glu His Leu Ile Lys Glu Gln Ser
    130                 135                 140

Ile Glu Ile Tyr Asn Ser Asp Ile Ser Asp Lys Ile Lys Lys Lys Ile
```

```
            145                 150                 155                 160
        Phe Ile Val Arg Thr Leu Lys Thr Ile Lys Leu Met Leu Ile Pro Leu
                        165                 170                 175
        Asn Ser Tyr Lys Gln Asn Asn Asp Leu Lys Ser Ala Leu Glu Glu Leu
                        180                 185                 190
        Asn Asn Val Phe Thr Asn Lys Glu Ala Gln Lys Glu Ser Ser Pro Ile
                        195                 200                 205
        Gly Asp His Gly Thr Phe Phe Arg Lys Leu Leu Thr His Val Arg Thr
                        210                 215                 220
        Ile Lys Glu Asn Glu Asp Ile Glu Asn Lys Gly Glu Thr Leu Ile Leu
        225                 230                 235                 240
        Gly Asp Asn Lys Ile Asp Val Met Asn Ser Asn Asp Phe Phe Phe Thr
                        245                 250                 255
        Thr Asn Ser Asn Val Lys Phe Met Glu Asn Leu Asp Asp Ile Thr Asn
                        260                 265                 270
        Gln Tyr Gly Leu Gly Leu Ile Asn His Leu Gly Pro His Leu Ile Ala
                        275                 280                 285
        Leu Gly His Phe Val Val Leu Lys Leu Ala Leu Lys Asn Tyr Lys Asn
                        290                 295                 300
        Tyr Phe Glu Ala Lys Asn Ile Lys Phe Phe Ser Trp Gln Lys Ile Leu
        305                 310                 315                 320
        Glu Phe Ser Met Ser Asp Arg Phe Lys Val Leu Asp Met Met Cys Asn
                        325                 330                 335
        His Glu Ser Val Tyr Tyr Ser Glu Lys Lys Arg Arg Lys Thr Tyr Leu
                        340                 345                 350
        Lys Val Asp Arg Ser Ser Thr Ser Met Glu Cys Asn Ile Leu Glu Tyr
                        355                 360                 365
        Leu Leu His Tyr Phe Asn Lys Tyr Gln Leu Glu Ile Ile Lys Thr Thr
                        370                 375                 380
        Gln Asp Thr Asp Phe Asp Leu His Gly Met Met Glu His Lys Tyr Ile
        385                 390                 395                 400
        Lys Asp Tyr Phe Phe Ser Phe Met Cys Asn Asp Pro Lys Glu Cys Ile
                        405                 410                 415
        Ile Tyr His Thr Asn Gln Phe Lys Lys Glu Ala Asn Glu Glu Asn Thr
                        420                 425                 430
        Phe Pro Glu Gln Glu Glu Pro Asn Arg Gln Ile Ser Ala Phe Asn Leu
                        435                 440                 445
        Tyr Leu Asn Tyr Tyr Phe Met Lys Arg Tyr Ser Ser Tyr Gly Thr
        450                 455                 460
        Lys Lys Thr Leu Tyr Val His Leu Leu Asn Leu Thr Gly Leu Leu Asn
        465                 470                 475                 480
        His Asp Thr Arg Ala Tyr Val Thr Ser Leu Tyr Leu Pro Gly Tyr Tyr
                        485                 490                 495
        Asn Ala Val Glu Met Ser Phe Thr Asp Asp Lys Glu Phe Ser Thr Leu
                        500                 505                 510
        Phe Glu Ser Leu Ile Gln Cys Ile Glu Lys Cys His Ser Asp Gln Ala
                        515                 520                 525
        Arg Gln Ile Ser Lys Asp Ser Asn Leu Leu Asn Ile Thr Lys Cys
                        530                 535                 540
        Asp Leu Cys Lys Gly Ala Phe Leu Tyr Ala Asn Met Lys Phe Asp Glu
        545                 550                 555                 560
        Val Pro Ser Met Leu Gln Lys Phe Tyr Val Tyr Leu Thr Lys Gly Leu
                        565                 570                 575
```

```
Lys Ile Gln Lys Val Ser Ser Leu Ile Lys Thr Leu Asp Ile Tyr Gln
                580                 585                 590

Asp Tyr Ser Asn Phe Leu Ser His Asp Ile Asn Trp Tyr Thr Phe Leu
            595                 600                 605

Phe Leu Phe Arg Leu Thr Ser Phe Lys Glu Ile Ala Asn Lys Asn Val
610                 615                 620

Ala Glu Ala Met Tyr Leu Asn Ile Lys Asp Glu Asp Thr Phe Asn Lys
625                 630                 635                 640

Thr Ile Val Thr Asn Tyr Trp Tyr Pro Ser Pro Ile Lys Lys Tyr Tyr
                645                 650                 655

Thr Leu Tyr Val Arg Lys His Ile Pro Asn Asn Leu Val Asp Glu Leu
            660                 665                 670

Glu Lys Leu Met Lys Ser Gly Thr Leu Glu Lys Met Lys Lys Ser Leu
            675                 680                 685

Thr Phe Leu Val His Val Asn Ser Phe Leu Gln Leu Asp Phe Phe His
            690                 695                 700

Gln Leu Asn Glu Pro Pro Leu Gly Leu Pro Arg Ser Tyr Pro Leu Ser
705                 710                 715                 720

Leu Val Leu Glu His Lys Phe Lys Glu Trp Met Asp Ser Ser Pro Ala
                725                 730                 735

Gly Phe Tyr Phe Ser Asn Tyr Gln Asn Pro Tyr Ile Arg Lys Asp Leu
            740                 745                 750

His Asp Lys Val Leu Ser Gln Lys Phe Glu Pro Pro Lys Met Asn Gln
            755                 760                 765

Trp Asn Lys Val Leu Lys Ser Leu Ile Glu Cys Ala Tyr Asp Met Tyr
770                 775                 780

Phe Glu Gln Arg His Val Lys Asn Leu Tyr Lys Tyr His Asn Ile Tyr
785                 790                 795                 800

Asn Ile Asn Asn Lys Leu Met Leu Met Arg Asp Ser Ile Asp Leu Tyr
                805                 810                 815

Lys Asn Asn Phe Asp Asp Val Leu Phe Phe Ala Asp Ile Phe Asn Met
            820                 825                 830

Arg Lys Tyr Met Thr Ala Thr Pro Val Tyr Lys Val Lys Asp Arg
            835                 840                 845

Val Tyr His Thr Leu His Ser Ile Thr Gly Asn Ser Val Asn Phe Tyr
850                 855                 860

Lys Tyr Gly Ile Ile Tyr Gly Phe Lys Val Asn Lys Glu Ile Leu Lys
865                 870                 875                 880

Glu Val Val Asp Glu Leu Tyr Ser Ile Tyr Asn Phe Asn Thr Asp Ile
                885                 890                 895

Phe Thr Asp Thr Ser Phe Leu Gln Thr Val Tyr Leu Leu Phe Arg Arg
            900                 905                 910

Ile Glu Glu Thr Tyr Arg Thr Gln Arg Arg Asp Asp Lys Ile Ser Val
            915                 920                 925

Asn Asn Val Phe Phe Met Asn Val Ala Asn Asn Tyr Ser Lys Leu Asn
930                 935                 940

Lys Glu Glu Arg Glu Ile Glu Ile His Asn Ser Met Ala Ser Arg Tyr
945                 950                 955                 960

Tyr Ala Lys Thr Met Phe Ala Ala Phe Gln Met Leu Phe Ser Thr Met
                965                 970                 975

Leu Ser Asn Asn Val Asp Asn Leu Asp Lys Ala Tyr Gly Leu Ser Glu
            980                 985                 990
```

Asn Ile Gln Val Ala Thr Ser Thr Ser Ala Phe Leu Thr Phe Ala Tyr
     995                 1000                    1005

Val Tyr Asn Gly Ser Ile Met Asp Ser Val Thr Asn Ser Leu Leu
    1010                1015                    1020

Pro Pro Tyr Ala Lys Lys Pro Ile Thr Gln Leu Lys Tyr Gly Lys
    1025                1030                    1035

Thr Phe Val Phe Ser Asn Tyr Phe Met Leu Ala Ser Lys Met Tyr
    1040                1045                    1050

Asp Met Leu Asn Tyr Lys Asn Leu Ser Leu Leu Cys Glu Tyr Gln
    1055                1060                    1065

Ala Val Ala Ser Ala Asn Phe Tyr Ser Ala Lys Lys Val Gly Gln
    1070                1075                    1080

Phe Leu Gly Arg Lys Phe Leu Pro Ile Thr Thr Tyr Phe Leu Val
    1085                1090                    1095

Met Arg Ile Ser Trp Thr His Ala Phe Thr Thr Gly Gln His Leu
    1100                1105                    1110

Ile Cys Ala Phe Asp Pro Lys Arg Cys Thr Pro Asp Cys Lys Asn
    1115                1120                    1125

Ser Thr Ser Tyr Lys Ser Pro Gln Ser Phe Phe Tyr Gly Trp Pro
    1130                1135                    1140

Pro Ser Ser Glu Thr Tyr Leu Phe Phe Tyr Phe Phe Thr Asn Leu
    1145                1150                    1155

Tyr Leu Asp Ala Tyr Lys Ser Phe Pro Gly Gly Phe Gly Pro Ala
    1160                1165                    1170

Ile Lys Glu Gln Thr Gln His Val Gln Glu Gln Thr Tyr Glu Arg
    1175                1180                    1185

Lys Pro Ser Val His Ser Phe Asn Arg Asn Phe Phe Met Glu Leu
    1190                1195                    1200

Val Asn Gly Phe Met Tyr Ala Phe Cys Phe Phe Ala Ile Ser Gln
    1205                1210                    1215

Met Tyr Ala Tyr Phe Glu Asn Ile Asn Phe Tyr Ile Thr Ser Asn
    1220                1225                    1230

Phe Arg Phe Leu Asp Arg Tyr Tyr Gly Val Phe Asn Lys Tyr Phe
    1235                1240                    1245

Ile Asn Tyr Ala Ile Ile Lys Leu Lys Glu Ile Thr Ser Asp Leu
    1250                1255                    1260

Leu Ile Lys Tyr Glu Arg Glu Ala Tyr Leu Ser Met Lys Lys Tyr
    1265                1270                    1275

Gly Tyr Leu Gly Glu Val Ile Ala Ala Arg Leu Ser Pro Lys Asp
    1280                1285                    1290

Lys Ile Met Asn Tyr Val His Glu Thr Asn Glu Asp Ile Met Ser
    1295                1300                    1305

Asn Leu Arg Arg Tyr Asp Met Glu Asn Ala Phe Lys Asn Lys Met
    1310                1315                    1320

Val Thr Tyr Val Asp Asp Phe Ala Phe Phe Asp Asp Cys Gly Lys
    1325                1330                    1335

Asn Glu Gln Phe Leu Asn Glu Arg Cys Asp Tyr Cys Pro Val Ile
    1340                1345                    1350

Glu Glu Val Glu Glu Thr Gln Leu Phe Thr Thr Thr Gly Asp Lys
    1355                1360                    1365

Asn Thr Asn Glu Thr Thr Glu Ile Lys Lys Gln Thr Ser Thr Tyr
    1370                1375                    1380

Ile Asp Thr Glu Lys Met Asn Glu Ala Asp Ser Ala Asp Ser Asp

```
                    1385              1390              1395
Asp Glu Lys Asp Phe Asp Thr Pro Asp Asn Glu Leu Met Ile Ala
        1400              1405              1410

Arg Phe His
    1415

<210> SEQ ID NO 5
<211> LENGTH: 38
<212> TYPE: DNA
<213> ORGANISM: Artificial Sequence
<220> FEATURE:
<223> OTHER INFORMATION: Synthetic

<400> SEQUENCE: 5
ataccgtcga cttgtcaatt tttatgtttg cataaacg                              38

<210> SEQ ID NO 6
<211> LENGTH: 42
<212> TYPE: DNA
<213> ORGANISM: Artificial Sequence
<220> FEATURE:
<223> OTHER INFORMATION: Synthetic

<400> SEQUENCE: 6
aattaggtac cgtacaaata aatacaatat ttttcatagc aa                         42

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
tatccgtcga ctctatttac actcatgaag acagaggtaa                            40

<210> SEQ ID NO 8
<211> LENGTH: 38
<212> TYPE: DNA
<213> ORGANISM: Artificial Sequence
<220> FEATURE:
<223> OTHER INFORMATION: Synthetic

<400> SEQUENCE: 8
aattaggtac ccttcattga aaattttaca agggtatc                              38

<210> SEQ ID NO 9
<211> LENGTH: 41
<212> TYPE: DNA
<213> ORGANISM: Artificial Sequence
<220> FEATURE:
<223> OTHER INFORMATION: Synthetic

<400> SEQUENCE: 9
ataccgtcga ctatgaatga ttgtactact tttgtaagaa t                          41

<210> SEQ ID NO 10
<211> LENGTH: 38
<212> TYPE: DNA
<213> ORGANISM: Artificial Sequence
<220> FEATURE:
<223> OTHER INFORMATION: Synthetic

<400> SEQUENCE: 10
aatatggtac ctacacattg acatagggta tcatcatt                              38
```

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
ataccgtcga ccctttttac acgtatattc ggacaatc                              38

<210> SEQ ID NO 12
<211> LENGTH: 37
<212> TYPE: DNA
<213> ORGANISM: Artificial Sequence
<220> FEATURE:
<223> OTHER INFORMATION: Synthetic

<400> SEQUENCE: 12
aattaggtac cgttaacacg aacaattttg cagtatg                               37

<210> SEQ ID NO 13
<211> LENGTH: 33
<212> TYPE: DNA
<213> ORGANISM: Artificial Sequence
<220> FEATURE:
<223> OTHER INFORMATION: Synthetic

<400> SEQUENCE: 13
ataccgtcga ccaaaaaacc gaaatggcat ttc                                   33

<210> SEQ ID NO 14
<211> LENGTH: 39
<212> TYPE: DNA
<213> ORGANISM: Artificial Sequence
<220> FEATURE:
<223> OTHER INFORMATION: Synthetic

<400> SEQUENCE: 14
aattaggtac catgaaatat gtaatacgtg ggttaaaag                             39

<210> SEQ ID NO 15
<211> LENGTH: 41
<212> TYPE: DNA
<213> ORGANISM: Artificial Sequence
<220> FEATURE:
<223> OTHER INFORMATION: Synthetic

<400> SEQUENCE: 15
ataccgtcga cttccatgtt taaagtgaaa ttagaagata t                          41

<210> SEQ ID NO 16
<211> LENGTH: 33
<212> TYPE: DNA
<213> ORGANISM: Artificial Sequence
<220> FEATURE:
<223> OTHER INFORMATION: Synthetic

<400> SEQUENCE: 16
aattaggtac ccgacattat gttatttcgg cga                                   33

<210> SEQ ID NO 17
<211> LENGTH: 42
<212> TYPE: DNA
<213> ORGANISM: Artificial Sequence
<220> FEATURE:

<223> OTHER INFORMATION: Synthetic

<400> SEQUENCE: 17
ataccgtcga ccagtatata taatcaaatt gagcttaaaa ag         42

<210> SEQ ID NO 18
<211> LENGTH: 41
<212> TYPE: DNA
<213> ORGANISM: Artificial Sequence
<220> FEATURE:
<223> OTHER INFORMATION: Synthetic

<400> SEQUENCE: 18
aattaggtac cagtgtttta aggcaataat tatattgtat t          41

<210> SEQ ID NO 19
<211> LENGTH: 40
<212> TYPE: DNA
<213> ORGANISM: Artificial Sequence
<220> FEATURE:
<223> OTHER INFORMATION: Synthetic

<400> SEQUENCE: 19
tcgacctcga gcataaaatt gtgtgtttca ttaaaatcat            40

<210> SEQ ID NO 20
<211> LENGTH: 41
<212> TYPE: DNA
<213> ORGANISM: Artificial Sequence
<220> FEATURE:
<223> OTHER INFORMATION: Synthetic

<400> SEQUENCE: 20
acgtagggcc catgtataaa tgaaaaatga atgtgactct t          41

<210> SEQ ID NO 21
<211> LENGTH: 41
<212> TYPE: DNA
<213> ORGANISM: Artificial Sequence
<220> FEATURE:
<223> OTHER INFORMATION: Synthetic

<400> SEQUENCE: 21
attcagtcga caagaaaaag gtaatatttt agtacactca a          41

<210> SEQ ID NO 22
<211> LENGTH: 38
<212> TYPE: DNA
<213> ORGANISM: Artificial Sequence
<220> FEATURE:
<223> OTHER INFORMATION: Synthetic

<400> SEQUENCE: 22
tattcggtac ctttgtaata tacctttatg cgttgaca              38

<210> SEQ ID NO 23
<211> LENGTH: 38
<212> TYPE: DNA
<213> ORGANISM: Artificial Sequence
<220> FEATURE:
<223> OTHER INFORMATION: Synthetic

<400> SEQUENCE: 23
atgcagtcga catgcactca ttaataattt taaaccgt              38

<210> SEQ ID NO 24
<211> LENGTH: 41
<212> TYPE: DNA
<213> ORGANISM: Artificial Sequence
<220> FEATURE:
<223> OTHER INFORMATION: Synthetic

<400> SEQUENCE: 24
tcgatgggcc cctttcaat taatttata ttcttttgtt c    41

<210> SEQ ID NO 25
<211> LENGTH: 37
<212> TYPE: DNA
<213> ORGANISM: Artificial Sequence
<220> FEATURE:
<223> OTHER INFORMATION: Synthetic

<400> SEQUENCE: 25
ataccgtcga ccctgacgat gaattaatga tatcacg    37

<210> SEQ ID NO 26
<211> LENGTH: 40
<212> TYPE: DNA
<213> ORGANISM: Artificial Sequence
<220> FEATURE:
<223> OTHER INFORMATION: Synthetic

<400> SEQUENCE: 26
tataaggtac ccaggttaat atagccaaaa taaattgaaa    40

<210> SEQ ID NO 27
<211> LENGTH: 36
<212> TYPE: DNA
<213> ORGANISM: Artificial Sequence
<220> FEATURE:
<223> OTHER INFORMATION: Synthetic

<400> SEQUENCE: 27
atagagtcga cggatattag ctgataaagc agcagc    36

<210> SEQ ID NO 28
<211> LENGTH: 37
<212> TYPE: DNA
<213> ORGANISM: Artificial Sequence
<220> FEATURE:
<223> OTHER INFORMATION: Synthetic

<400> SEQUENCE: 28
gatttggtac ctttgttttc atgtcccatc ataattc    37

<210> SEQ ID NO 29
<211> LENGTH: 41
<212> TYPE: DNA
<213> ORGANISM: Artificial Sequence
<220> FEATURE:
<223> OTHER INFORMATION: Synthetic

<400> SEQUENCE: 29
ataccgtcga ctattctact taaagatgaa tagcacatat g    41

<210> SEQ ID NO 30
<211> LENGTH: 36
<212> TYPE: DNA
<213> ORGANISM: Artificial Sequence
<220> FEATURE:
<223> OTHER INFORMATION: Synthetic

<400> SEQUENCE: 30
acattgggcc cttcccctca catatcaatc ataaat        36

<210> SEQ ID NO 31
<211> LENGTH: 34
<212> TYPE: DNA
<213> ORGANISM: Artificial Sequence
<220> FEATURE:
<223> OTHER INFORMATION: Synthetic

<400> SEQUENCE: 31
atacagtcga cgcatcctat tcccatcctt tcct        34

<210> SEQ ID NO 32
<211> LENGTH: 35
<212> TYPE: DNA
<213> ORGANISM: Artificial Sequence
<220> FEATURE:
<223> OTHER INFORMATION: Synthetic

<400> SEQUENCE: 32
actgagggcc cgacaagaag cattacagag agcaa        35

<210> SEQ ID NO 33
<211> LENGTH: 41
<212> TYPE: DNA
<213> ORGANISM: Artificial Sequence
<220> FEATURE:
<223> OTHER INFORMATION: Synthetic

<400> SEQUENCE: 33
ataccgtcga cattttgccc aagaatataa aataataaga t        41

<210> SEQ ID NO 34
<211> LENGTH: 41
<212> TYPE: DNA
<213> ORGANISM: Artificial Sequence
<220> FEATURE:
<223> OTHER INFORMATION: Synthetic

<400> SEQUENCE: 34
aattaggtac ccagagaaag aaaaatgtca atataaataa a        41

<210> SEQ ID NO 35
<211> LENGTH: 33
<212> TYPE: DNA
<213> ORGANISM: Artificial Sequence
<220> FEATURE:
<223> OTHER INFORMATION: Synthetic

<400> SEQUENCE: 35
cataagcggc cgcgccattc agaccaagca agg        33

<210> SEQ ID NO 36
<211> LENGTH: 41
<212> TYPE: DNA
<213> ORGANISM: Artificial Sequence
<220> FEATURE:
<223> OTHER INFORMATION: Synthetic

<400> SEQUENCE: 36
ttaaactgca gcttttcaat taattttata ttcttttgtt c        41

<210> SEQ ID NO 37
<211> LENGTH: 21

```
<212> TYPE: PRT
<213> ORGANISM: Artificial Sequence
<220> FEATURE:
<223> OTHER INFORMATION: Synthetic

<400> SEQUENCE: 37

Phe Leu Asn Cys Cys Pro Cys Cys Met Glu Pro Gly Ser Asp Tyr Lys
1               5                   10                  15

Asp Asp Asp Asp Lys
            20

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
gtggaattgt gagcggataa ca                                       22

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
tcatcgtcct tatagtcgga tcc                                      23

<210> SEQ ID NO 40
<211> LENGTH: 26
<212> TYPE: DNA
<213> ORGANISM: Artificial Sequence
<220> FEATURE:
<223> OTHER INFORMATION: Synthetic

<400> SEQUENCE: 40
atgttttgta atttatggga tagcga                                   26

<210> SEQ ID NO 41
<211> LENGTH: 28
<212> TYPE: DNA
<213> ORGANISM: Artificial Sequence
<220> FEATURE:
<223> OTHER INFORMATION: Synthetic

<400> SEQUENCE: 41
gttgagtacg cactaatatg tcaatttg                                 28

<210> SEQ ID NO 42
<211> LENGTH: 32
<212> TYPE: DNA
<213> ORGANISM: Artificial Sequence
<220> FEATURE:
<223> OTHER INFORMATION: Synthetic

<400> SEQUENCE: 42
aaccataaca ttatcatata tgttaattac ac                            32

<210> SEQ ID NO 43
<211> LENGTH: 22
<212> TYPE: DNA
<213> ORGANISM: Artificial Sequence
<220> FEATURE:
```

<223> OTHER INFORMATION: Synthetic

<400> SEQUENCE: 43
atttccagag aatgaccaca ac                                              22

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
ttaagatggc ctgggtgatt c                                               21

<210> SEQ ID NO 45
<211> LENGTH: 27
<212> TYPE: DNA
<213> ORGANISM: Artificial Sequence
<220> FEATURE:
<223> OTHER INFORMATION: Synthetic

<400> SEQUENCE: 45
ctcttactac ttattatcta tctctca                                         27

<210> SEQ ID NO 46
<211> LENGTH: 19
<212> TYPE: DNA
<213> ORGANISM: Artificial Sequence
<220> FEATURE:
<223> OTHER INFORMATION: Synthetic

<400> SEQUENCE: 46
ccaggcgtag gtcctttac                                                  19

<210> SEQ ID NO 47
<211> LENGTH: 28
<212> TYPE: DNA
<213> ORGANISM: Artificial Sequence
<220> FEATURE:
<223> OTHER INFORMATION: Synthetic

<400> SEQUENCE: 47
acccataact acatattttc tagtaatg                                        28

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
gacaagttcc agaagcatcc t                                               21

<210> SEQ ID NO 49
<211> LENGTH: 28
<212> TYPE: DNA
<213> ORGANISM: Artificial Sequence
<220> FEATURE:
<223> OTHER INFORMATION: Synthetic

<400> SEQUENCE: 49
acccataact acatattttc tagtaatg                                        28

```
<210> SEQ ID NO 50
<211> LENGTH: 30
<212> TYPE: DNA
<213> ORGANISM: Artificial Sequence
<220> FEATURE:
<223> OTHER INFORMATION: Synthetic

<400> SEQUENCE: 50
agatttagtt acacttgaag aattagtatt                                              30

<210> SEQ ID NO 51
<211> LENGTH: 28
<212> TYPE: DNA
<213> ORGANISM: Artificial Sequence
<220> FEATURE:
<223> OTHER INFORMATION: Synthetic

<400> SEQUENCE: 51
acccataact acatattttc tagtaatg                                                28

<210> SEQ ID NO 52
<211> LENGTH: 27
<212> TYPE: DNA
<213> ORGANISM: Artificial Sequence
<220> FEATURE:
<223> OTHER INFORMATION: Synthetic

<400> SEQUENCE: 52
gatttataac taggagcact acattta                                                 27

<210> SEQ ID NO 53
<211> LENGTH: 28
<212> TYPE: DNA
<213> ORGANISM: Artificial Sequence
<220> FEATURE:
<223> OTHER INFORMATION: Synthetic

<400> SEQUENCE: 53
acccataact acatattttc tagtaatg                                                28

<210> SEQ ID NO 54
<211> LENGTH: 26
<212> TYPE: DNA
<213> ORGANISM: Artificial Sequence
<220> FEATURE:
<223> OTHER INFORMATION: Synthetic

<400> SEQUENCE: 54
ttataaccat taggagcact actttc                                                  26

<210> SEQ ID NO 55
<211> LENGTH: 28
<212> TYPE: DNA
<213> ORGANISM: Artificial Sequence
<220> FEATURE:
<223> OTHER INFORMATION: Synthetic

<400> SEQUENCE: 55
acccataact acatattttc tagtaatg                                                28

<210> SEQ ID NO 56
<211> LENGTH: 21
<212> TYPE: DNA
<213> ORGANISM: Artificial Sequence
<220> FEATURE:
<223> OTHER INFORMATION: Synthetic
```

-continued

<400> SEQUENCE: 56
gacaagttcc agaagcatcc t                                                    21

<210> SEQ ID NO 57
<211> LENGTH: 24
<212> TYPE: DNA
<213> ORGANISM: Artificial Sequence
<220> FEATURE:
<223> OTHER INFORMATION: Synthetic

<400> SEQUENCE: 57
gttactacaa cattcctgat tcag                                                 24

<210> SEQ ID NO 58
<211> LENGTH: 27
<212> TYPE: DNA
<213> ORGANISM: Artificial Sequence
<220> FEATURE:
<223> OTHER INFORMATION: Synthetic

<400> SEQUENCE: 58
aatgaaaata taaaaatgct gggggat                                              27

<210> SEQ ID NO 59
<211> LENGTH: 27
<212> TYPE: DNA
<213> ORGANISM: Artificial Sequence
<220> FEATURE:
<223> OTHER INFORMATION: Synthetic

<400> SEQUENCE: 59
taccattagt gttttataca cttaagg                                              27

<210> SEQ ID NO 60
<211> LENGTH: 23
<212> TYPE: DNA
<213> ORGANISM: Artificial Sequence
<220> FEATURE:
<223> OTHER INFORMATION: Synthetic

<400> SEQUENCE: 60
ccaaaatatg gccaagtact tgc                                                  23

<210> SEQ ID NO 61
<211> LENGTH: 164
<212> TYPE: PRT
<213> ORGANISM: Artificial Sequence
<220> FEATURE:
<223> OTHER INFORMATION: Synthetic

<400> SEQUENCE: 61

Met Gly Ser Ser His His His His His His Ser Ser Gly Gly Thr Lys
1               5                   10                  15

Lys Tyr Gly Tyr Leu Gly Glu Val Ile Ala Ala Arg Leu Ser Pro Lys
            20                  25                  30

Asp Lys Ile Met Asn Tyr Val His Glu Thr Asn Glu Asp Ile Met Ser
        35                  40                  45

Asn Leu Arg Arg Tyr Asp Met Glu Asn Ala Phe Lys Asn Lys Met Ser
    50                  55                  60

Thr Tyr Val Asp Asp Phe Ala Phe Phe Asp Cys Gly Lys Asn Glu
65                  70                  75                  80

Gln Phe Leu Asn Glu Arg Cys Asp Tyr Cys Pro Val Ile Glu Glu Val
                85                  90                  95

Glu Glu Thr Gln Leu Phe Thr Thr Thr Gly Asp Lys Asn Thr Asn Lys
            100                 105                 110

Thr Thr Glu Ile Lys Lys Gln Thr Ser Thr Tyr Ile Asp Thr Glu Lys
            115                 120                 125

Met Asn Glu Ala Asp Ser Ala Asp Ser Asp Glu Lys Asp Ser Asp
130                 135                 140

Thr Pro Asp Asp Glu Leu Met Ile Ser Arg Phe His Asp Tyr Lys Asp
145                 150                 155                 160

Asp Asp Asp Lys

<210> SEQ ID NO 62
<211> LENGTH: 146
<212> TYPE: PRT
<213> ORGANISM: Plasmodium falciparum

<400> SEQUENCE: 62

Cys Glu Tyr Gln Ala Val Ala Ser Ala Asn Phe Tyr Ser Ala Lys Lys
1               5                   10                  15

Val Gly Gln Phe Leu Gly Arg Lys Phe Leu Pro Ile Thr Thr Tyr Phe
            20                  25                  30

Leu Val Met Arg Ile Ser Trp Thr His Ala Phe Thr Thr Gly Gln His
            35                  40                  45

Leu Ile Ser Ala Phe Gly Ser Pro Ser Thr Ala Asn Gly Lys Ser
50                  55                  60

Asn Ala Ser Gly Tyr Lys Ser Pro Glu Ser Phe Phe Thr His Gly
65                  70                  75                  80

Leu Ala Ala Glu Ala Ser Lys Tyr Leu Phe Phe Tyr Phe Thr Asn
            85                  90                  95

Leu Tyr Leu Asp Ala Tyr Lys Ser Phe Pro Gly Gly Phe Gly Pro Ala
            100                 105                 110

Ile Lys Glu Gln Thr Gln His Val Gln Glu Gln Thr Tyr Glu Arg Lys
            115                 120                 125

Pro Ser Val His Ser Phe Asn Arg Asn Phe Phe Met Glu Leu Val Asn
            130                 135                 140

Gly Phe
145

<210> SEQ ID NO 63
<211> LENGTH: 438
<212> TYPE: DNA
<213> ORGANISM: Plasmodium falciparum

<400> SEQUENCE: 63
tgtgaatatc aggctgtggc aagtgccaat ttctactctg ctaaaaaggt aggtcagttt     60
cttggaagaa aattttacc cataactaca tattttctag taatgagaat tagttggaca    120
catgctttta caactggaca acatttgatt agcgcttttg gttccccaag ttctactgct    180
aatggtaaaa gtaatgctag tggttataaa tcccctgaaa gttttttctt cactcacgga    240
cttgctgctg aagcatccaa atatttattt ttttattttt tcacaaattt ataccttgat    300
gcctacaaat cttttcctgg aggatttggt cctgcaataa aagaacaaac tcaacatgtt    360
caagaacaaa cctacgaacg caaaccgtca gttcatagtt ttaatagaaa ttttttcatg    420
gaactcgtaa atggattc                                                  438

<210> SEQ ID NO 64

<211> LENGTH: 186
<212> TYPE: PRT
<213> ORGANISM: Plasmodium falciparum

<400> SEQUENCE: 64

Thr Ser Asn Phe Arg Phe Leu Asp Arg Tyr Tyr Gly Val Phe Asn Lys
1               5                   10                  15

Tyr Phe Ile Asn Tyr Ala Ile Ile Lys Leu Lys Glu Ile Thr Ser Asp
            20                  25                  30

Leu Leu Ile Lys Tyr Glu Arg Glu Ala Tyr Leu Ser Met Lys Lys Tyr
        35                  40                  45

Gly Tyr Leu Gly Glu Val Ile Ala Ala Arg Leu Ser Pro Lys Asp Lys
    50                  55                  60

Ile Met Asn Tyr Val His Glu Thr Asn Glu Asp Ile Met Ser Asn Leu
65                  70                  75                  80

Arg Arg Tyr Asp Met Glu Asn Ala Phe Lys Asn Lys Met Ser Thr Tyr
                85                  90                  95

Val Asp Asp Phe Ala Phe Phe Asp Cys Gly Lys Asn Glu Gln Phe
            100                 105                 110

Leu Asn Glu Arg Cys Asp Tyr Cys Pro Val Ile Glu Glu Val Glu Glu
        115                 120                 125

Thr Gln Leu Phe Thr Thr Thr Gly Asp Lys Asn Thr Asn Lys Thr Thr
    130                 135                 140

Glu Ile Lys Lys Gln Thr Ser Thr Tyr Ile Asp Thr Glu Lys Met Asn
145                 150                 155                 160

Glu Ala Asp Ser Ala Asp Ser Asp Glu Lys Asp Ser Asp Thr Pro
                165                 170                 175

Asp Asp Glu Leu Met Ile Ser Arg Phe His
            180                 185

<210> SEQ ID NO 65
<211> LENGTH: 558
<212> TYPE: DNA
<213> ORGANISM: Plasmodium falciparum

<400> SEQUENCE: 65
acaagtaatt tccgtttctt ggatagatat tatggtgtat tcaataaata ttttataaac      60
tatgccataa ttaaacttaa agaaattact agtgatcttt taataaaata tgaacgtgag     120
gcttatttaa gtatgaaaaa atatggttat ttaggtgaag ttattgcagc tagactttct     180
ccaaaagata aaattatgaa ttatgtgcac gaaactaacg aagatatcat gagtaattta     240
agaagatatg atatggaaaa tgctttcaaa acaaaatgt caacatatgt agatgatttt     300 gcttttttg atgattgcgg aaaaaatgaa caattttaa atgagagatg tgattattgt     360
cctgtaattg aagaggtcga agaaacacaa ttatttacta ccactggtga taaaaacact     420
aataagacca cggaaataaa aaaacaaact agtacatata ttgatactga aaaaatgaat     480
gaagcggatt ctgctgatag cgacgatgaa aaggattctg atactcctga cgatgaatta     540
atgatatcac gatttcac                                                  558

<210> SEQ ID NO 66
<211> LENGTH: 308
<212> TYPE: PRT
<213> ORGANISM: Plasmodium falciparum

<400> SEQUENCE: 66

Ser Ile Asn Glu Asn Gln Asn Glu Asn Asp Thr Ile Ser Gln Asn Val

```
            1               5                  10                 15
          Asn Gln His Glu Asn Ile Asn Gln Asn Val Asn Asp Asn Asp Asn Ile
                          20                 25                 30
          Glu Gln Leu Lys Ser Met Ile Gly Asn Asp Glu Leu His Lys Asn Leu
                          35                 40                 45
          Thr Ile Leu Glu Lys Leu Ile Leu Glu Ser Leu Glu Lys Asp Lys Leu
                          50                 55                 60
          Lys Tyr Pro Leu Leu Lys Gln Gly Thr Glu Gln Leu Ile Asp Ile Ser
          65                         70                 75                 80
          Lys Phe Asn Lys Asn Ile Thr Asp Ala Asp Asp Glu Thr Tyr Ile
                                  85                 90                 95
          Ile Pro Thr Val Gln Ser Thr Phe His Asp Ile Val Lys Tyr Glu His
                          100                105                110
          Leu Ile Lys Glu Gln Ser Ile Glu Ile Tyr Asn Ser Asp Ile Ser Asp
                          115                120                125
          Lys Ile Lys Lys Ile Phe Ile Val Arg Thr Leu Lys Thr Ile Lys
                          130                135                140
          Leu Met Leu Ile Pro Leu Asn Ser Tyr Lys Gln Asn Asn Asp Leu Lys
          145                        150                155                160
          Ser Ala Leu Glu Glu Leu Asn Asn Val Phe Thr Asn Lys Glu Ala Gln
                          165                170                175
          Glu Glu Ser Ser Pro Ile Gly Asp His Gly Thr Phe Phe Arg Lys Leu
                          180                185                190
          Leu Thr His Val Arg Thr Ile Lys Glu Asn Glu Asp Ile Glu Asn Lys
                          195                200                205
          Gly Glu Thr Leu Ile Leu Gly Asp Asn Lys Ile Asp Val Met Asn Ser
                          210                215                220
          Asn Asp Phe Phe Phe Thr Thr Asn Ser Asn Val Lys Phe Met Glu Asn
          225                        230                235                240
          Leu Asp Asp Ile Thr Asn Gln Tyr Gly Leu Gly Leu Ile Asn His Leu
                          245                250                255
          Gly Pro His Leu Ile Ala Leu Gly His Phe Thr Val Leu Lys Leu Ala
                          260                265                270
          Leu Lys Asn Tyr Lys Asn Tyr Phe Glu Ala Lys Ser Ile Lys Phe Phe
                          275                280                285
          Ser Trp Gln Lys Ile Leu Glu Phe Ser Met Ser Asp Arg Phe Lys Val
                          290                295                300
          Leu Asp Met Met
          305

<210> SEQ ID NO 67
<211> LENGTH: 924
<212> TYPE: DNA
<213> ORGANISM: Plasmodium falciparum

<400> SEQUENCE: 67
tcaataaatg aaaatcaaaa tgaaaatgat accattagtc aaaatgtcaa ccaacatgaa       60
aatattaatc aaaatgtaaa tgataatgac aatattgaac aattaaaatc catgattgga      120
aatgatgaac tacataagaa tttaacaata ttagaaaaat taattttaga gtctttagaa      180
aaagataaat taaatatcc tctccttaaa caaggaactg aacaattgat agatatatca      240
aaatttaata aaaaaatat tacagatgcg gatgatgaaa cgtacatcat acccaccgtc      300
caatcaacgt ttcacgatat tgtgaaatac gaacatctta taaagaaca atcaatagaa      360
```

```
atttacaatt ctgatatatc agataaaatt aagaaaaaaa tttttatagt aagaacattg    420
aaaaccataa aattaatgct tataccatta aactcgtaca aacaaaataa tgacttgaaa    480
tctgcactcg aagaattaaa taatgtattt acaaacaaag aagctcaaga ggaaagcagt    540
ccaataggcg accatgggac attctttaga aaattgttaa cacatgttag aacaattaaa    600
gaaaatgaag atatagaaaa taaggagaa acacttatat taggcgataa taaaatagat     660
gtaatgaatt caaacgattt ctttttttaca accaactcaa atgtaaaatt tatggaaaat   720
ttagatgata taacaaatca atatggatta ggtttgatta atcatctagg tcctcattta    780
atagccttgg gtcattttac cgtattaaaa ttagcactaa aaaattacaa aaactattt     840 gaagcaaaaa gtattaaatt ttttagttgg caaaaaattt tagagttctc catgtctgat    900
agatttaaag ttcttgatat gatg                                           924
```

<210> SEQ ID NO 68  
<211> LENGTH: 26  
<212> TYPE: DNA  
<213> ORGANISM: Artificial Sequence  
<220> FEATURE:  
<223> OTHER INFORMATION: Synthetic

<400> SEQUENCE: 68

```
gtgcaatata tcaaagtgta catgca                                          26
```

<210> SEQ ID NO 69  
<211> LENGTH: 27  
<212> TYPE: DNA  
<213> ORGANISM: Artificial Sequence  
<220> FEATURE:  
<223> OTHER INFORMATION: Synthetic

<400> SEQUENCE: 69

```
aagaaaataa atgcaaaaca agttaga                                         27
```

<210> SEQ ID NO 70  
<211> LENGTH: 27  
<212> TYPE: DNA  
<213> ORGANISM: Artificial Sequence  
<220> FEATURE:  
<223> OTHER INFORMATION: Synthetic

<400> SEQUENCE: 70

```
atttacaaac aaagaagctc aagagga                                         27
```

<210> SEQ ID NO 71  
<211> LENGTH: 31  
<212> TYPE: DNA  
<213> ORGANISM: Artificial Sequence  
<220> FEATURE:  
<223> OTHER INFORMATION: Synthetic

<400> SEQUENCE: 71

```
ttttctatat cttcattttc tttaattgtt c                                    31
```

<210> SEQ ID NO 72  
<211> LENGTH: 182  
<212> TYPE: PRT  
<213> ORGANISM: Artificial Sequence  
<220> FEATURE:  
<223> OTHER INFORMATION: Synthetic

<400> SEQUENCE: 72

Cys Glu Tyr Gln Ala Val Ala Ser Ala Asn Phe Tyr Ser Ala Lys Lys

```
                1               5                  10                 15
        Val Gly Gln Phe Ile Gly Arg Lys Phe Leu Pro Ile Thr Thr Tyr Phe
                   20                  25                  30
        Leu Val Met Arg Ile Ser Trp Thr His Ala Ile Thr Thr Gly Gln His
                       35                  40                  45
        Leu Ile Pro Gln Leu Thr Asp Pro Glu Tyr Gly Gln Thr Pro Lys Gly
            50                  55                  60
        Lys Asp Ala Ser Gly Thr Cys Pro Ser Ala Gly Leu Glu Lys Cys Thr
        65                  70                  75                  80
        Asn Tyr Arg Ala Pro Gly Ser Phe Phe Thr His Gly Leu Ala Ala
                        85                  90                  95
        Glu Ala Ser Lys Tyr Leu Phe Phe Tyr Phe Thr Asn Leu Tyr Leu
                        100                 105                 110
        Asp Ala Tyr Lys Ser Phe Pro Gly Gly Phe Gly Pro Ala Ile Lys Glu
                        115                 120                 125
        Gln Thr Gln His Val Gln Glu Gln Thr Tyr Glu Arg Lys Pro Ser Val
                        130                 135                 140
        His Ser Phe Asn Arg Asn Phe Phe Met Glu Leu Ala Asn Gly Phe Met
        145                 150                 155                 160
        Tyr Ala Phe Cys Phe Phe Ala Ile Ser Gln Met Tyr Ala Tyr Phe Glu
                        165                 170                 175
        Asn Ile Asn Phe Tyr Ile
                        180
```

<210> SEQ ID NO 73
<211> LENGTH: 546
<212> TYPE: DNA
<213> ORGANISM: Artificial Sequence
<220> FEATURE:
<223> OTHER INFORMATION: Synthetic

<400> SEQUENCE: 73

```
tgtgaatatc aggcggtagc aagtgcaaat ttctactctg ctaaaaaggt agggcaattt      60
attggaagaa aatttttacc cataactaca tattttctag taatgagaat tagttggaca     120
cacgctatta caactggaca acatttaatt ccccaattaa cagatcctga atacggtcaa     180
actcctaagg gaaaggatgc ttctggaact tgtcctagtg cgggtttaga aaaatgtact     240
aactatagag ctcctggaag ttttttcttt actcacggac ttgctgctga agcatccaaa     300
tatttatttt tttattttt cacaaattta taccttgatg cctacaaatc ttttcctgga     360
ggatttggtc ctgcaataaa agaacaaact caacatgttc aagaacaaac ctacgaacgc     420
aaaccgtcag ttcatagttt taatagaaat tttttcatgg aacttgcaaa tggtttcatg     480
tatgctttt gttttttgc tatttcacaa atgtatgcat attttgaaaa tattaatttt     540
tatatt                                                               546
```

<210> SEQ ID NO 74
<211> LENGTH: 420
<212> TYPE: PRT
<213> ORGANISM: Artificial Sequence
<220> FEATURE:
<223> OTHER INFORMATION: Synthetic

<400> SEQUENCE: 74

```
        Leu Tyr Leu Pro Gly Tyr Tyr Asn Ala Val Glu Met Ser Phe Thr Glu
        1               5                  10                  15

Glu Lys Glu Phe Ser Lys Leu Phe Glu Ser Leu Ile Gln Cys Ile Glu
```

```
                    20                  25                  30
Lys Cys His Ser Asp Gln Ala Arg Gln Ile Ser Lys Asp Ser Asn Leu
                35                  40                  45
Leu Asn Asn Ile Thr Lys Cys Asp Leu Cys Lys Gly Ala Phe Leu Tyr
 50                  55                  60
Ala Asn Met Lys Phe Asp Glu Val Pro Ser Met Leu Gln Lys Phe Tyr
 65                  70                  75                  80
Val Tyr Leu Thr Lys Gly Leu Lys Ile Gln Lys Val Ser Ser Leu Ile
                85                  90                  95
Lys Thr Leu Asp Ile Tyr Gln Asp Tyr Ser Asn Tyr Leu Ser His Asp
                100                 105                 110
Ile Asn Trp Tyr Thr Phe Leu Phe Leu Phe Arg Leu Thr Ser Phe Lys
                115                 120                 125
Glu Ile Ala Lys Lys Asn Val Ala Glu Ala Met Tyr Leu Asn Ile Lys
                130                 135                 140
Asp Glu Asp Thr Phe Asn Lys Thr Val Val Thr Asn Tyr Trp Tyr Pro
145                 150                 155                 160
Ser Pro Ile Lys Lys Tyr Tyr Thr Leu Tyr Val Arg Lys His Ile Pro
                165                 170                 175
Asn Asn Leu Val Asp Glu Leu Glu Lys Leu Met Lys Ser Gly Thr Leu
                180                 185                 190
Glu Lys Met Lys Lys Ser Leu Thr Phe Leu Val His Val Asn Ser Phe
                195                 200                 205
Leu Gln Leu Asp Phe Phe His Gln Leu Asn Glu Pro Pro Leu Gly Leu
                210                 215                 220
Pro Arg Ser Tyr Pro Leu Ser Leu Val Leu Glu His Lys Phe Lys Glu
225                 230                 235                 240
Trp Met Asn Ser Ser Pro Ala Gly Phe Tyr Phe Ser Asn Tyr Gln Asn
                245                 250                 255
Pro Tyr Ile Arg Lys Asp Leu His Asp Lys Val Leu Ser Gln Lys Phe
                260                 265                 270
Glu Pro Pro Lys Met Asn Gln Trp Asn Lys Val Leu Lys Ser Leu Ile
                275                 280                 285
Glu Cys Ala Tyr Asp Met Tyr Phe Glu Gln Arg His Val Lys Asn Leu
                290                 295                 300
Tyr Lys Tyr His Asn Ile Tyr Asn Ile Asn Lys Leu Met Leu Met
305                 310                 315                 320
Arg Asp Ser Ile Asp Leu Tyr Lys Asn Asn Phe Asp Asp Val Leu Phe
                325                 330                 335
Phe Ala Asp Ile Phe Asn Met Arg Lys Tyr Met Thr Ala Thr Pro Val
                340                 345                 350
Tyr Lys Lys Val Lys Asp Arg Val Tyr His Thr Leu His Ser Ile Thr
                355                 360                 365
Gly Asn Ser Val Asn Phe Tyr Lys Tyr Gly Ile Ile Tyr Gly Phe Lys
                370                 375                 380
Val Asn Lys Glu Ile Leu Lys Glu Val Val Asp Glu Leu Tyr Ser Ile
385                 390                 395                 400
Tyr Asn Phe Asn Thr Asp Ile Phe Thr Asp Thr Ser Phe Leu Gln Thr
                405                 410                 415
Val Tyr Leu Leu
            420

<210> SEQ ID NO 75
```

<211> LENGTH: 1260
<212> TYPE: DNA
<213> ORGANISM: Artificial Sequence
<220> FEATURE:
<223> OTHER INFORMATION: Synthetic

<400> SEQUENCE: 75

```
ctttatttac caggatatta caacgctgtc gaaatgtctt ttacggaaga aaaagagttt      60
tccaaacttt ttgaaagctt aatacaatgt attgaaaaat gccattcaga ccaagcaagg     120
caaatatcaa aagatagtaa tttacttaat aatataacaa aatgtgattt gtgtaaagga     180
gccttttat atgctaatat gaattcgat gaagttcctt caatgttgca aaaattttac       240
gtatatttaa ctaaaggtct caaaatacaa aaagtatcat cactaatcaa aacgctagat     300
atatatcaag attacagcaa ttacttatca catgatatta attggtacac attcctattt     360
ttatttagac ttacaagttt taaagaaatt gcaaagaaaa atgttgctga agcaatgtat     420
ttaaatataa aagatgaaga cacattcaac aaaacggtag taacaaacta ttggtaccca     480
tctcctataa aaaatatta tacattatat gttagaaaac ataccaaa taatttagta       540
gatgaattgg agaaattaat gaaaagtggc actttagaaa aaatgaaaaa atctctcacc     600
ttttagtac atgtgaattc atttttacaa ttagattttt tccatcaatt aaatgaacca     660
cctcttggat tacctcgatc atatccatta tcgttagttc tcgaacataa atttaaagaa     720
tggatgaaca gttcgccagc aggtttctat ttttcaaatt atcaaaatcc atatatcaga     780
aaagatttgc atgataaagt tttatcacaa aaatttgaac cacctaaaat gaatcagtgg     840
aacaaagttt tgaaatcatt aattgaatgc gcatatgata tgtatttga acagagacat      900
gttaaaaatt tatataaata tcataacatt tataatataa ataacaaatt aatgttaatg     960
cgagattcaa tcgatttgta taaaaacaat tttgacgatg tgttattttt tgcggatata    1020
tttaatatga gaaaatatat gacagctaca ccagtatata aaaaagtaaa agacagagtg    1080
taccatacat tgcatagtat tacaggaaat tctgtcaatt tttataaata tggtattata    1140
tatggattta agtaaacaa agaaatatta aaagaagttg tcgatgaatt gtattccatc    1200
tataatttta acaccgacat atttacggat acttcctttt tacaaaccgt ttattatta    1260
```

<210> SEQ ID NO 76
<211> LENGTH: 120
<212> TYPE: PRT
<213> ORGANISM: Artificial Sequence
<220> FEATURE:
<223> OTHER INFORMATION: Synthetic

<400> SEQUENCE: 76

```
Ser Val Asn Asn Val Phe Phe Met Asn Val Ala Asn Asn Tyr Ser Lys
1               5                   10                  15

Leu Asn Lys Glu Glu Arg Glu Ile Glu Ile His Asn Ser Met Ala Ser
            20                  25                  30

Arg Tyr Tyr Ala Lys Thr Met Phe Ala Ala Phe Gln Met Leu Phe Ser
        35                  40                  45

Thr Met Leu Ser Asn Asn Val Asp Asn Leu Asp Lys Ala Tyr Gly Leu
    50                  55                  60

Ser Glu Asn Ile Gln Val Ala Thr Ser Thr Ser Ala Phe Leu Thr Phe
65                  70                  75                  80

Ala Tyr Val Tyr Asn Gly Ser Ile Met Asp Ser Val Thr Asn Ser Leu
                85                  90                  95

Leu Pro Pro Tyr Ala Lys Lys Pro Ile Thr Gln Leu Lys Tyr Gly Lys
```

```
                    100                 105                 110
Thr Phe Val Phe Ser Asn Tyr Phe
        115                 120

<210> SEQ ID NO 77
<211> LENGTH: 360
<212> TYPE: DNA
<213> ORGANISM: Artificial Sequence
<220> FEATURE:
<223> OTHER INFORMATION: Synthetic

<400> SEQUENCE: 77
agtgtgaata acgttttttt catgaatgtt gctaataatt attccaaatt aaacaaagaa     60
gaaagagaaa tcgaaataca taattccatg gcatcaagat attatgcaaa aacgatgttt    120
gcagcatttc aaatgttatt ttcaacaatg ttgagcaaca atgtagataa tcttgataaa    180
gcatatggat taagtgaaaa tatccaagta gcaacaagta cttccgcttt tcttactttt    240
gcatatgtat ataacggaag tataatggat agtgtgacta acagtttatt gccaccatat    300
gcgaagaaac ctataacaca attaaaatat ggaaaaacct tcgttttctc aaactatttc    360

<210> SEQ ID NO 78
<211> LENGTH: 1417
<212> TYPE: PRT
<213> ORGANISM: Artificial Sequence
<220> FEATURE:
<223> OTHER INFORMATION: Synthetic

<400> SEQUENCE: 78

Met Val Ser Phe Phe Lys Thr Pro Ile Phe Ile Leu Ile Ile Phe Leu
1               5                   10                  15

Tyr Leu Asn Glu Lys Val Ile Cys Ser Ile Asn Glu Asn Gln Asn Glu
            20                  25                  30

Asn Asp Thr Ile Ser Gln Asn Val Asn Gln His Glu Asn Ile Asn Gln
        35                  40                  45

Asn Val Asn Asp Asn Asp Asn Ile Glu Gln Leu Lys Ser Met Ile Gly
    50                  55                  60

Asn Asp Glu Leu His Lys Asn Leu Thr Ile Leu Glu Lys Leu Ile Leu
65                  70                  75                  80

Glu Ser Leu Glu Lys Asp Lys Leu Lys Tyr Pro Leu Leu Lys Gln Gly
                85                  90                  95

Thr Glu Gln Leu Ile Asp Ile Ser Lys Phe Asn Lys Asn Ile Thr
            100                 105                 110

Asp Ala Asp Asp Glu Thr Tyr Ile Ile Pro Thr Val Gln Ser Thr Phe
        115                 120                 125

His Asp Ile Val Lys Tyr Glu His Leu Ile Lys Glu Gln Ser Ile Glu
    130                 135                 140

Ile Tyr Asn Ser Asp Ile Ser Asp Lys Ile Lys Lys Ile Phe Ile
145                 150                 155                 160

Val Arg Thr Leu Lys Thr Ile Lys Leu Met Leu Ile Pro Leu Asn Ser
                165                 170                 175

Tyr Lys Gln Asn Asn Asp Leu Lys Ser Ala Leu Glu Glu Leu Asn Asn
            180                 185                 190

Val Phe Thr Asn Lys Glu Ala Gln Glu Glu Ser Ser Pro Ile Gly Asp
        195                 200                 205

His Gly Thr Phe Phe Arg Lys Leu Leu Thr His Val Arg Thr Ile Lys
    210                 215                 220
```

```
Glu Asn Glu Asp Ile Glu Asn Lys Gly Glu Thr Leu Ile Leu Gly Asp
225                 230                 235                 240

Asn Lys Ile Asp Val Met Asn Ser Asn Asp Phe Phe Thr Thr Asn
            245                 250                 255

Ser Asn Val Lys Phe Met Glu Asn Leu Asp Asp Ile Thr Asn Gln Tyr
            260                 265                 270

Gly Leu Gly Leu Ile Asn His Leu Gly Pro His Leu Ile Ala Leu Gly
            275                 280                 285

His Phe Thr Val Leu Lys Leu Ala Leu Lys Asn Tyr Lys Asn Tyr Phe
            290                 295                 300

Glu Ala Lys Ser Ile Lys Phe Phe Ser Trp Gln Lys Ile Leu Glu Phe
305                 310                 315                 320

Ser Met Ser Asp Arg Phe Lys Val Leu Asp Met Met Cys Asn His Glu
                325                 330                 335

Ser Val Tyr Tyr Ser Glu Lys Lys Arg Arg Lys Thr Tyr Leu Lys Val
            340                 345                 350

Asp Arg Ser Ser Thr Ser Met Glu Cys Asn Ile Leu Glu Tyr Leu Leu
            355                 360                 365

His Tyr Phe Asn Lys Tyr Gln Leu Glu Ile Ile Lys Thr Thr Gln Asp
            370                 375                 380

Thr Asp Phe Asp Leu His Gly Met Met Glu His Lys Tyr Ile Lys Asp
385                 390                 395                 400

Tyr Phe Phe Ser Phe Met Cys Asn Asp Pro Lys Glu Cys Ile Ile Tyr
                405                 410                 415

His Thr Asn Gln Phe Lys Lys Glu Ala Asn Glu Glu Asn Thr Phe Pro
            420                 425                 430

Glu Gln Glu Glu Pro Asn Arg Glu Ile Ser Ala Tyr Asn Leu Tyr Leu
            435                 440                 445

Asn Tyr Tyr Tyr Phe Met Lys Arg Tyr Ser Ser Tyr Gly Val Lys Lys
            450                 455                 460

Thr Leu Tyr Val His Leu Leu Asn Leu Thr Gly Leu Leu Asn Tyr Asp
465                 470                 475                 480

Thr Arg Ser Tyr Val Thr Ser Leu Tyr Leu Pro Gly Tyr Tyr Asn Ala
            485                 490                 495

Val Glu Met Ser Phe Thr Glu Glu Lys Glu Phe Ser Lys Leu Phe Glu
            500                 505                 510

Ser Leu Ile Gln Cys Ile Glu Lys Cys His Ser Asp Gln Ala Arg Gln
            515                 520                 525

Ile Ser Lys Asp Ser Asn Leu Leu Asn Asp Ile Thr Lys Cys Asp Leu
            530                 535                 540

Cys Lys Gly Ala Phe Leu Tyr Ser Asn Met Lys Phe Asp Glu Val Pro
545                 550                 555                 560

Ser Met Leu Gln Lys Phe Tyr Leu Tyr Leu Thr Lys Gly Leu Lys Ile
            565                 570                 575

Gln Lys Val Ser Ser Leu Ile Lys Thr Leu Asp Ile Tyr Gln Asp Tyr
            580                 585                 590

Ser Asn Phe Leu Ser His Asp Ile Asn Trp Tyr Thr Phe Leu Phe Leu
            595                 600                 605

Phe Arg Leu Thr Ser Phe Lys Glu Ile Ser Lys Lys Asn Val Ala Glu
            610                 615                 620

Ala Met Tyr Leu Asn Ile Lys Asp Glu Asp Thr Phe Asn Lys Thr Ile
625                 630                 635                 640

Val Thr Asn Tyr Trp Tyr Pro Ser Pro Ile Lys Lys Tyr Tyr Thr Leu
```

```
                     645                 650                 655
Tyr Val Arg Lys His Ile Pro Asn Asn Leu Val Asp Glu Leu Glu Lys
                660                 665                 670
Leu Met Lys Ser Gly Thr Leu Glu Lys Met Lys Lys Ser Leu Thr Phe
                675                 680                 685
Leu Val His Val Asn Ser Phe Leu Gln Leu Asp Phe Phe His Gln Leu
                690                 695                 700
Asn Glu Pro Pro Leu Gly Leu Pro Arg Ser Tyr Pro Leu Ser Leu Val
705                 710                 715                 720
Leu Glu His Lys Phe Lys Glu Trp Met Asp Ser Ser Pro Ala Gly Phe
                725                 730                 735
Tyr Phe Ser Asn Tyr Gln Asn Pro Tyr Ile Arg Lys Asp Leu His Asp
                740                 745                 750
Lys Val Leu Ser Gln Lys Phe Glu Pro Pro Lys Met Asn Gln Trp Asn
                755                 760                 765
Lys Val Leu Lys Ser Leu Ile Glu Cys Ala Tyr Asp Met Tyr Phe Glu
                770                 775                 780
Gln Arg His Val Lys Asn Leu Tyr Lys Tyr His Asn Ile Tyr Asn Ile
785                 790                 795                 800
Asn Asn Lys Leu Met Leu Met Arg Asp Ser Ile Asp Leu Tyr Lys Thr
                805                 810                 815
His Phe Asp Asp Val Leu Phe Phe Ala Asp Ile Phe Asn Met Arg Lys
                820                 825                 830
Tyr Met Thr Ala Thr Pro Val Tyr Lys Lys Val Lys Asp Arg Val Tyr
                835                 840                 845
His Thr Leu His Ser Ile Thr Gly Asn Ser Val Asn Phe Tyr Lys Tyr
                850                 855                 860
Gly Ile Ile Tyr Gly Phe Lys Val Asn Lys Glu Ile Leu Lys Glu Val
865                 870                 875                 880
Val Asp Glu Leu Tyr Ser Ile Tyr Asn Phe Asn Thr Asp Ile Phe Thr
                885                 890                 895
Asp Thr Ser Phe Leu Gln Thr Val Tyr Leu Leu Phe Arg Arg Ile Glu
                900                 905                 910
Glu Thr Tyr Arg Thr Gln Arg Arg Asp Asp Lys Ile Ser Val Asn Asn
                915                 920                 925
Val Phe Phe Met Asn Val Ala Asn Asn Tyr Ser Lys Leu Asn Lys Glu
                930                 935                 940
Glu Arg Glu Ile Glu Ile His Asn Ser Met Ala Ser Arg Tyr Tyr Ala
945                 950                 955                 960
Lys Thr Met Phe Ala Ala Phe Gln Met Leu Phe Ser Thr Met Leu Ser
                965                 970                 975
Asn Asn Val Asp Asn Leu Asp Lys Ala Tyr Gly Leu Ser Glu Asn Ile
                980                 985                 990
Gln Val Ala Thr Ser Thr Ser Ala Phe Leu Thr Phe Ala Tyr Val Tyr
                995                 1000                1005
Asn Gly Ser Ile Met Asp Ser Val Thr Asn Ser Leu Leu Pro Pro
                1010                1015                1020
Tyr Ala Lys Lys Pro Ile Thr Gln Leu Lys Tyr Gly Lys Thr Phe
                1025                1030                1035
Val Phe Ser Asn Tyr Phe Met Leu Ala Ser Lys Met Tyr Asp Met
                1040                1045                1050
Leu Asn Tyr Lys Asn Leu Ser Leu Leu Cys Glu Tyr Gln Ala Val
                1055                1060                1065
```

Ala Ser Ala Asn Phe Tyr Ser Ala Lys Val Gly Gln Phe Ile
1070            1075            1080

Gly Arg Lys Phe Leu Pro Ile Thr Thr Tyr Phe Leu Val Met Arg
1085            1090            1095

Ile Ser Trp Thr His Ala Phe Thr Thr Gly Gln His Leu Ile Ala
1100            1105            1110

Ala Phe Asn Pro Pro Thr Ser Thr Thr Asp Gly Lys Cys Ser Ala
1115            1120            1125

Pro Ser Tyr Lys Ser Pro Glu Ser Phe Phe Thr His Gly Leu
1130            1135            1140

Ala Ala Glu Ala Ser Lys Tyr Leu Phe Phe Tyr Phe Phe Thr Asn
1145            1150            1155

Leu Tyr Leu Asp Ala Tyr Lys Ser Phe Pro Gly Gly Phe Gly Pro
1160            1165            1170

Ala Ile Lys Glu Gln Thr Gln His Val Gln Gln Thr Tyr Glu
1175            1180            1185

Arg Lys Pro Ser Val His Ser Phe Asn Arg Asn Phe Met Glu
1190            1195            1200

Leu Val Asn Gly Phe Met Tyr Ala Phe Cys Phe Ala Ile Ser
1205            1210            1215

Gln Met Tyr Ala Tyr Phe Glu Asn Ile Asn Phe Tyr Ile Thr Ser
1220            1225            1230

Asn Phe Arg Phe Leu Asp Arg Tyr Tyr Gly Val Phe Asn Lys Tyr
1235            1240            1245

Phe Ile Asn Tyr Ala Ile Ile Lys Leu Lys Glu Ile Thr Ser Asp
1250            1255            1260

Leu Leu Ile Lys Tyr Glu Arg Glu Ala Tyr Leu Asn Met Lys Lys
1265            1270            1275

Tyr Gly Tyr Leu Gly Glu Val Ile Ala Ala Arg Leu Ser Pro Lys
1280            1285            1290

Asp Lys Ile Met Asn Tyr Leu His Glu Thr Asn Asp Asp Val Met
1295            1300            1305

Ser Asn Leu Arg Arg Tyr Asp Met Glu Asn Ala Phe Lys Asn Lys
1310            1315            1320

Met Val Thr Tyr Val Asp Asp Phe Ala Phe Phe Asp Asp Cys Gly
1325            1330            1335

Lys Asn Glu Gln Phe Leu Asn Glu Arg Cys Asp Tyr Cys Pro Val
1340            1345            1350

Ile Glu Glu Val Glu Glu Thr Glu Leu Phe Thr Thr Thr Gly Asp
1355            1360            1365

Lys Asn Thr Asn Glu Thr Thr Glu Ile Lys Lys Gln Thr Ser Thr
1370            1375            1380

Tyr Ile Asp Thr Glu Lys Met Asn Glu Ala Asp Ser Ala Asp Ser
1385            1390            1395

Asp Asp Glu Lys Asp Phe Asp Thr Pro Asp Asn Glu Leu Met Ile
1400            1405            1410

Ala Arg Phe His
1415

<210> SEQ ID NO 79
<211> LENGTH: 4251
<212> TYPE: DNA
<213> ORGANISM: Artificial Sequence
<220> FEATURE:

<223> OTHER INFORMATION: Synthetic

<400> SEQUENCE: 79

| | | | | | |
|---|---|---|---|---|---|
| atggtttcat | tttttaaaac | tccaatcttt | attttaatta | tcttttata | cttaaatgaa | 60 |
| aaggtaatat | gttcaataaa | tgaaaatcaa | aatgaaaatg | ataccattag | tcaaaatgtc | 120 |
| aaccaacatg | aaaatattaa | tcaaaatgta | aatgataatg | acaatattga | acaattaaaa | 180 |
| tccatgattg | gaaatgatga | actacataag | aatttaacaa | tattagaaaa | attaatttta | 240 |
| gagtctttag | aaaagataa | attaaaatat | cctctcctta | aacaaggaac | tgaacaattg | 300 |
| atagatatat | caaatttaa | taaaaaaat | attacagatg | cggatgatga | aacgtacatc | 360 |
| atacccaccg | tccaatcaac | gtttcacgat | attgtgaaat | acgaacatct | tataaaagaa | 420 |
| caatcaatag | aaatttacaa | ttctgatata | tcagataaaa | ttaagaaaaa | aattttata | 480 |
| gtaagaacat | tgaaaaccat | aaaattaatg | cttataccat | aaactcgta | caaacaaaat | 540 |
| aatgacttga | atctgcact | cgaagaatta | ataatgtat | ttacaaacaa | agaagctcaa | 600 |
| gaggaaagca | gtccaatagg | cgaccatggg | acattcttta | gaaaattgtt | aacacatgtt | 660 |
| agaacaatta | agaaaatga | agatatagaa | aataaaggag | aaacacttat | attaggcgat | 720 |
| aataaaatag | atgtaatgaa | ttcaaacgat | ttctttttta | caaccaactc | aaatgtaaaa | 780 |
| tttatggaaa | atttagatga | tataacaaat | caatatggat | taggtttgat | taatcatcta | 840 |
| ggtcctcatt | aatagcatt | gggtcatttt | accgtattaa | aattagcact | aaaaaattac | 900 |
| aaaaactatt | tgaagcaaa | aagtattaaa | tttttagtt | ggcaaaaaat | tttagagttc | 960 |
| tccatgtccg | atagatttaa | ggttcttgat | atgatgtgta | accatgaatc | tgtatattat | 1020 |
| tccgaaaaaa | aacgtagaaa | aacatattta | aaagttgaca | gatcaagcac | atcgatggaa | 1080 |
| tgtaatatat | tggaatattt | attacattat | tttaataaat | accaactaga | aataattaaa | 1140 |
| actacacaag | atactgattt | tgacttacat | ggtatgatgg | aacataaata | tataaaagat | 1200 |
| tatttctttt | catttatgtg | taatgatcct | aaggaatgta | ttatttatca | tacgaatcaa | 1260 |
| tttaaaaaag | aagccaacga | agaaaacaca | tttcctgaac | aagaagaacc | taatcgtgaa | 1320 |
| ataagtgcat | ataatttata | tttaaattat | tactatttca | tgaaacgtta | tagttcatat | 1380 |
| ggagtaaaaa | aaacattata | tgttcattta | ttaaatttaa | ctggactttt | aaattatgat | 1440 |
| acaagatctt | atgtgacatc | actttattta | ccaggatatt | acaacgctgt | cgaaatgtct | 1500 |
| tttacggaag | aaaaagagtt | ttccaaactt | tttgaaagct | aatacaatg | tattgaaaaa | 1560 |
| tgccattcag | accaagcaag | gcaaatatca | aaagatagta | atttacttaa | tgatataaca | 1620 |
| aaatgtgatt | tgtgtaaagg | agcattctta | tattctaaca | tgaaattcga | tgaagttcct | 1680 |
| tcaatgttgc | aaaaattta | cttatattta | actaaaggtc | tcaaaataca | aaagtatca | 1740 |
| tcactaatca | aaacgctaga | tatatatcaa | gattacagta | attttttatc | acatgatatt | 1800 |
| aattggtaca | cattcctatt | tttatttaga | cttacaagtt | ttaaagaaat | tcaaagaaa | 1860 |
| aatgttgctg | aagcaatgta | tttaaatata | aaagatgaag | atacgttcaa | caaaacgata | 1920 |
| gtaacaaaact | attggtaccc | atctcctata | aaaaaatatt | atacattata | cgttagaaaa | 1980 |
| cacataccaa | ataatttagt | agatgaattg | gagaaattaa | tgaaaagtgg | cacttagaa | 2040 |
| aaaatgaaaa | aatctctcac | cttttagta | catgtgaatt | cattttaca | attagatttt | 2100 |
| tttcatcaac | ttaatgaacc | acctcttgga | ttacctcgat | catatccttt | atccttagtt | 2160 |
| cttgaacata | aatttaaaga | atggatggac | agttcgcccg | ccggatttta | tttttcaaat | 2220 |
| tatcaaaatc | catatatcag | aaaagatttg | catgataaag | ttttatcaca | aaaatttgaa | 2280 |

```
ccacctaaaa tgaatcagtg gaacaaagtt ttgaagtcat taattgaatg cgcatatgat    2340
atgtattttg aacagagaca tgttaaaaat ttatataaat atcataacat ttataatata    2400
aataacaaat taatgttaat gagagattca attgatttat ataaaaccca ttttgacgac    2460
gtattatttt ttgcggatat atttaatatg agaaaatata tgacagctac accagtatat    2520
aaaaaagtaa aagacagagt gtaccataca ttgcatagta ttacaggaaa ttctgtcaat    2580
ttttataaat atggtattat atatggattt aaagtaaaca aagaaatatt aaagaagtt     2640
gtcgatgaat tgtattccat ctataatttt aacaccgaca tatttacgga tacttccttt    2700
ttacaaaccg tttatttatt atttagaaga atagaagaaa cttataggac ccaaagaaga    2760
gatgacaaaa taagtgtgaa taacgttttt ttcatgaatg ttgctaataa ttattccaaa    2820
ttaaacaaag aagaaagaga aatcgaaata cataattcca tggcatcaag atattatgca    2880
aaaacgatgt ttgcagcatt tcaaatgtta ttttcaacaa tgttgagcaa caatgtagat    2940
aatcttgata aagcatatgg attaagtgaa aatatccaag tagcaacaag tacttccgct    3000
tttcttactt ttgcatatgt atataacgga agtataatgg atagtgtgac taacagttta    3060
ttgccaccat atgcgaagaa acctataaca caattaaaat atggaaaaac cttcgttttc    3120
tcaaactatt tcatgctagc atccaaaatg tatgatatgt taaattataa aaatttaagt    3180
cttttatgtg aatatcaggc tgtggcaagt gccaatttct actctgctaa aaaggtaggt    3240
cagtttattg gaagaaaatt tttacccata actacatatt ttctagtaat gagaattagt    3300
tggacacatg cttttacaac tggacaacat ttgattgccg cttttaatcc cccaacttct    3360
actactgatg gtaaatgtag tgctcctagt tataaatccc ctgaaagttt tttctttact    3420
cacggacttg ctgctgaagc atccaaatat ttatttttt attttttcac aaatttatac    3480
cttgatgcct acaaatcttt tcctggagga tttggtcctg caataaaaga acaaactcaa    3540
catgttcaag aacaaacgta tgaacgcaaa ccatcagttc atagttttaa tagaaatttt    3600
ttcatggaac tcgtaaatgg attcatgtat gccttttgtt ttttgctat ttcacaaatg     3660
tatgcatatt ttgaaaatat taattttat attacaagta atttccgttt cttggataga    3720
tattatggtg tattcaataa atattttata aactatgcca taattaaact taagaaatt     3780
actagtgatc ttttaataaa atatgaacgt gaggcttatt taaatatgaa aaaatatggt    3840
tatttaggtg aagttattgc agctagactt tctcctaaag ataaaattat gaattatttg    3900
cacgaaacta acgacgatgt catgagtaat ttaagaagat atgatatgga aaatgctttc    3960
aaaaacaaaa tggttactta tgtggatgac tttgcttttt ttgatgattg tggcaaaaat    4020
gaacatttt taaatgaaag atgtgattat tgtcctgtaa ttgaagaggt ggaagaaaca     4080
gaattatta ctaccactgg tgataaaaac actaatgaga ccacggaaat aaaaaaacaa     4140
actagtacat atattgatac tgaaaaaatg aatgaggcgg attccgctga tagcgacgat    4200
gaaaaggatt ttgatactcc tgacaatgaa ttaatgatcg cacgatttca t             4251
```

PLASMODIAL SURFACE ANION CHANNEL INHIBITORS FOR THE TREATMENT OR PREVENTION OF MALARIA

CROSS-REFERENCE TO RELATED APPLICATION

This patent application is a divisional of U.S. patent application Ser. No. 15/072,902, which is a divisional of U.S. patent application Ser. No. 14/111,256, now U.S. Pat. No. 9,320,786, which is the U.S. National Phase of International Patent Application No. PCT/US2012/033072, filed Apr. 11, 2012, which claims the benefit of U.S. Provisional Patent Application No. 61/474,583, filed Apr. 12, 2011, each of which is incorporated by reference in its entirety herein.

STATEMENT REGARDING FEDERALLY SPONSORED RESEARCH AND DEVELOPMENT

This invention was made with Government support under project number ZIA AI000882-17 by the National Institutes of Health, National Institute of Allergy and Infectious Diseases. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 85,122 Byte ASCII (Text) file named "730842_ST25.txt," created Sep. 26, 2017.

BACKGROUND OF THE INVENTION

Malaria, one of the world's most important infectious diseases, is transmitted by mosquitoes and is caused by four species of *Plasmodium* parasites (*P. falciparum, P. vivax, P. ovale, P. malariae*). Symptoms include fever, chills, headache, muscle aches, tiredness, nausea and vomiting, diarrhea, anemia, and jaundice. Convulsions, coma, severe anemia and kidney failure can also occur. It remains a leading cause of death globally, especially amongst African children under 5 years of age. While repeated infections over many years leads to partial immunity in endemic areas, these adults still suffer significant morbidity and loss of productivity. The annual economic loss in Africa due to malaria is estimated at US $12 billion.

There is no effective vaccine currently available for malaria. Treatment has therefore relied primarily on antimalarial drugs such as chloroquine. Because some malaria parasites have acquired resistance to each available antimalarial drug, there is a desire to discover and develop new antimalarials.

BRIEF SUMMARY OF THE INVENTION

The invention provides methods of treating or preventing malaria comprising administering an effective amount of a compound of formula I to an animal. Methods of inhibiting a plasmodial surface anion channel of a parasite in an animal are also provided. The invention also provides pharmaceutical compositions comprising a compound represented by formula I in combination with one or more antimalarial compounds, e.g., those represented by formulas II, V, and VI. Use of the pharmaceutical compositions for treating or preventing malaria or for inhibiting a plasmodial surface anion channel in animals including humans are also provided. It is contemplated that the inventive compounds and/or pharmaceutical compositions inhibit a plasmodial surface anion channel and/or treat or prevent malaria by any number of mechanisms, for example, by inhibiting one or members of the parasite clag3 gene family. Embodiments of the inventive compounds have one or more advantages including, but not limited to: high affinity for the ion channel, high specificity for the ion channel, no or low cytoxicity, a chemical structure that is different from existing anti-materials, and drug-like features.

Also provided by the invention are clag3 amino acid sequences and related nucleic acids, vectors, host cells, populations of cells, antibodies, and pharmaceutical compositions. The invention also provides methods of treating or preventing malaria in an animal and methods of stimulating an immune response against a plasmodial surface anion channel of a parasite in an animal comprising administering to the animal an effective amount of the inventive clag3 amino acid sequences and related nucleic acids, vectors, host cells, populations of cells, antibodies, and pharmaceutical compositions.

BRIEF DESCRIPTION OF THE SEVERAL VIEWS OF THE DRAWING(S)

FIG. 1 is a graph showing sorbitol-induced osmotic lysis kinetics (% lysis) for the allelic exchange clone HB3$^{3rec}$ with indicated concentration of ISPA-28 ($\mu$M), a compound in accordance with an embodiment of the invention (see Formula A below), over time (minutes).

FIG. 2 is a graph showing mean±S.E.M. ISPA-28 dose ($\mu$M)-response (normalized P) for HB3$^{3rec}$ (circles). This dose response is intermediate between those of HB3 and Dd2 (top and bottom solid lines, respectively).

DETAILED DESCRIPTION OF THE INVENTION

Figure 1:
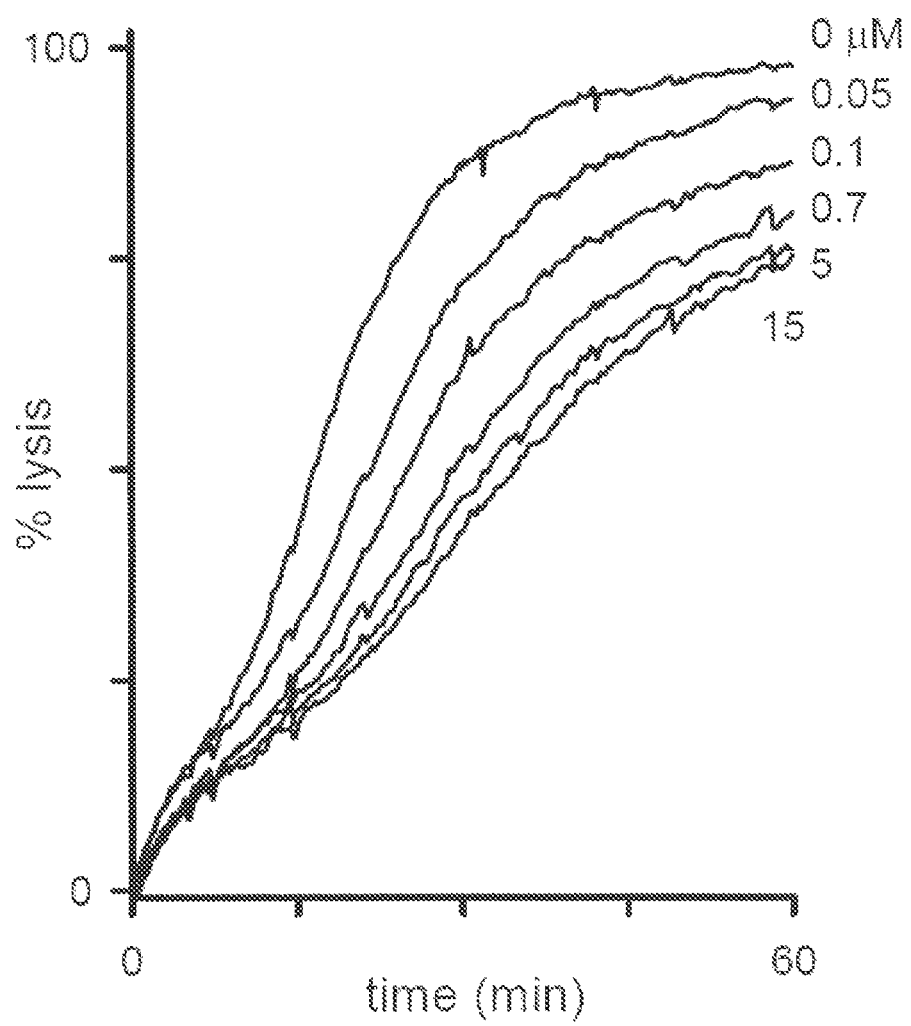

During its approximately 48 h cycle within the human red blood cell (RBC), *P. falciparum* must increase the red blood cell's (RBC's) permeability to a broad range of solutes. Electrophysiological studies identified the plasmodial surface anion channel (PSAC) as the molecular mechanism of these changes. PSAC's functional properties differ from those of known human ion channels. These properties include atypical gating, unique pharmacology, and an unmatched selectivity profile. An unusual property is PSAC's ability to exclude $Na^+$ by more than 100,000-fold relative to $Cl^-$ despite the channel's broad permeability to anions and bulky nutrients. This level of exclusion of a single small solute has not been reported in other broadly selective channels; it is essential for parasite survival because a higher $Na^+$ permeability would produce osmotic lysis of infected RBCS in the high $Na^+$ serum.

PSAC plays a central role in parasite nutrient acquisition. Sugars, amino acids, purines, vitamins, and precursors for phospholipid biosynthesis have markedly increased uptake into infected RBCs via PSAC. Many of these solutes have negligible permeability in uninfected RBCs and must be provided exogenously to sustain in vitro parasite growth. PSAC is conserved on divergent plasmodial species, as determined through studies of erythrocytes infected with rodent, avian, and primate malaria parasites. The channel's gating, voltage dependence, selectivity, and pharmacology are all conserved, suggesting that PSAC is a highly constrained integral membrane protein. Its surface location on the erythrocyte membrane offers conceptual advantages over parasite targets buried inside the infected RBC. PSAC's exposed location on infected RBCs forces direct access to antagonists in serum and excludes resistance via drug extrusion. In contrast, drugs acting within the parasite compartment must cross at least three membranous barriers to reach their target; clinical resistance to chloroquine and mefloquine appear to be linked to extrusion from their sites of action. Nearly all available PSAC antagonists inhibit in vitro parasite growth at concentrations modestly higher than those required for channel inhibition.

PSAC-inhibitor interactions may be determined by members of the clag3 plasmodia gene family. Clag3.1 (also known as RhopH1(3.1) and PFC0120w) and clag3.2 (also known as RhopH1(3.2) and PFC0110w) are members of the clag multigene family conserved in *P. falciparum* and *P. vivax*, Clag3.1 and clag3.2 are located on *P. falciparum* chromosome 3. The clag 3.1 gene sequence is referenced by Genbank Accession Nos. 124504714 and XM_001351064 (SEQ ID NO: 1). SEQ ID NO: 1 sets forth the mRNA sequence of the clag3.1 gene without the untranslated regions. The sequence of the protein product of the clag 3.1 gene (known as cytoadherence linked asexual protein 3.1) is referenced by Genbank Accession Nos. XP_001351100 and CAB10572.2 (SEQ ID NO: 2). The clag 3.2 gene sequence is referenced by Genbank Accession Nos. 124504712 and XM_001351063 (SEQ ID NO: 3). SEQ ID NO: 3 sets forth the mRNA sequence of the clag3.2 gene without the untranslated regions. The sequence of the protein product of the clag 3.2 gene (known as cytoadherence linked asexual protein 3.2) is referenced by Genbank Accession Nos. XP_001351099 and 124504713 (SEQ ID NO: 4). Based on available evidence, clag3.1 and clag3.2 encode the parasite PSAC.

The invention also provides a chimeric clag3.1/clag3.2 gene. SEQ ID NO: 79 sets forth the mRNA sequence of the chimeric clag3.1/clag3.2 gene without the untranslated regions, and SEQ ID NO: 78 sets forth the protein product of the chimeric clag3.1/clag3.2 gene. Amino acid residues 1-1011 of SEQ, ID NO: 78 correspond to amino acid residues 1-1011 of the clag3.1 protein SEQ ID NO: 2. Amino acid residues 1012-1417 of SEQ ID NO: 78 correspond to amino acid residues 1014-1416 of the clag3.2 protein SEQ ID NO: 4. Based on available evidence, the chimeric clag3.1/clag3.2 gene encodes a parasite PSAC.

Accordingly, the invention provides, in an embodiment, a method of treating or preventing malaria in an animal comprising administering an effective amount of a compound of formula (I) to the animal, preferably a human:

wherein:

Q is selected from the group consisting of a dioxo heterocyclyl ring fused to an aryl group, a heterocyclic amido group linked to a heterocyclic group, alkyl, a heterocyclic group fused to a heterocyclic amido group, arylamino carbonyl, amino, heterocyclic amido, and heterocyclic amino group, each of which, other than amino, is optionally substituted with one or more substituents selected from the group consisting of halo, hydroxy, mercapto, alkoxy, alkylthio, nitro, cyano, amino, alkyl, aryl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

Y is a bond, S, $SO_2$, or amido;

$R^1$ is divalent group selected from the group consisting of a heterocyclic ring having at least one nitrogen atom, piperidinyl, piperazinyl, aryl, a heterocyclic ring having at least one nitrogen atom linked to an alkylamino group, benzo fused heterocyclyl, heterocyclyl fused to an iminotetrahydropyrimidino group, and heterocyclyl fused to a heterocyclic amido group, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

$R^2$ is selected from the group consisting of arylalkenyl, heterocyclyl carbonylamino, heterocyclyl alkylamino, tetrahydroquinolinyl alkenyl, tetrahydroisoquinolinyl alkyl, indolylalkenyl, dihydroindolylalkenyl, aryl, aryloxyalkyl, arylalkyl, diazolyl, and quinolinylalkenyl, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

or a pharmaceutically acceptable salt thereof.

Another embodiment of the invention provides a method of inhibiting a plasmodial surface anion channel of a parasite in an animal comprising administering an effective amount of a compound of formula (I) to the animal, preferably a human:

or a pharmaceutically acceptable salt thereof, wherein Q, Y, $R^1$, and $R^2$ are as defined above.

Still another embodiment of the invention provides a compound of formula (I):

or a pharmaceutically acceptable salt thereof, wherein Q, Y, $R^1$, and $R^2$ are as defined above;

for use in treating or preventing malaria in an animal, preferably a human.

Yet another embodiment of the invention provides a compound of formula (I):

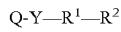 (I), or a pharmaceutically acceptable salt thereof, wherein Q, Y, $R^1$, and $R^2$ are as defined above;

for use in inhibiting a plasmodial surface anion channel of a parasite in an animal, preferably a human.

Still another embodiment of the invention provides a use of a compound of formula (I):

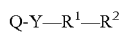 (I), or a pharmaceutically acceptable salt thereof, wherein Q, Y, $R^1$, and $R^2$ are as defined above;

in the manufacture of a medicament for treating or preventing malaria in an animal, preferably a human.

Yet another embodiment of the invention provides a use of a compound of formula (I):

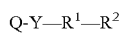 (I), or a pharmaceutically acceptable salt thereof, wherein Q, Y, $R^1$, and $R^2$ are as defined above;

in the manufacture of a medicament for inhibiting a plasmodial surface anion channel of a parasite in an animal, preferably a human.

In accordance with an embodiment of the invention, Q in formula I is selected from the group consisting of dioxotetrahydroquinoxalinyl, pyridazinyl heterocyclyl, alkyl, heterocyclyl pyridazinyl, and arylaminocarbonylalkyl, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxyalkyl, alkylcarbonyl, alkoxycarbonyl, aminocarbonyl, ureido, and formyl.

In accordance with an embodiment of the invention, $R^1$ in formula I is selected from the group consisting of piperidinyl, piperazinyl, piperidinylalkylamino, benzothiazolyl, thiozolyl fused to an imino tetrahydropyrimidino group, and thiazolyl fused to a pyridazone, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxyalkyl, alkylcarbonyl, alkoxycarbonyl, aminocarbonyl, ureido, and formyl.

In accordance with an embodiment of the invention, $R^2$ in formula I is selected from the group consisting of alkyl arylalkenyl, thiopheneylcarbonylamino, tetrahydro quinolinyl alkenyl, tetrahydro isoquinolinylalkyl, alkoxyaryl, aryl, aryloxyalkyl, and arylalkyl, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxyalkyl, alkylcarbonyl, alkoxycarbonyl, aminocarbonyl, ureido, and formyl.

In accordance with an embodiment of the invention, Y in formula I is $SO_2$. For example, Q in formula I is selected from the group consisting of (point of attachment is represented by a wiggly line here and elsewhere in the application):

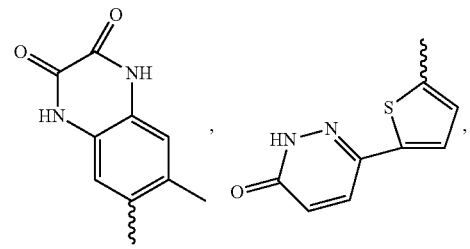

methyl, and isobutyl. In accordance with an embodiment of the invention, $R^1$ in formula I is selected from the group consisting of:

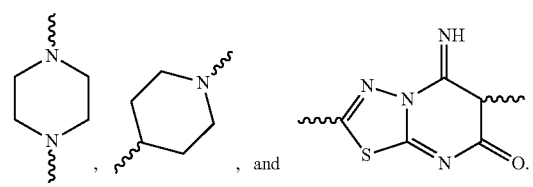

In accordance with an embodiment of the invention, $R^2$ is selected from the group consisting of:

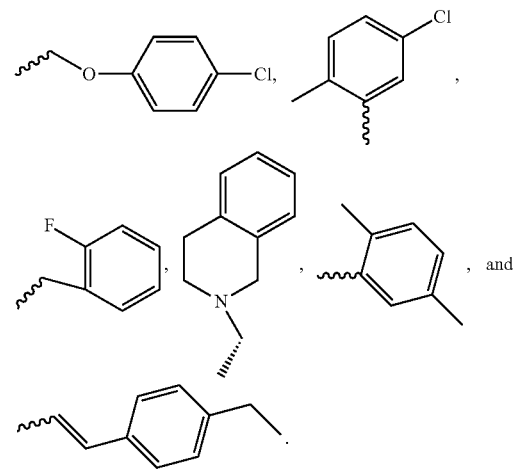

In accordance with any of the embodiments above, the compound of formula I is:

ISG-17

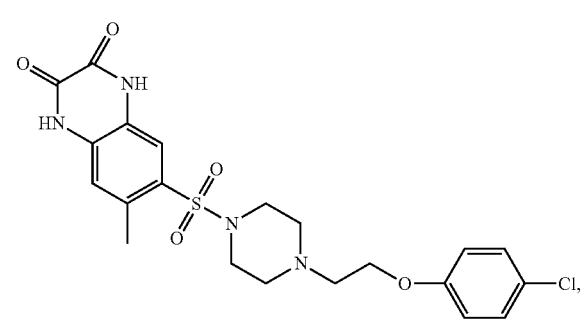

ISG-22
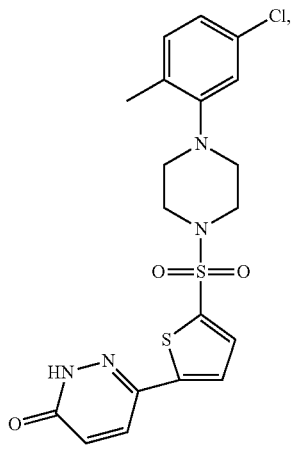
ISG-21
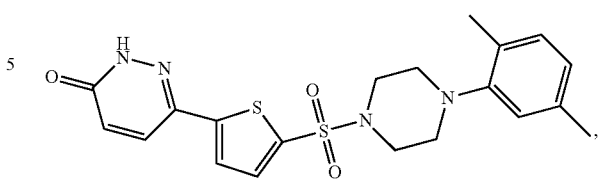
CD-008
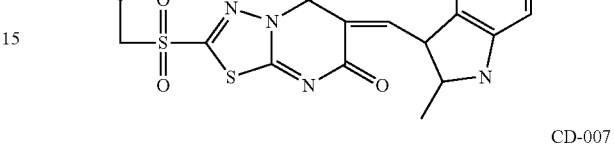
ISG-23
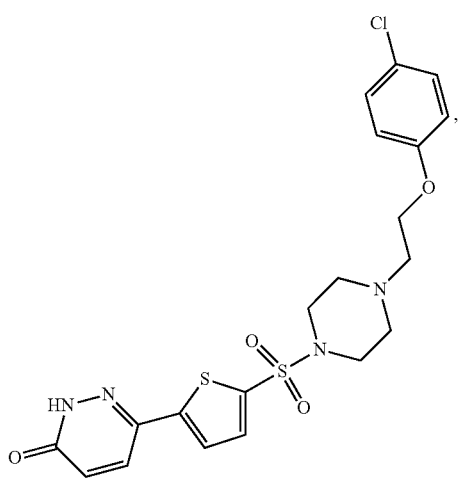
CD-007
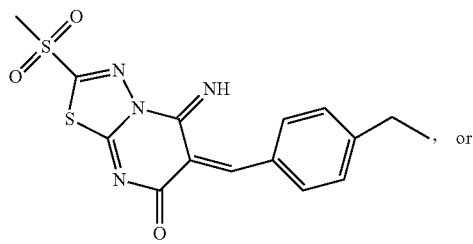
ISG-34
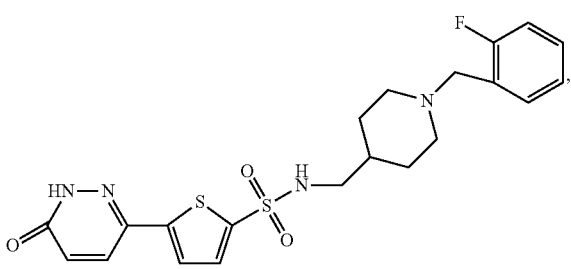
Cpd 50
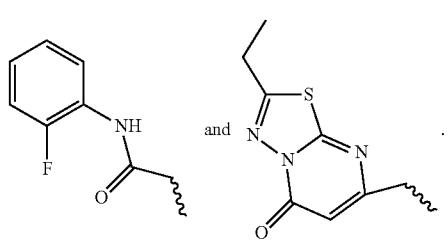
ISG-35
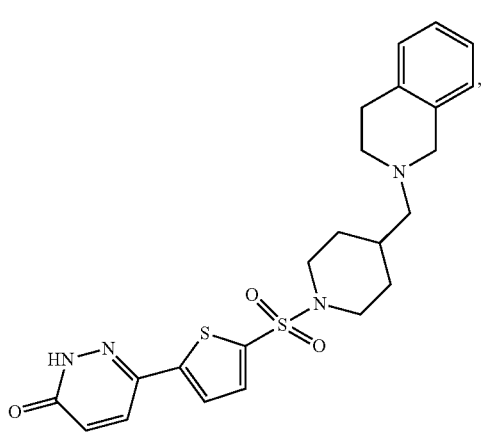
In accordance with an embodiment of the invention, Y in formula I is S. For example, in accordance with an embodiment of the invention, Q in formula I is selected from the group consisting of:
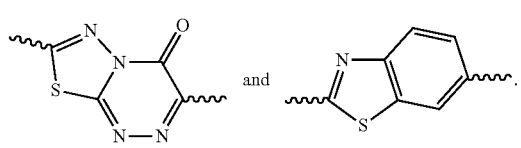
In accordance with an embodiment of the invention, $R^1$ in formula I is selected from the group consisting of:

In accordance with an embodiment of the invention, R² in formula I is selected from the group consisting of:

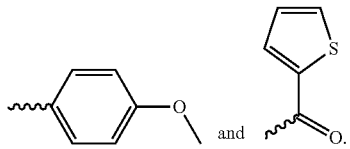

In accordance with an embodiment of the invention, the compound of formula I is:

ISG-28

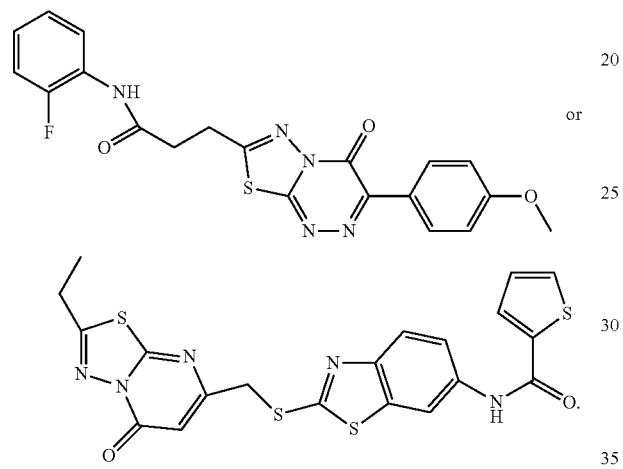

or

In accordance with an embodiment of the invention, Y of formula I is a bond. For example, in an embodiment of the invention, the compound of formula is:

CD-005

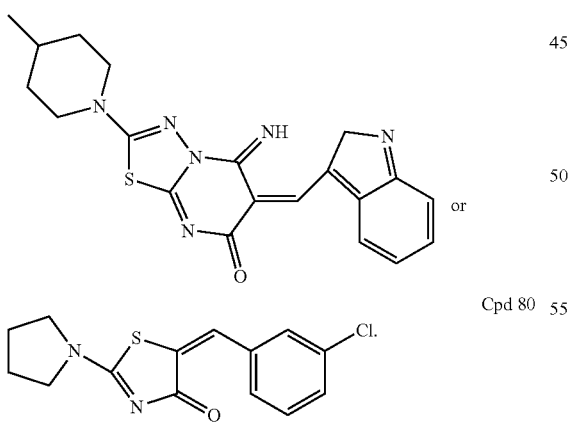

or

Cpd 80

In accordance with an embodiment of the invention, Y of formula (I) is amido. In accordance with an embodiment of the invention, Q is heterocyclic amido, R₁ is a heterocyclic ring having at least one nitrogen atom, and R₂ is diazolyl. For example, in an embodiment of the invention, the compound of formula I is:

ISPA-28

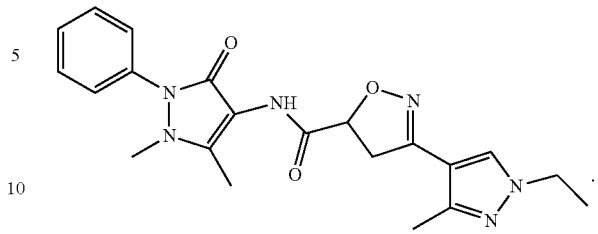

In an embodiment of the invention, the compound inhibits growth of P. falciparum Dd2.

Another embodiment of the invention provides a pharmaceutical composition comprising:

i) a compound of formula (I):

$$Q-Y-R^1-R^2 \quad (I),$$

wherein:

Q is selected from the group consisting of a dioxo heterocyclyl ring fused to an aryl group, a heterocyclic amido group linked to a heterocyclic group, alkyl, a heterocyclic group fused to a heterocyclic amido group, arylamino carbonyl, amino, heterocylic amido, and heterocyclic amino group, each of which, other than amino, is optionally substituted with one or more substituents selected from the group consisting of halo, hydroxy, mercapto, alkoxy, alkylthio, nitro, cyano, amino, alkyl, aryl, hydroxyalkyl, haloalkyl, cyanoalkyl, alkylamino, dialkylamino, carboxy, carboxyalkyl, alkylcarbonyl, alkoxycarbonyl, aminocarbonyl, ureido, and formyl;

Y is a bond, S, SO₂, or amido;

R¹ is divalent group selected from the group consisting of a heterocyclic ring having at least one nitrogen atom, piperidinyl, piperazinyl, aryl, a heterocyclic ring having at least one nitrogen atom linked to an alkylamino group, benzo fused heterocyclyl, heterocyclyl fused to an iminotetrahydropyrimidino group, and heterocyclyl fused to a heterocyclic amido group, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

R² is selected from the group consisting of arylalkenyl, heterocyclyl carbonylamino, heterocyclyl alkylamino, tetrahydroquinolinyl alkenyl, tetrahydroisoquinolinyl alkyl, indolylalkenyl, dihydroindolylalkenyl, aryl, aryloxyalkyl, arylalkyl, diazolyl, and quinolinylalkenyl, each of which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

or a pharmaceutically acceptable salt thereof; and ii) at least one other antimalarial compound.

The antimalarial compound may be any suitable antimalarial compound and may act by any mechanism and may, for example, inhibit a PSAC at any site. In an embodiment of the invention, the antimalarial compound is artemisinin, mefloquine, chloroquine, or derivatives thereof.

In an embodiment of the invention, the at least one other antimalarial compound is one or more compounds selected from the group consisting of:

a) a compound of formula II:

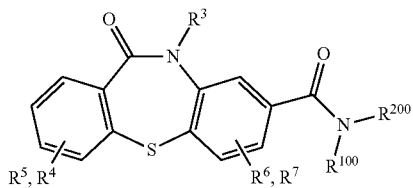

wherein $R^{100}$ is hydrogen or alkyl and $R^{200}$ is arylalkyl, optionally substituted on the aryl with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl, or $R^{200}$ is a group of formula (III):

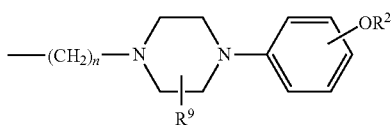

wherein n=0 to 6;

or $R^{100}$ and $R^{200}$ together with the N to which they are attached form a heterocycle of formula IV:

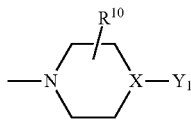

wherein X is N or CH; and $Y_1$ is aryl, alkylaryl, dialkylaryl, arylalkyl, alkoxyaryl, or heterocyclic, optionally substituted with one or more substituents selected from the group consisting of halo, hydroxyl, nitro, cyano, amino, aminoalkyl, alkylamino, alkylcarbonyl, alkoxycarbonyl, aminocarbonyl, and formyl; and $R^3$, $R^{10}$ are hydrogen or alkyl; or a pharmaceutically acceptable salt thereof;

(b) a compound of formula V:

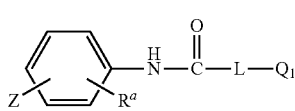

wherein

Z is a group having one or more 4-7 membered rings, wherein at least one of the rings has at least one heteroatom selected from the group consisting of O, S, and N, and when two or more 4-7 membered rings are present, the rings may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl;

$R^a$ is hydrogen, alkyl, or alkoxy;

L is a bond, alkyl, alkoxy, $(CH_2)_r$, or $(CH_2O)_s$, wherein r and s are independently 1 to 6;

$Q_1$ is a heterocycle group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl; and when L is alkyl or alkoxy, $Q_1$ is absent;

or a pharmaceutically acceptable salt thereof; and (c) a compound of formula VI:

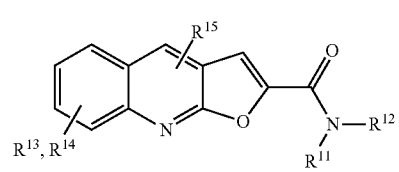

wherein $R^{11}$ and $R^{12}$ are independently hydrogen, alkyl, cycloalkyl, or aryl which is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl;

$R^{13}$-$R^{15}$ are independently selected from the group consisting of alkyl, halo, alkoxy, hydroxy, nitro, cyano, amino, alkylamino, aminoalkyl, alkylcarbonyl, alkoxycarbonyl, aminocarbonyl, and formyl;

or a pharmaceutically acceptable salt thereof. In this regard, in an embodiment of the invention, the pharmaceutical composition comprises at least one compound of formula I in combination with one or more compounds disclosed in U.S. Patent Application Publication No. 2011/0144086, which is a United States national stage application of PCT/US09/50637, filed on Jul. 15, 2009, and which published as WO 2010/011537, each of which are incorporated herein by reference.

In accordance with an embodiment of the invention, the pharmaceutical composition comprises a compound of formula I and any one or more of

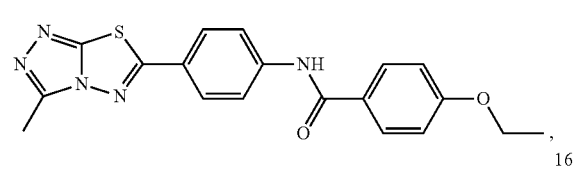

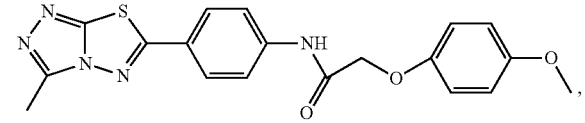

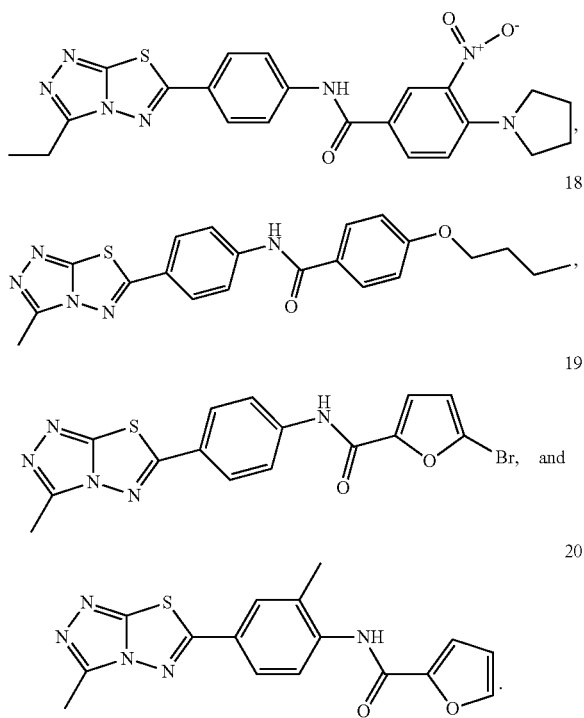

Another embodiment of the invention provides a method of treating or preventing malaria in an animal comprising administering to the animal an effective amount of a compound of formula I and at least one other antimalarial compound. In an embodiment, the at least one other antimalarial compound is one or more compound(s) selected from the group consisting of a compound of formula II, a compound of formula V, and a compound of formula VI.

Still another embodiment of the invention provides a method of inhibiting a plasmodial surface anion channel of a parasite in an animal comprising administering to the animal an effective amount of a compound of formula I and one or more compound(s) selected from the group consisting of a compound of formula II, a compound of formula V, and a compound of formula VI.

Referring now to terminology used generically herein, the term "alkyl" implies a straight or branched alkyl moiety containing from, for example, 1 to 12 carbon atoms, preferably from 1 to 8 carbon atoms, more preferably from 1 to 6 carbon atoms. Examples of such moieties include methyl, ethyl, propyl, isopropyl, n-butyl, sec-butyl, isobutyl, tert-butyl, pentyl, isoamyl, hexyl, octyl, dodecanyl, and the like.

The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2 π electrons, according to Hückel's Rule, wherein a n=1, 2, or 3.

The term "heterocyclic" means a cyclic moiety having one or more heteroatoms selected from nitrogen, sulfur, and/or oxygen. Preferably, a heterocyclic is a 5 or 6-membered monocyclic ring and contains one, two, or three heteroatoms selected from nitrogen, oxygen, and/or sulfur. Examples of such heterocyclic rings are pyrrolinyl, pyranyl, piperidyl, tetrahydrofuranyl, tetrahydrothiopheneyl, and morpholinyl.

The term "alkoxy" embraces linear or branched alkyl groups that are attached to a an ether oxygen. The alkyl group is the same as described herein. Examples of such substituents include methoxy, ethoxy, t-butoxy, and the like.

The term "halo" as used herein, means a substituent selected from Group VIIA, such as, for example, fluorine, bromine, chlorine, and iodine.

For the purpose of the present invention, the term "fused" includes a polycyclic compound in which one ring contains one or more atoms preferably one, two, or three atoms in common with one or more other rings.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In accordance with an embodiment of the invention, $R^3$ in formula II is hydrogen. In accordance with the above embodiments, $R^4$-$R^7$ in formula II are hydrogen. In an example, $R^{100}$ in formula II is hydrogen and $R^{200}$ is a group of formula III, wherein n=1 to 6, preferably n=2 to 4.

In accordance with an embodiment of the invention, wherein $R^{100}$ and $R^{200}$ together with the N to which they are attached form a heterocycle of formula IV. For example, X in formula IV is N. In accordance with the invention, in formula IV, $Y_1$ is aryl which is optionally substituted with one or more substituents selected from the group consisting of halo, hydroxyl, nitro, cyano, amino, alkyl, alkoxy, aminoalkyl, alkylamino, alkylcarbonyl, alkoxycarbonyl, aminocarbonyl, and formyl. For example, in formula IV, $Y_1$ is phenyl, which is optionally substituted with one or more substituents selected from the group consisting of halo, hydroxyl, nitro, cyano, amino, allyl, alkoxy, aminoalkyl, alkylamino, alkylcarbonyl, alkoxycarbonyl, aminocarbonyl, and formyl, specifically, $Y_1$ is phenyl or phenyl substituted with one or more substituents selected from the group consisting of methyl, chloro, fluoro, and methoxy.

In accordance with any of the embodiments above, the compound of formula II is:

1
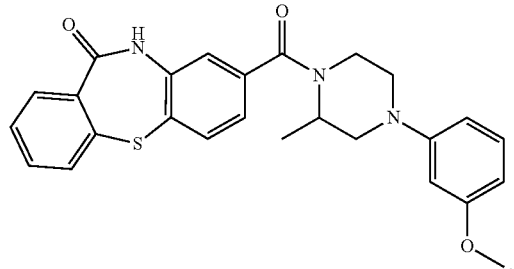

2
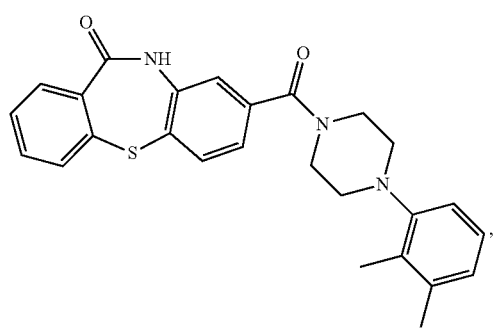

3
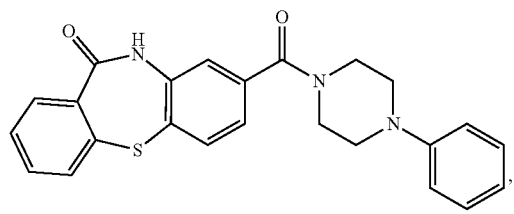

4
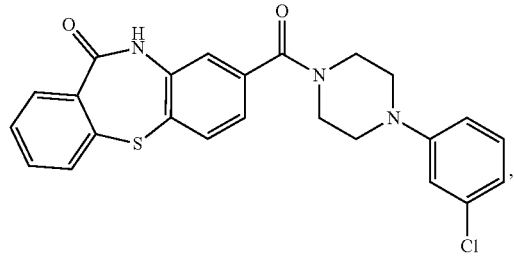

5
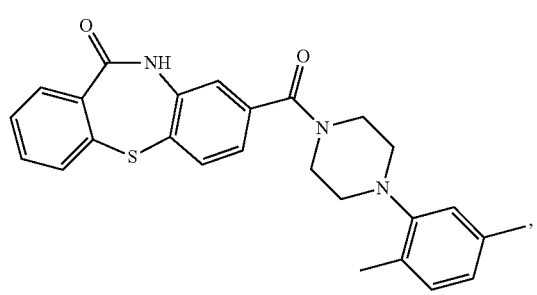

-continued

31
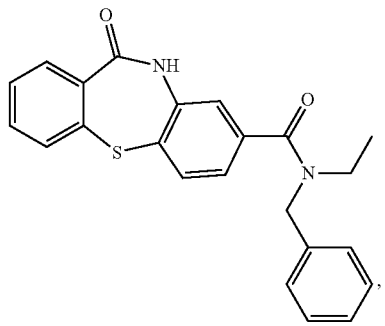

6
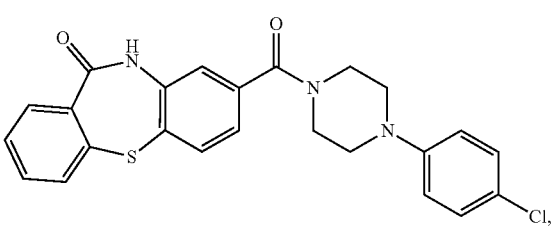

7
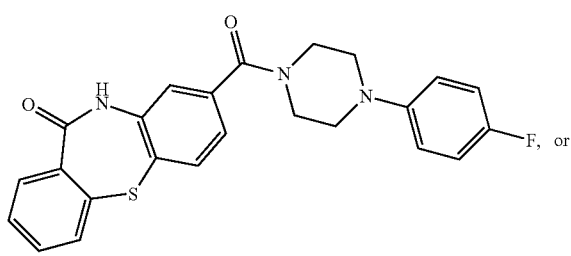

8
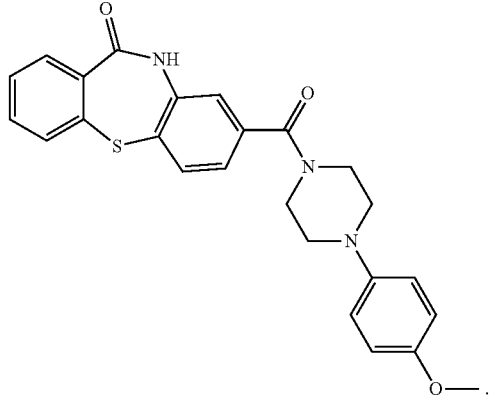

In accordance with another embodiment of the invention, X in formula IV is CH. In a particular embodiment, $Y_1$ is arylalkyl or heterocyclic, which is optionally substituted with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl. Illustratively, $Y_1$ is benzyl or piperidinyl, which is optionally substituted with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl. Examples of specific compounds of formula II are:

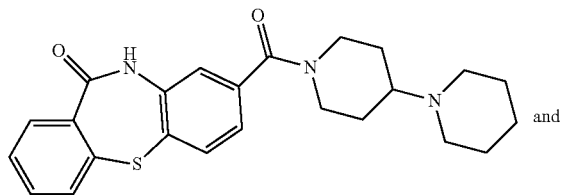

and

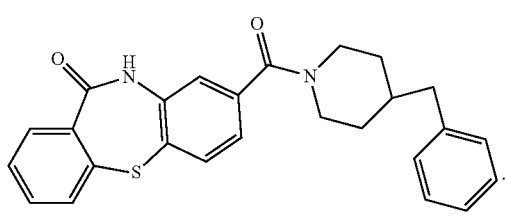

In another embodiment of the invention, $R^{100}$ in formula II is hydrogen and $R^{200}$ is arylalkyl, optionally substituted on the aryl with a substituent selected from the group consisting of halo, hydroxyl, nitro, cyano, amino, alkyl, aminoalkyl, alkylamino, alkylcarbonyl, and formyl. As an example, $R^{200}$ is arylalkyl, phenylalkyl such as phenyl butyl. A specific example of such a compound of formula II is:

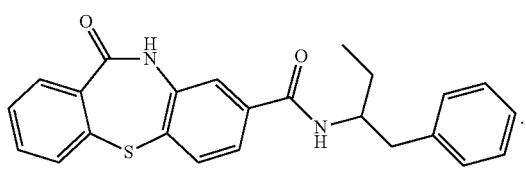

In accordance with an embodiment of the invention, a specific example of a compound of formula III is:

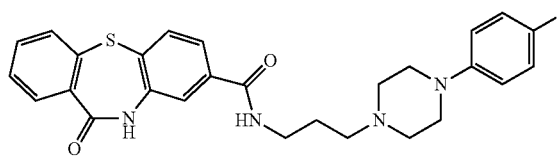

In accordance with another embodiment of the invention, in the compound of formula V, L is a bond or $(CH_2O)_s$, and $Q_1$ is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl.

In accordance with an embodiment, wherein Z is a group having one or more 4-7 membered rings, wherein at least one of the rings has at least one heteroatom selected from the group consisting of O, S, and N; and when two or more 4-7 membered rings are present, they may be fused or unfused; wherein the rings are optionally substituted with one or more substituents selected from the group consisting of halo, hydroxy, alkoxy, nitro, cyano, amino, aminoalkyl, alkylamino, alkylcarbonyl, alkoxycarbonyl, aminocarbonyl, and formyl.

In the above embodiment, Z is a group having one or two 4-7 membered rings, wherein at least one of the rings has at least one heteroatom selected from the group consisting of O, S, and N; and when two 4-7 membered rings are present, they may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl.

In a specific embodiment of the formula V, $Q_1$ is an aryl group, optionally substituted with an alkoxy group or $Q_1$ is a heterocyclic group which is saturated or unsaturated. For example, $Q_1$ is aryl such as phenyl or naphthyl.

Examples of compounds of formula IV are:

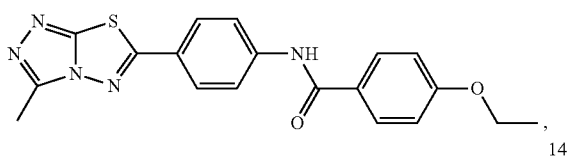

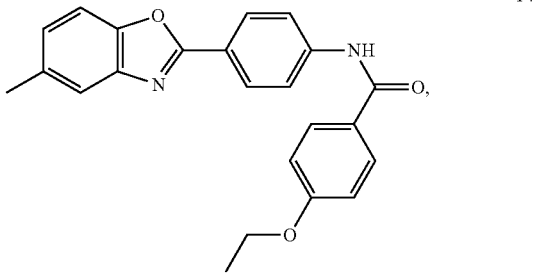

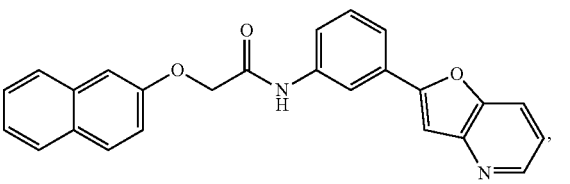

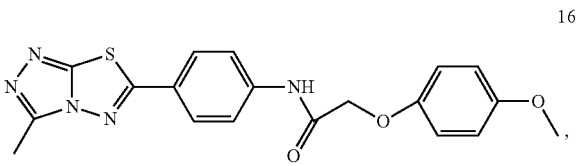

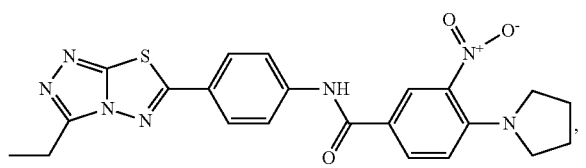

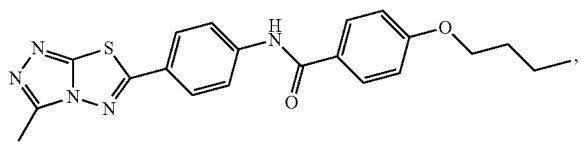

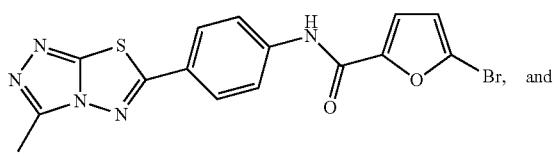

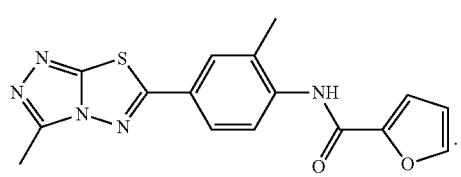

In accordance with an embodiment of the invention, in the compound of formula V, $Q_1$ is a heteroaromatic group, e.g., pyridyl. An example of such a compound is:

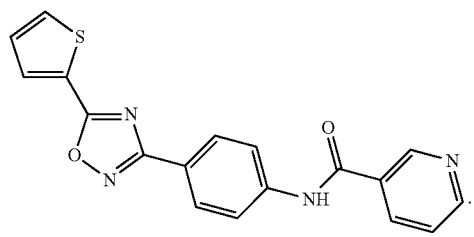

In accordance with another embodiment of the invention, in the compound of formula V, L is an alkyl group and $Q_1$ is absent. Examples of such compounds are:

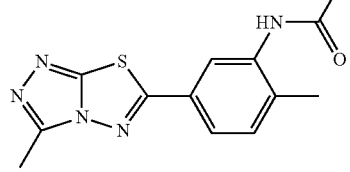

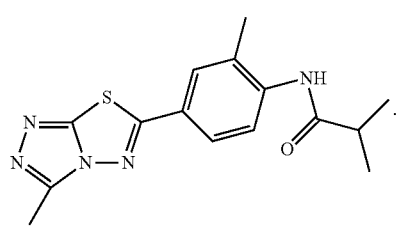

In accordance with another embodiment of the invention, in the compound of formula VI, $R^{13}$ is alkyl or alkoxy and $R^{14}$ and $R^{15}$ are hydrogen. In a particular embodiment, $R^{13}$ is methyl or methoxy.

In the above embodiments of the compound of formula VI, specifically, $R^{11}$ is alkyl and $R^{12}$ is alkyl, cycloalkyl, or aryl, wherein said aryl is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl. In a particular embodiment, $R^{12}$ is alkyl, cycloalkyl, or aryl, wherein said aryl is optionally substituted with one or more alkyl and/or alkoxy substituents.

Examples of compounds of formula VI are:

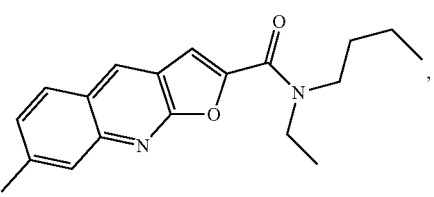

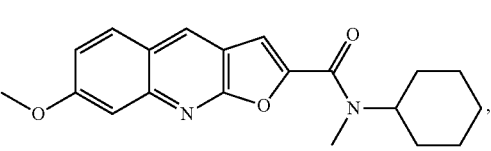

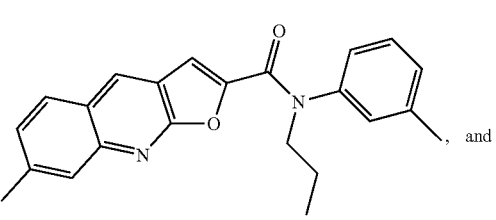

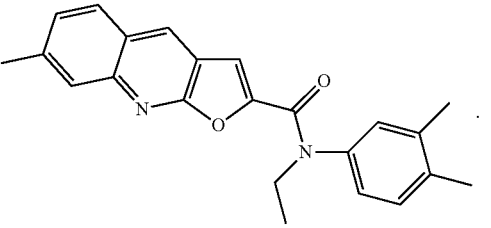

In accordance with an embodiment of the invention, in compound of formula VI, $R^{11}$ is hydrogen and $R^{12}$ is cycloalkyl or aryl, which is optionally substituted with one or more alkyl and/or alkoxy substituents. Exemplary compounds of formula VI are:

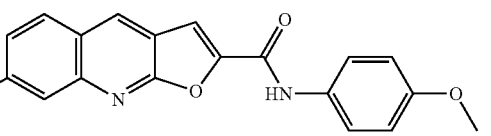

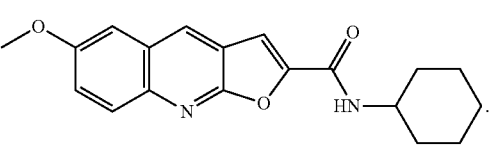

In accordance with the invention, an effective amount of a compound of formula I is administered in combination with any one or more compound(s) of formulas II, V, and VI, for example, a combination of compounds of formulas I and II, compounds of formulas I and V, compounds of formulas I and VI, compounds of formulas I, II and V, compounds of formulas I, II and VI, compounds of formulas I, V and VI, or compounds of formulas I, II, V, and VI, or pharmaceutically acceptable salts thereof, is administered. It is contemplated that such combinations provide synergy-enhanced of the parasite, when a combination of two or more compounds are employed. The extent of killing is greater than the sum of the individual killings.

The compounds of the invention can be prepared by suitable methods as would be known to those skilled in the art or obtained from commercial sources such as ChemDiv Inc., San Diego, Calif. or Peakdale Molecular Limited, High Peak, England. See also WO 00/27851 and U.S. Pat. Nos. 6,602,865 and 2,895,956.

Another embodiment of the invention provides a clag3 amino acid sequence comprising, consisting of, or consisting essentially of SEQ ID NO: 62, 64, 66, 72, 74, or 76, with the proviso that the amino acid sequence is not SEQ ID NO: 2, 4, or 78. SEQ ID NOs: 62, 64, 66, 74, and 76 correspond to amino acid residues 1063-1208, 1232-1417, 25-332, 488-907, and 925-1044 of the clag3.1 protein of the 3D7 parasite line, SEQ ID NO: 72 corresponds to amino acid residues 1063-1244 of the clag3.1 protein of the Dd2 parasite line. SEQ ID NOs: 62, 64, 66, 72, 74, and 76 are encoded by nucleotide sequence SEQ ID NOs: 63, 65, 67, 73, 75, and 77, respectively.

In this regard, an embodiment of the invention provides a clag3 amino acid sequence comprising, consisting of, or consisting essentially of SEQ ID NO: 62, 64, 66, 72, 74, or 76, with the proviso that the amino acid sequence is not SEQ ID NO: 2, 4, or 78.

Another embodiment of the invention provides a nucleic acid comprising a nucleotide sequence encoding the inventive amino acid sequences, with the proviso that the nucleotide sequence is not SEQ ID NO: 1, 3, or 79. For example, the nucleotide sequence comprises, consists, or consists essentially of SEQ ID NO: 63, 65, 67, 73, 75, or 77.

Further embodiments of the invention provide a recombinant expression vector comprising an inventive nucleic acid, an isolated host cell comprising the inventive recombinant expression vector, a population of cells comprising the inventive host cell, and an antibody, or antigen binding portion thereof, which specifically binds to an inventive amino acid sequence. The inventive amino acid sequence, nucleic acid, recombinant expression vector, host cell, population of cells, and/or antibody, or antigen binding portion thereof may be isolated or purified.

Still another embodiment of the invention provides a pharmaceutical composition comprising the inventive amino acid sequence, nucleic acid, recombinant expression vector, host cell, population of cells, and/or antibody, or antigen binding portion thereof, and a pharmaceutically acceptable carrier.

Yet another embodiment of the invention provides a method of treating or preventing malaria in an animal comprising administering to the animal an effective amount of the inventive amino acid sequence, nucleic acid, recombinant expression vector, host cell, population of cells, antibody, or antigen binding portion thereof, and/or pharmaceutical composition.

Yet another embodiment of the invention provides a method of stimulating an immune response against a plasmodial surface anion channel of a parasite in an animal comprising administering to the animal an effective amount of the inventive amino acid sequence, nucleic acid, recombinant expression vector, host cell, population of cells, antibody, or antigen binding portion thereof, and/or pharmaceutical composition. In an embodiment, stimulating an immune response comprises stimulating the production of antibodies that specifically bind to the plasmodial surface anion channel.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Infectable Drugs*, Toisael, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable carriers and their formulations are further described in A. R., Gennaro, ed., *Remington: The Science and Practice of Pharmacy* (19th ed.), Mack Publishing Company, Easton, Pa. (1995).

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The amount or dose of a compound of the invention or a salt thereof, or a composition thereof should be sufficient to affect a therapeutic or prophylactic response in the mammal. The appropriate dose will depend upon several factors. For instance, the dose also will be determined by the existence, nature and extent of any adverse side effects that might accompany the administration of a particular compound or salt. Ultimately, the attending physician will decide the dosage of the compound of the present invention with which to treat each individual patient, taking into consideration a variety of factors, such as age, body weight, general health, diet, sex, compound or salt to be administered, route of administration, and the severity of the condition being treated. By way of example and not intending to limit the invention, the dose of the compound(s) described herein can be about 0.1 mg to about 1 g daily, for example, about 5 mg to about 500 mg daily. Further examples of doses include but are not limited to: 0.1 mg, 0.15 mg, 0.2 mg, 0.25 mg, 0.5 mg, 0.6 mg, 0.75 mg, 1 mg, 1.5 mg, 2 mg, 3 mg, 4 mg, 5 mg, 6 mg, 7 mg, 8 mg, 9 mg, 10 mg, 12 mg, 15 mg, 17 mg, 20 mg, 25 mg, 30 mg, 35 mg, 40 mg, 45 mg, 50 mg, 55 mg, 60 mg, 70 mg, 75 mg, 80 mg, 85 mg, 90 mg, 95 mg, 100 mg, 125 mg, 140 mg, 150 mg, 175 mg, 200 mg, 225 mg, 250 mg, 300 mg, 350 mg, 400 mg, 450 mg, 500 mg, 550 mg, 600 mg, 650 mg, 700 mg, 750 mg, 810 mg, 850 mg, 900 mg, 950 mg, or 1000 mg/kg body weight per day.

The following examples further illustrate the invention but, of course, should not be construed as in any way limiting its scope.

EXAMPLES

Osmotic Lysis Experiments and High-Throughput Inhibitor Screen

Laboratory lines of *P. falciparum* were cultured by standard methods, enriched at the trophozoite stage using the Percoll-sorbitol method, washed, and resuspended at 25° C. and 0.15% hematocrit in 280 nM sorbitol, 20 nM Na-HEPES, 0.1 mg/ml BSA, pH 7.4 with indicated concentrations of inhibitors; uptake of proline, alanine, and phenyl-trimethylammonium chloride (PhTMA-Cl) was similarly measured after iso-osmotic replacement for sorbitol. Osmotic swelling and lysis were continuously tracked by recording transmittance of 700-nm light through the cell suspension (DU640 spectrophotometer with Peltier temperature control, Beckman Coulter). Recordings were normalized to 100% osmotic lysis of infected cells at the transmittance plateau. Inhibitor dose responses were calculated by interpolation of the time required to reach fractional lysis thresholds. Dose responses were fitted to the sum of two Langmuir isotherms:

$$P=a/(1+(x/b))+(1-a)/(1+(x/c)) \quad \text{(Eq. S1)}$$

where P represents the normalized solute permeability in the presence of inhibitor at concentration x, and a, b, and c are constants.

High-throughput screens using this transmittance assay were performed identically with HB3- and Dd2-infected cells at room temperature using a commercial library of 50,000 compounds with >90% purity confirmed by NMR (ChemDiv). Screens were performed in 384-well format with individual wells containing a single compound at 10 µM final concentration. Each microplate had two types of controls, 32 positive control wells received PBS instead of sorbitol; erythrocytes in these wells do not lyse because PSAC has low $Na^+$ permeability. 32 negative control wells received sorbitol with DMSO but no test compound. Readings were taken at multiple timepoints to permit estimation of inhibitor affinity in a high-throughput format. The purity and molecular weight of ISPA-28 were confirmed by mass spectrometry.

The activity of each screening compound was calculated based on readings at the 2 h timepoint according to:

$$\% B=100*(A_{cpd}-\bar{A}_{neg})/(\bar{A}_{pos}-\bar{A}_{neg}) \quad \text{(Eq. S2)}$$

where % B is the normalized channel block and $A_{cpd}$ represents the absorbance from a well containing a test compound. $A_{neg}$ $A_{pos}$ represent the mean absorbances of in-plate negative and positive control wells. % B is a quantitative measure of inhibitor activity.

Inhibitors having significantly differing efficacies against uptake by HB3- and Dd2-infected cells were selected using a weighted difference statistic (WDS), determined from % B values at the 2 h timepoint according to:

$$WDS=|\% B_{HB3}-\% B_{Dd2}|/(3*\sigma_{pos}) \quad \text{(Eq. S3)}$$

where $\sigma_{pos}$ is the standard deviation of in-plate positive control wells. Isolate-specific inhibitors have WDS≥1.0; larger values correspond to greater differences in efficacy against uptake by the two screened parasite lines. Analysis and data mining of the screens were automated using locally developed code (DIAdem 10.2 and DataFinder, National Instruments).

Electrophysiology

Recordings were obtained with quartz patch pipettes (1-3 MΩ) and symmetric bath and pipette solutions of 1,000 mM choline chloride, 115 mM NaCl, 10 mM $MgCl_2$, 5 mM $CaCl_2$, 20 mM Na-HEPES, pH 7.4. Where present, ISPA-28 was added to both bath and pipette compartments. Seal resistances were >100 GΩ. Recordings were obtained at imposed membrane potentials of −100 mV, applied as steps from a holding potential of 0 mV, using an Axopatch 200B amplifier (Molecular Devices), low-pass filtered at 5 kHz (8-pole Bessel, Frequency Devices), digitized at 100 kHz, and recorded with Clampex 9.0 software (Molecular Devices).

Single channel open probabilities and gating analyses were determined using locally developed code (DIAdem 8.1, National Instruments). The code for tallying closed channel durations was applied to recordings obtained as voltage steps of 10 s duration to preserve seal integrity. It detects mid-threshold crossings, uses linear interpolation of adjacent sample times, and corrects for a Gaussian filter risetime of 66.4 µs as described in detail previously (Desai et al., *Nanomedicine*, 1: 58-66 (2005)). Durations were tallied into 16 bins/decade, normalized to percent of the total number of events, and displayed on square root plots, where time constants for simple exponentially decaying processes are visible as maxima (Sigworth et al, *Biophys. J.* 52: 1047-54 (1987)).

Quantitative Trait Locus (QTL) Analysis of ISPA-28 Efficacies

A distinct collection of 443 polymorphic microsatellite markers were selected that distinguish the Dd2 and HB3 parental lines (Su et al., *Science*, 286: 1351-53 (1999)). 5 additional single nucleotide polymorphisms within the chromosome 3 locus were identified by DNA sequencing and were used to genotype progeny clones. This genotype data was used to search for genetic loci associated with ISPA-28 efficacy in the genetic cross progeny by performing QTL analysis with R/qtl software (available at http://www.rqtl.org/) as described (Broman et al., *Bioinformatics*, 19: 889-90 (2003)). Because *P. falciparum* asexual stages are haploid, the analysis was analogous to that for recombinant inbred genetic crosses. Significance thresholds at the P=0.05 level were determined by permutation analysis. A secondary scan to search for additional QTL was carried out by controlling for the primary chromosome 3 locus as described in the R/qtl software package.

PiggyBac Transposase-Mediated Complementation

Individual candidate genes and a conserved open reading frame within the mapped locus were evaluated using piggyBac transposase-mediated complementation (Balu et al. *PNAS*, 102: 16391-96 (2005)). Each candidate, along with its presumed endogenous 5' promoter region (1-2 kb upstream of the start ATG) and 3'UTR (0.5 kb downstream from the stop codon), was PCR amplified from HB3 genomic DNA with primers listed below in Table 1, and inserted into the multiple cloning site of the pXL-BacII-DHFR vector; ligation places the insert adjacent to the human dihydrofolate reductase gene (hDHFR), whose product permits selection by the antifolate WR99210. This integration cassette is flanked by two inverted terminal repeats (ITR) that are recognized by piggyBac. Transgene-bearing plasmids were cotransfected into Dd2 with pHTH, a helper plasmid that encodes the transposase but lacks a selectable marker. Expression of the transposase facilitates genomic integration of the transgene and hDHFR.

Dye-terminator sequencing of cDNA was used to confirm transgene expression based ore detection of known polymorphic sites as doublet peaks in sequence chromatograms. Briefly, cDNA was generated by reverse transcription from total RNA with SuperScriptIII kit (Invitrogen) according to manufacturer instructions. Specific transcripts were then amplified with gene-specific primers. HB3 alleles noted as not expressed were either not detected by this method or not examined due to the lack of polymorphism between Dd2 and HB3.

TABLE 1

| gene | Forward primer sequence | Reverse primer sequence |
|---|---|---|
| PFC0075C | ATACCGTCGACTTGTCAATTTTTATGTTTGCATAAACG (SEQ ID NO: 5) | AATTAGGTACCGTACAAATAAATACAATATTTTTCATAGCAA (SEQ ID NO: 6) |
| PFC0080C | TATCCGTCGACTCTATTTACACTCATGAAGACAGAGGTAA (SEQ ID NO: 7) | AATTAGGTACCCTTCATTGAAAATTTTACAAGGGTATC (SEQ ID NO: 8) |
| PFC0085C | ATACCGTCGACTATGAATGATTGTACTACTTTTGTAAGAAT (SEQ ID NO: 9) | AATATGGTACCTACACATTGACATAGGGTATCATCATT (SEQ ID NO: 10) |
| PFC0090W | ATACCGTCGACCCTTTTTACACGTATATTCGGACAATC (SEQ ID NO: 11) | AATTAGGTACCGTTAACCGTTAACACGAACAATTTTGCAGTATG (SEQ ID NO: 12) |
| PFC0095C | ATACCGTCGACCAAAAAACCGAAATGGCATTTC (SEQ ID NO: 13) | AATTAGGTACCATGAAATATGTAATACGTGGGTTAAAAG (SEQ ID NO: 14) |
| PFC0100C | ATACCGTCGACTTCCATGTTTAAAGTGAAATTAGAAGATAT (SEQ ID NO: 15) | AATTAGGTACCCGACATTATGTTATTTCGGCGA (SEQ ID NO: 16) |
| PFC010W | ATACCGTCGACCAGTATATATAATCAAATTGAGCTTAAAAAG (SEQ ID NO: 17) | AATTAGGTACCAGTGTTTTAAGGCAATAATTATATTGTATT (SEQ ID NO: 18) |
| PFC0110W | TCGACCTCGAGCATAAAATTGTGTGTTTCATTAAAATCAT (SEQ ID NO: 19) | ACGTAGGGCCCATGTATAAATGAAAAATGAATGTGACTCTT (SEQ ID NO: 20) |
| PFC0115C | ATTCAGTCGACAAGAAAAAGGTAATATTTTAGTACACTCAA (SEQ ID NO: 21) | TATTCGGTACCTTTGTAATATACCTTTATGCGTTGACA (SEQ ID NO: 22) |
| PFC0120W | ATGCAGTCGACATGCACTCATTAATAATTTTAAACCGT (SEQ ID NO: 23) | TCGATGGGCCCCTTTTCAATTAATTTTATATTCTTTTGTTC (SEQ ID NO: 24) |
| PFC0125W | ATACCGTCGACCCTGACGATGAATTAATGATATCACG (SEQ ID NO: 25) | TATAAGGTACCCAGGTTAATATAGCCAAAATAAATTGAAA (SEQ ID NO: 26) |
| PFC0126C | ATAGAGTCGACGGATATTAGCTGATAAAGCAGCAGC (SEQ ID NO: 27) | GATTTGGTACCTTTGTTTTCATGTCCCATCATAATTC (SEQ ID NO: 28) |
| PFC0130C | ATACCGTCGACTATTCTACTTAAAGATGAATAGCACATATG (SEQ ID NO: 29) | ACATTGGGCCCTTCCCCTCACATATCAATCATAAAT (SEQ ID NO: 30) |
| ORF 147k | ATACAGTCGACGCATCCTATTCCCATCCTTTCCT (SEQ ID NO: 31) | ACTGAGGGCCCGACAAGAAGCATTACAGAGAGCAA (SEQ ID NO: 32) |
| PFC0135c | ATACCGTCGACATTTTGCCCAAGAATATAAAATAATAAGAT (SEQ ID NO: 33) | AATTAGGTACCCAGAGAAAGAAAAATGTCAATATAAATAAA (SEQ ID NO: 34) |

Allelic Exchange of Clag3

Allelic exchange was achieved by single-site homologous recombination of a Dd2 clag3.1 transgene into the HB3 genomic clag3.2. A DNA fragment containing the 3' portion (3219 bp) of clag3.1 and its 3' UTR (441 bp) was amplified from Dd2 with primers 5'-cataagcggccgcGCCATTCAGAC-CAAGCAAGG-3' (SEQ ID NO: 35) and 5'-ttaaactgcagC-TITCAATTAATTTTATATTCTTTTGTTC-3' (SEQ ID NO: 36). The amplicon was cloned into the pHD22Y plasmid (Fidock et al., PNAS, 94: 10931-36 (1997)) between NotI and PstI sites. The final transfection plasmid (pHD22Y-120w-flag-PG1) was constructed by addition of DNA sequence encoding tetra-cysteines and the FLAG epitope tag (FLNCCPCCMEPGSDYKDDDDK) (SEQ ID NO: 37) in frame before the gene's stop codon by standard site-directed mutagenesis. Homologous recombination into HB3 was detected by PCR five months after transfection. Recombinant parasites were enriched by sorbitol treatment with ISPA-28 and subjected to limiting dilution to yield the limiting dilution clone HB3$^{3rec}$.

Primers used for PCR verification of homologous recombination into the HB3 genome included those in Table 2:

TABLE 2

| primer | sequence |
|---|---|
| p1 | GTGGAATTGTGAGCGGATAACA (SEQ ID NO: 38) |
| p2 | TCATCGTCCTTATAGTCGGATCC (SEQ ID NO: 39) |
| p3 | ATGTTTTGTAATTTATGGGATAGCGA (SEQ ID NO: 40) |
| p4 | GTTGAGTACGCACTAATATGTCAATTTG (SEQ ID NO: 41) |
| p5 | AACCATAACATTATCATATATGTTAATTACAC (SEQ ID NO: 42) |

Southern Blot Hybridization

Genomic DNA was extracted using Wizard Genomic DNA extraction kit (Promega), digested with indicated restriction enzymes, resolved on a 0.7% agarose gel at 55 V for 18 hrs, and blotted onto positively charged Nylon membrane (Roche). A DNA probe complementary to hdhfr was prepared using primers (5'-ATTTCCAGAGAATGAC-CACAAC-3' (SEQ ID NO: 43) and 5'-TTAAGATGGC-CTGGGTGATTC-3') (SEQ ID NO: 44) and labeled with digoxigenin-dUTP. After prehybridization with DIG-Easy Hyb (Roche), the labeled probe was added and hybridized overnight at 39° C. The blot was washed with 0.1×SSC/ 0.5% SDS at 53° C., and blocked. Probe binding was then detected with anti-digoxigenin-AP Fab fragments at a dilution of 1:10,000 and CDP-Star substrate (Roche).

Quantification of Gene Expression by Real-Time PCR

Two-step real-time PCR was used to quantify expression of clag genes. Primers specific for each of the 5 clag genes were designed based on polymorphisms identified through DNA sequencing. Genomic DNA PCR using possible permutations of forward and reverse primers produced amplicons with only matched primer pairs, confirming specificity. Primers used included those in Table 3:

associated with the two clag3 genes yielded rapid selection, typically within 4-6 synchronizations. Additional synchronizations were required in reverse selections using ISPA-43, consistent with a relatively modest difference in affinity.

Polyclonal Antibody Production

DNA sequence encoding the C-terminal 141 amino acids of the Dd2 clag3.1 product was cloned into pET-15b vector (Novagen) for over-expression in *E. coli*. Standard site-directed mutagenesis was used to introduce a C-terminal FLAG epitope tag yielding the final plasmid (pet 15b-120w-4B) which encodes $NH_2$-MGSS<u>HHHHHH</u>SSGGTKKYGYLGEVIAARLSPKDKIMNYV HETNEDIMSNLRRYDMENAF KNKMSTYVDD-

TABLE 3

| gene (parasite line) | Forward primer sequence | Reverse primer sequence |
|---|---|---|
| clag2 (all) | CTCTTACTACTTATTATCTATCTCTCA (SEQ ID NO: 45) | CCAGGCGTAGGTCCTTTAC (SEQ ID NO: 46) |
| clag3.1 (Dd2, 7C12, 7C20, CH361) | ACCCATAACTACATATTTTCTAGTAATG (SEQ ID NO: 47) | GACAAGTTCCAGAAGCATCCT (SEQ ID NO: 48) |
| clag3.1 (HB3, HB3$^{3rec}$) | ACCCATAACTACATATTTTCTAGTAATG (SEQ ID NO: 49) | AGATTTAGTTACACTTGAAGAATTAGTATT (SEQ ID NO: 50) |
| clag3.2 (Dd2, 7C12, 7C20, CH361) | ACCCATAACTACATATTTTCTAGTAATG (SEQ ID NO: 51) | GATTTATAACTAGGAGCACTACATTTA (SEQ ID NO: 52) |
| clag3.2 (HB3) | ACCCATAACTACATATTTTCTAGTAATG (SEQ ID NO: 53) | TTATAACCATTAGGAGCACTACTTTC (SEQ ID NO: 54) |
| chimeric clag3reconi transgene (HBE$^{3rec}$) | ACCCATAACTACATATTTTCTAGTAATG (SEQ ID NO: 55) | GACAAGTTCCAGAAGCATCCT (SEQ ID NO: 56) |
| clag8 (all) | GTTACTACAACATTCCTGATTCAG (SEQ ID NO: 57) | AATGAAAATATAAAAATGCTGGGGAT (SEQ ID NO: 58) |
| clag9(Dd2, 7C12, 7C20, CH361) | TACCATTAGTGTTTTATACAGTTAAGG (SEQ ID NO: 59) | CCAAAATATGGCCAAGTACTTGC (SEQ ID NO: 60) |

Total RNA was harvested from synchronous schizont-stage cultures with Trizol reagent (Invitrogen) following the manufacturer's protocol. Residual genomic DNA contaminant was removed by TURBO-DNA-free kit (Ambion). Reverse transcription was performed using SuperScriptIII kit (Invitrogen) with oligo-dT as primer. Negative control reactions that omitted reverse transcriptase were used to exclude samples contaminated with genomic DNA. Real-time PCR was performed with QuantiTect SyBr Green PCR kit (Qiagen) and the above clag gene-specific primer pairs. Amplification kinetics were followed in the iCycler iQ multicolor real-time PCR system (Bio-Rad). Serial dilution of parasite genomic DNA was used to construct the standard curve for each primer pair. rhopH2, rhopH3, and PF7_0073 were used as loading controls. The presented data are normalized to the total clag3 transcript abundance.

In Vitro Selections of Parasites with Altered ISPA Efficacy

PSAC-mediated osmotic lysis of infected cells in unbuffered 280 mM sorbitol solution containing ISPA compounds was used to select for parasites with altered inhibitor efficacy. This strategy is based on rescue of parasites whose channels are blocked by addition of ISPA; it is analogous to the use of sorbitol in synchronization of parasite culture (Lambros et al., *J. Parasitol.*, 65:418-20 (1979)). Optimal selection conditions were determined from lysis kinetics and dose responses. Synchronizations were performed on consecutive days using 30 min incubations of cultures at room temperature with 5 μM ISPA-28 or 4 μM ISPA-43. The marked difference in ISPA-28 affinity between channels FAFFDDCGKNEQFLNERCDYCPVIEEVEETQLFTTT-GDKNTNKTTEIKKQ TSTYIDTEKMNEADSADSD-DEKDSDTPDDELMISRFH<u>DYKKDDDDK</u>-$CO_2H$ (SEQ ID NO: 61) (clag3.1 product italicized; hexa-histidine and FLAG tags underlined). Recombinant protein was produced in BL21 CodonPlus (DE3) REL cell line (Agilent Technologies) after transformation with pET-15b-120w-4B and induction with 0.5 mM IPTG for 3 hours. The recombinant protein was harvested by sonication in the presence of protease inhibitors, bound to Ni-NTA Superflow beads (Qiagen), eluted with imidazole under optimized conditions, and dialyzed. Purity and size were confirmed on coomassie-stained SDS-PAGE gels prior to submission for standard mouse immunizations by Precision Antibody (Columbia, Md.), an OLAW certified facility. Antibody titers were >1:100,000 by ELISA.

Protease Susceptibility Studies

Percoll-enriched synchronous trophozoite-infected cells were washed and treated with 1-2 mg/mL pronase E from *Streptomyces griseus* (Sigma Aldrich) at 5% hematocrit in PBS supplemented with 0.6 mM $CaCl_2$ and 1 mM $MgCl_2$ for 1 h at 37° C. Reactions were terminated by addition of 20 volumes of ice cold PBS with protease inhibitors (1 mM PMSF, 2 μg/mL pepstatin, and 2 μg/mL leupeptin) and exhaustive washing. Effectiveness of the protease treatment and the block by protease inhibitors was evaluated by examining PSAC activity with sorbitol uptake measurements. Protease accessibility to erythrocyte cytosol was examined by measuring hemoglobin band intensity in coomassie-stained SDS-PAGE gels of total cell lysate. Band intensity was quantified with ImagaJ software (http://rsbweb.nih.gov/) and revealed no detectable hemoglobin degradation (mean of 997±2% relative to untreated controls, n=7 separate trials).

Membrane Fractionation

Infected cells, with or without prior protease treatment, were hemolysed in 40 volumes of lysis buffer (7.5 mM $Na_2HPO_4$, 1 mM EDTA, 7.51 with protease inhibitors and ultracentrifuged (70,000×g, 4° C., 1 h). The supernatant was collected as the 'soluble' fraction before resuspending the pellet in 100 mM $Na_2CO_3$, pH 11 at 4° C. for 30 min before centrifugation (70,000×g). The "carbonate extract" supernatant was neutralized with 1/10 volume 1 M HCl. The final pellet was washed with lysis buffer before solubilization as the "membrane" fraction in 2% SDS.

Immunofluorescence Confocal Microscopy

Synchronous parasite cultures were washed and used to make thin smears on glass slides. The cells were air dried prior to fixation in 100% methanol (ice-cold for merozoites and RT for trophozoites) for 5 min. After incubation in 10% Goat Serum Blocking Solution (Invitrogen) with 0.1% Triton X-100, primary antibody against the clag3 recombinant protein and secondary antibody (Alexa Fluor 488 goat anti-mouse IgG, invitrogen) were applied in the same buffer at 1:50 and 1:500 dilution, respectively with thorough washing between antibodies. Nuclei were stained with Hoechst 33342 before mounting in Fluoromount-G (SouthernBiotech). Dual color fluorescence images were taken on a Leica SP2 confocal microscope under a 100× oil immersion objective with serial 405 nm and 488 nm excitations. Images were processed in linaris 6.0 (Bitplane AG) and uniformly de convolved using Huygens Essential 3.1 (Scientific Volume Imaging BV).

Immunoblots

Protein samples were denatured and reduced in NuPAGE® LDS Sample Buffer (invitrogen) with 100 mM DTT and run on NuPAGE® Novex 4-12% Bis-Tris gels in MES Buffer (Invitrogen), and transferred to nitrocellulose membrane. After blocking (3% fat-free milk in 150 mM NaCl, 20 mM TrisHCl, pH 7.4 with 0.1% Tween20), anti-recombinant clag3 product or anti-FLAG (Cell Signalling Technology), was applied at 1:3000 dilution in blocking buffer. After washing, binding was detected with HRP-conjugated secondary antibodies (Pierce) at 1:3000 dilution and chemiluminescent substrate (Immobilon, Millipore or SuperSignal West Pico, Pierce).

Computational Analyses

Phylogenetic analysis of clag products and the more distantly related RONs was conducted using an approximately-maximum-likelihood method implemented in the FastTree 2.1 program under default parameters (Price et al. *Mol. Biol. Evol.*, 26: 1641-50 (2009)). Transmembrane domains were predicted using the TMHMM and Phobias programs (Krogh et al., *J. Mol. Biol.*, 305: 657-80 (2001); Kall et al., *Bioinformatics*, 21 Suppl. 1: i251-57 (2005)). Improved confidence in transmembrane domain prediction was achieved by inputting multiple alignments of group 2 clag products from several plasmodial species in the Poly-Phobius mode.

Example 1

This example demonstrates the activity of compounds according to formulas (1a) and (2a) below against PSAC. This example also demonstrates the in vitro growth inhibitory activity of compounds (1a) and (2a) in nutrient-rich RPMI and PSAC-limiting medium (PLM). The compounds of formulas (1a) and (2a) are in accordance with an embodiment of the invention.

The concentration of a chemical inhibitor required to produce 50% block of PSAC-mediated solute uptake, $K_{0.5}$ for PSAC block (Table 4), was measured as described previously (*Biophysical J.* 84:116-23, 2003). The chemical inhibitors included:

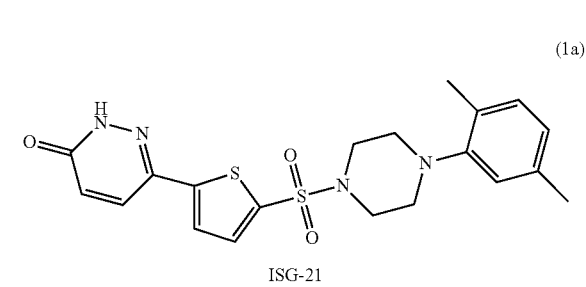

ISG-21

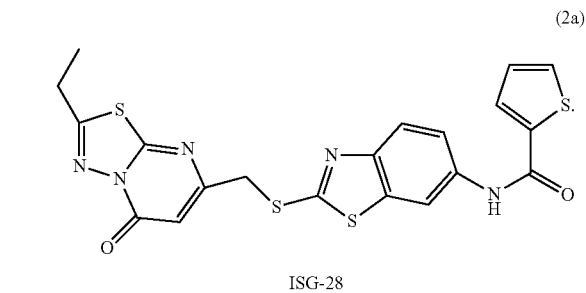

ISG-28

Briefly, *P. falciparum* trophozoites were obtained by in vitro culture in human erythrocytes, enriched by density gradient centrifugation, and used in a continuous light-scattering osmotic lysis assay in sorbitol lysis solution (in mM: 280 sorbitol, 20 Na-HEPES, 0.1 mg/ml BSA, pH 7.4). In this assay, increases in transmittance (% T, measured at 700 nm) correlated directly to lysis of infected RBCs and were plotted in arbitrary units. Uninfected RBCs lacked PSAC activity and had undetectably low sorbitol permeability. Uptake of other nutrient solutes and patch-clamp methods confirmed that this transmittance assay provides a quantitative measure of PSAC inhibition by compounds (1a) and (2a). The PSAC inhibitors of compounds (1a) and (2a) represent a novel strategy for intervention against malaria parasites because currently approved antimalarial drugs (artemisinin, mefloquine, and chloroquine) did not inhibit PSAC activity (Table 4).

In vitro parasite killing by PSAC inhibitors was quantified using a SYBR Green I-based fluorescence assay for parasite nucleic acid in 96-well format. Parasite cultures were synchronized by incubation in 5% D-sorbitol before seeding at 1% parasitemia and 2% hematocrit in standard media for parasite cultivation (RPMI 1640 supplemented with 25 mM HEPES, 50 mg/L hypoxarithine, and 10% regular serum) or in PSAC-limiting medium (PLM, a novel medium based on the RPMI 1640 formulation but with reduced concentrations of isoleucine, glutamine, and hypoxanthine, three nutrients whose uptake by infected cells is primarily via PSAC). While RPMI 1640 contained supraphysiological concentrations of these nutrients, the values in PLM were closer to those measured in plasma from healthy human donors.

Cultures were maintained for 3 days at 37° C. in 5% $O_2$, 5% $CO_2$ without media change. After this incubation, Sybr Green I was added in 20 mM Tris, 10 mM EDTA, 0.016% saponin, 1.6% triton X100. Subsequent fluorescence measurements (excitation/emission at 485/528 nm) permitted quantification of parasite growth because the fluorescence of Sybr Green 1 was a measure of parasite nucleic acid content. Table 4 shows the concentration of each PSAC inhibitor (compounds of formulas (1a) or (2a)) or control antimalarial drug (artemisinin, mefloquine, or chloroquine) required to produce a 50% reduction in parasite survival in RPMI 1640 (RPMI $IC_{50}$) or PLM (PLM $IC_{50}$). Improved killing by PSAC inhibitors (compounds of formulas (1a) and (2a)) upon testing in PLM indicated that the PSAC inhibitors may have a novel mechanism of parasite killing. These data supported a role of PSAC in parasite nutrient acquisition because nutrient limitation improved PSAC inhibitor efficacy, but did not significantly alter killing by artemisinin, mefloquine, or chloroquine (see Ratio of $IC_{50}$ (RPMI/PLM)).

TABLE 4

| Structure | MW | clogP | $K_{0.5}$ for PSAC block, nM | RPMI $IC_{50}$, µM | PLM $IC_{50}$, µM | Ratio (RPMI/PLM) |
|---|---|---|---|---|---|---|
| Compound of formula (1a) | 431 | 3.5 | 3 | 1.5 | 0.0023 | 800 |
| Compound of formula (2a) | 486 | 5.3 | 10 | >30 | 0.3 | >100 |
| Artemisinin | 282 | 2.7 | inactive | 0.018 | 0.026 | 0.66 |
| Mefloquine | 378 | 3.7 | inactive | 0.022 | 0.033 | 0.66 |
| Chloroquine | 319 | 5.1 | inactive | 0.22 | 0.34 | 0.67 |

Example 2

This example demonstrates the identification of isolate-specific inhibitors, which effectively inhibit PSAC activity associated with a specific parasite line. This example also demonstrates that an inhibitor in accordance with the invention interacts directly with PSAC.

A search for small molecule inhibitors with differing efficacies against channels induced by divergent parasite lines was performed. Such inhibitors presumably bind to one or more variable sites on the channel, which may result either from polymorphisms in a parasite channel gene or from differing activation of human channels. To find these inhibitors, a transmittance-based assay that tracks osmotic lysis of infected cells in sorbitol, a sugar alcohol with increased permeability after infection was used (Wagner et al., Biophys. J., 84: 116-23 (2003)). This assay had been adapted to 384-well format and used to find high affinity PSAC inhibitors (Pillai et al., Mol. Pharmacol., 77: 724-33 (2010)). Here, this format was used to screen a library of compounds against erythrocytes infected with the HB3 and Dd2 P. falciparum lines. To maximize detection of hits, a low stringency was chosen in the screens by using library compounds at a high concentration (10 µM) and by reading each microplate at multiple timepoints (Pillai et al., Mol. Pharmacol., 77: 724-33 (2010)). 8% of compounds met or exceeded the threshold of 50% normalized block at 2 h [% B=100*$(A_{cpd}-Ã_{neg})/(Ã_{pos}-Ã_{neg})$], consistent with a low screening stringency. A weighted difference statistic (WDS) was defined that normalized measured differences in efficacy against HB3 and Dd2 channels to the standard deviation of positive control wells in each microplate [WDS=|% $B_{HB3}$-% $B_{Dd2}$|/(3*$σ_{pos}$)]. 86% of all compounds produced indistinguishable effects on the two parasite lines (WDS≤1.0). Thus, most inhibitor binding sites were conserved.

Nevertheless, a small number of compounds produced significantly differing activities in the two screens. One such inhibitor, named ISPA-28 (for isolate-specific PSAC antagonist based on studies described below, Formula A below), was reproducibly more effective at inhibiting sorbitol uptake by Dd2- than HB3-infected cells. Secondary studies with ISPA-28 revealed an ~800-fold difference in half-maximal affinities ($K_{0.5}$ values of 56±5 nM vs. 43±2 µM for Dd2 and HB3, respectively; $P<10^{-10}$).

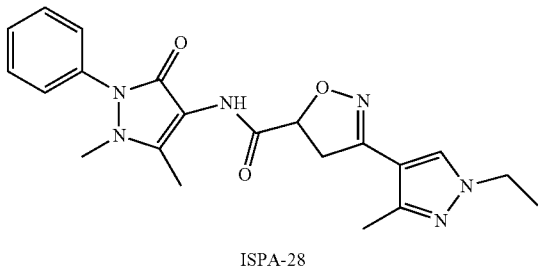

(Formula A)

ISPA-28

ISPA-28 effects on uptake of the amino acids alanine and proline as well as the organic cation phenyl-trimethylammonium (PhTMA), solutes with known increases in permeability after infection (Ginsburg et al., Mol. Biochem. Parasitol. 14: 313-22 (1985); Bokhari et al., J. Membr. Biol. 226: 27-34 (2008)), were also examined. Each solute's permeability was inhibited with dose responses matching those for sorbitol. Without being bound by a particular theory or mechanism, it is believed that these data provide evidence for a single shared transport mechanism used by these diverse solutes.

22 different laboratory parasite lines were next tested and significant transport inhibition was found with only Dd2 and W2. Because Dd2 was generated by prolonged drug selections starting with W2 (Wellems et al., Nature, 345: 253-55 (1990)), their channels' distinctive ISPA-28 affinities suggested a stable heritable element in the parasite genome.

To explore the mechanism of ISPA-28 block, patch-clamp of infected erythrocytes was performed. Using the whole-cell configuration, similar currents on HB3- and Dd2-infected cells in experiments without known inhibitors were observed. These currents exhibited inward rectification. Previous studies determined that they were carried primarily by anions with a permeability rank order of $SCN^->I^->Br^->Cl^-$ (Desai et al., Nature, 406: 1001-05 (2000)). 10 µM ISPA-28 reduced these currents, but had a significantly greater effect on Dd2-infected cells. In the cell-attached configuration with 1.1 M $Cl^-$ as the charge carrier, ion channel activity characteristic of PSAC was detected on both lines (~20 pS slope conductance with fast flickering gating, (Alkhalil. et al., Blood, 104: 4279-86 (2004)); without inhibitor, channels from the two lines were indistinguishable. However, recordings with 10 µM ISPA-28 revealed a marked difference as Dd2 channels were near-fully inhibited whereas HB3 channels were largely unaffected. Thus, this compound's effects on single PSAC recordings parallel those on uptake of sorbitol and other organic solutes.

Closed durations from extended recordings were analyzed and it was determined that ISPA-28 imposed a distinct population of long block events, but only in recordings on Dd2-infected cells. At the same time, intrinsic channel closings, which occur in the absence of inhibitor, were conserved on both parasites and were not affected by ISPA-28.

Example 3

This example demonstrates the inheritance of ISPA-28 efficacy in a Dd2×HB3 genetic cross and that piggyback-mediated complementations implicate clag 3.1 and clag 3.2 in PSAC activity.

ISPA-28 efficacy against PSAC activity on red blood cells infected with recombinant progeny clones from the Dd2× HB3 genetic cross (Wellems et al., Nature, 345: 253-255 (1990)) was next examined. For each clone, sorbitol uptake was examined in the absence and presence of 7 µM ISPA-28, a concentration that optimally distinguishes the parental channel phenotypes, and quantified inhibition [% B=100* $(A_{cpd}-\tilde{A}_{neg})/(\tilde{A}_{pos}-\tilde{A}_{neg})$]. Although a few of the 34 independent progeny clones exhibited intermediate channel inhibition, most resembled one or the other parent. Quantitative trait locus (QTL) analysis was used to search for associations between ISPA-28 efficacy and inheritance of available microsatellite markers. A primary scan identified a single significant peak having a logarithm of odds (LOD) score of 12.6 at the proximal end of chromosome 3. A secondary scan for residual effects did not find additional peaks reaching statistical significance.

The mapped locus contained 42 predicted genes. Although none had homology to classical ion channels from other organisms, many were conserved in other plasmodia, as expected for the responsible gene(s) from conservation of PSAC activity in malaria parasites ((Lick et al., Eukaryot. Cell, 4: 2153-59 (2005)). The mapped region was enriched in genes encoding proteins destined for export to host cytosol ($P<10^{-4}$ by simulation), as typical of apicomplexan subtelomeric regions. Some of the encoded proteins had one or more predicted transmembrane domains as usually involved in channel pore formation, but this criterion may miss some transport proteins. The PEXEL motif, which directs parasite proteins to the host cell (Marti et al., Science, 306: 1930-33 (2004)), was present in some genes, but this module is not universally required for export (Spielman et al., Trends Parasitol. 26: 6-10 (2010)). Thus, computational analyses suggested several candidates, but could not specifically implicate any as ion channel components.

A DNA transfection approach was chosen and piggyBac transposase was chosen to complement Dd2 parasites with the HB3 allele of individual candidate genes (Balu et al., PNAS, 102: 16391-96 (2005)). With this method, successfully transfected parasites will carry both parental alleles and therefore be merodiploid for candidate genes. Nevertheless, the marked difference in ISPA-28 efficacy between the parental lines would be expected to produce a detectable change in transport phenotype upon complementation with the responsible gene. The high efficiency of random integration conferred by piggyBac permits rapid examination of many genes (Batu et al., BMC Microbiol., 9: 83 (2009)).

Fourteen genes were cloned with their endogenous 5' and 3' UTR regions from the HB3 parent into the pXL-BacII-DHFR plasmid; a 15$^{th}$ construct containing a conserved but not annotated open reading frame (ORF 147 kb) was also prepared. Each was transfected individually along with a helper plasmid encoding the transposase into Dd2 parasites. Selection for hDHFR expression yielded parasites that stably carried both Dd2 and HB3 alleles for each candidate. Because an altered channel phenotype presumably requires expression of the HB3 allele, reverse transcriptase PCR was used to amplify polymorphic regions of each gene and the amplicons were sequenced to determine if both parental alleles were transcribed; this approach continued expression of 12 candidates. ISPA-28 dose responses for inhibition of sorbitol uptake by erythrocytes infected with each transfectant were performed. Two transfectants, expressing HB3 alleles for PFC0110w (clag 3.2) and PFC0120w (clag 3.1), produced significant changes in ISPA-28 efficacy with $K_{0.5}$ values between those of Dd2 and HB3, as expected for cells carrying channels from both parental lines (P=0.01 and $P<10^{-7}$ in comparison to Dd2, respectively). Limiting dilution cloning of the PFC0120w transfectant yielded a clone, Dd2-pB120w, which had undergone at least one integration event; its ISPA-28 $K_{0.5}$ was indistinguishable from the transfection pool. For both genes, quantitative analyses suggested relatively low level expression of the HB3 allele because the transfectant $K_{0.5}$ values (95±8 and 140±12 nM) were closer to those of Dd2 than of HB3. Without being bound by a particular theory or mechanism, it is believed that expression levels of the two parental alleles may be influenced by the genomic environment of the integration site, relative promoter efficiencies, and a gene silencing mechanism examined below.

Example 4

This example confirms a role for clag 3.1. and clag 3.2 in PSAC activity. This example also demonstrates that clag3 gene silencing and switched expression determine inhibitor affinity.

To examine the unexpected possibility that clag3 products contribute to PSAC activity, an allelic exchange strategy was used to transfer potent ISPA-28 block from the Dd2 line to HB3 parasites. Because Dd2 parasites express clag3.1 but not clag3.2 (Kaneko et al., Mol. Biochem. Parasitol., 143: 20-28 (2005)), their clag3.1 gene presumably encodes high ISPA-28 affinity. Therefore, a transfection plasmid was constructed carrying a 3.2 kb fragment from the 3' end of the Dd2 clag3.1 allele, an in-frame C-terminal FLAG tag followed by a stop codon, and the fragment gene's 3' untranslated region (pHD22Y-120w-flag-PG1). Because this plasmid carries only a gene fragment and lacks a leader sequence to drive expression, an altered transport phenotype requires recombination into the parasite genome. HB3 was transfected with this plasmid and PCR was used to screen for integration into each of the five endogenous clag genes. This approach detected recombination into the HB3 clag3.2 gene; limiting dilution cloning yielded HB3$^{3rec}$, a clone carrying a single site integration event without residual episomal plasmid. DNA sequencing indicated recombination between single nucleotide polymorphisms at 3718 and 4011 bp from the HB3 clag3.2 start codon. This recombination site corresponded to successful transfer of downstream polymorphisms including a recognized hypervariable region at 4266-4415 bp; contamination with other laboratory parasite lines was excluded by fingerprinting.

Figure 2:
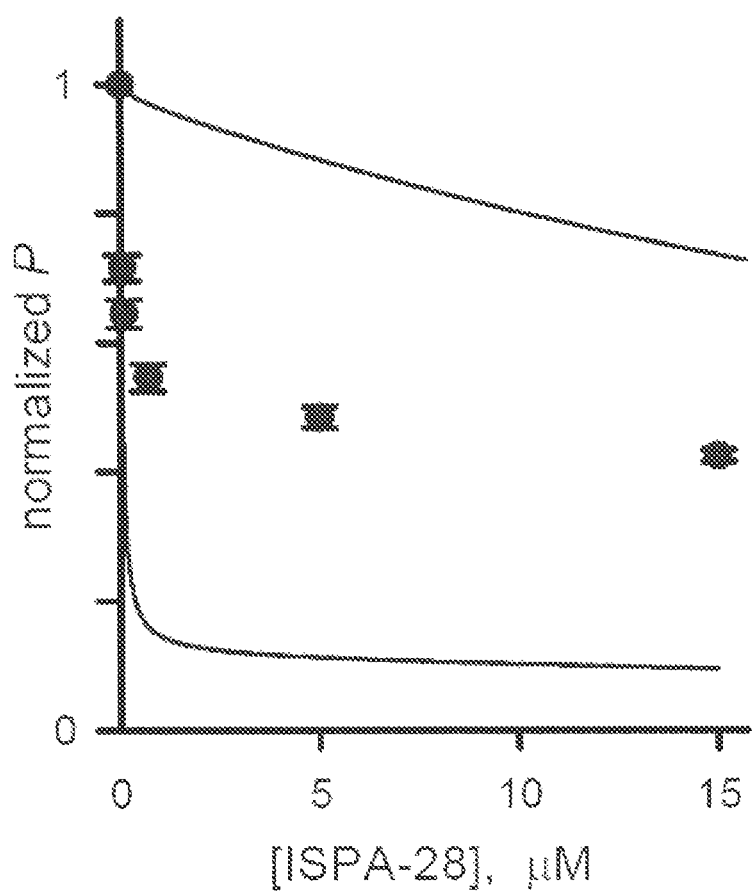

PSAC activity on HB3$^{3rec}$ exhibited a marked increase in ISPA-28 efficacy (FIG. 1), further supporting a role for clag3 genes in sorbitol and nutrient uptake. Although this allelic exchange strategy yielded a gene replacement in contrast to the complementations achieved with piggyBac, the channel's ISPA-28 affinity was again intermediate between those of HB3 and Dd2 (FIG. 2). Without being bound by a particular theory or mechanism, it is believed that several mechanisms may contribute to the quantitatively incomplete transfer of inhibitor affinity. First, two or more polymorphic sites on the protein might contribute to ISPA-28 binding. If some of these sites are upstream from the recombination event, the resulting chimeric protein may have functional properties distinct from those of either parental line. Second, the channel may contain additional unidentified subunits; here, transfection to replace each contributing HB3 gene with Dd2 alleles might be required to match the ISPA-28 affinity of Dd2. Finally, in addition to the chimeric clag3.2$_{HB3}$-3.1$_{Dd2}$ gene produced by transfection, HB3$^{3rec}$ also carries the clag3.1 gene endogenous to HB3 parasites. Expression of both paralogs could also produce an intermediate ISPA-28 affinity.

To explore these possibilities, a cell-attached patch-clamp was performed on HB3$^{3rec}$-infected cells. Individual channel molecules exhibiting ISPA-28 potencies matching those of each parental line were identified. These recordings excluded scenarios that require a homogenous population of channels.

In addition to the complex behavior of HB3$^{3rec}$, it was noticed that certain progeny from the genetic cross had lower ISPA-28 affinity than Dd2 despite inheriting the mapped chromosome 3 locus fully from the Dd2 parent. Because subtelomeric multigene families in *P. falciparum* are susceptible to recombination and frequent gene conversion events (Freitas-Junior et al., *Nature*, 407: 1018-22 (2000)), both clag3 paralogs and neighboring genomic DNA from 7C20 and Dd2 were sequenced but no DNA-level differences were found. Epigenetic mechanisms that may influence ISPA-28 affinity were therefore considered. clag3.1 and clag3.2 have been reported to undergo mutually exclusive expression (Cortes et al., *PLoS Pathog.*, 3: e107 (2007)). Monoallelic expression and switching, also documented for other gene families in *P. falciparum* (Chen et al. Nature, 394: 392-95 (1998); Lavarec et al., *Mol. Microbial.*, 64: 1621-34 (2007)), allow individual parasites to express a single member of a multigene family. Daughter parasites resulting from asexual reproduction continue exclusive expression of the same gene through incompletely understood epigenetic mechanisms (Howitt et al., *Mol. Microbial.*, 73: 1171-85 (2009)). After a few generations, some daughters may switch to expression of another member of the gene family, affording diversity that contributes to immune evasion (Sherf et al., *Annu. Rev. Microbial.*, 62: 445-70 (2008)).

Reverse transcriptase PCR was performed and it was found that Dd2 expresses clag3.1 almost exclusively while the three discordant progeny express clag3.2 at measurable levels, suggesting epigenetic regulation. Selective pressure was therefore applied to progeny cultures with osmotic lysis in sorbitol solutions containing ISPA-28. Inclusion of ISPA-28 preferentially spares infected cells whose channels have high inhibitor affinity: these cells incur less sorbitol uptake and do not lyse. These selections, applied on multiple consecutive days, yielded marked reductions in parasitemia. Surviving parasites exhibited improved ISPA-28 affinity quantitatively matching that of the Dd2 parent. Identical selections applied HB3 and three progeny inheriting its chromosome 3 locus did not change ISPA-28 affinity, excluding effects of the selections on unrelated genomic sites.

Real time OCR using primers specific for each of the 5 clag genes revealed that selection with sorbitol and ISPA-28 reproducibly increased clag3.1 expression while decreasing that of clag3.2 in progeny inheriting the Dd2 locus. Selections applied to the parental HB3 line were without effect, consistent with its unchanged inhibitor affinity. These selections did not alter relative expression of other paralogs (clag2, clag8, and clag9).

Selections were also applied to HB3$^{3rec}$, which carries a chimeric clag3.2$_{HB3}$-3.1$_{Dd2}$ transgene and the clag3.1 gene native to HB3. In contrast to the lack of effect on the isogenic HB3 line, these synchronizations increased the transfectant's ISPA-28 affinity to a K$_{0.5}$ of 51±9 nM, matching that of Dd2 channels. This change in channel phenotype correlated with a near exclusive expression of the transgene, confirming that expression of HB3 clag3.1 by a subset of cells accounts for the intermediate ISPA-28 affinity. These findings also delimit the determinants of ISPA-28 binding to polymorphic sites within the Dd2 clag3.1 gene fragment transferred to HB2$^{3rec}$.

Without being bound to a particular theory or mechanism, it is believed that expression switching in *P. falciparum* multigene families occurs over several generations and should lead to a drift in population phenotype. After selection of the chimeric gene in HB3$^{3rec}$, continued in vitro propagation yielded a gradual decay in ISPA-28 affinity that correlated with decreasing transgene expression. As with other multigene families (Lavazec et al., *Mol. Microbiol.*, 64: 1621-34 (2007)), several factors may affect the steady-state ISPA-28 affinity and relative expression levels for the two clag3 genes upon continued culture without selective pressure.

Example 5

This example demonstrates reverse selection with ISPA-43 and a clag3 mutation in a leupeptin-resistant PSAC mutant.

A PSAC inhibitor with reversed specificity for the two Dd2 clag3 products was next sought. To this end, hits from the high-throughput screen of Example 2 were surveyed using the progeny clone 7C20 before and after selection for clag3.1 expression. This secondary screen identified ISPA-43 as a PSAC inhibitor with an allele specificity opposite that of ISPA-28 (Formula B below (K$_{0.5}$ of 32 and 3.9 μM for channels associated with clag3.1 and clag3.2 genes from Dd2, respectively).

A stable parasite mutant with altered PSAC selectivity, gating, and pharmacology was recently generated by in vitro selection of HB3 with leupeptin (Lisle et al., *Antimicrob. Agents Chemother*, 52: 2346-54 (2008)). Clag3 genes were sequenced from this mutant, HB3-leuR1, and identified a point mutation within its clag3.2 gene that changes the conserved A1210 to a threonine, consistent with a central role of clag3 genes in solute uptake. HB3-leuR1 silences its unmodified clag3.1 and preferentially expresses the mutated clag3.2 (expression ratio of 19.2±1.5), as required for a direct effect on PSAC behavior. Because this mutation is within a predicted transmembrane domain, it may directly account for the observed changes in channel gating and selectivity.

Formula B

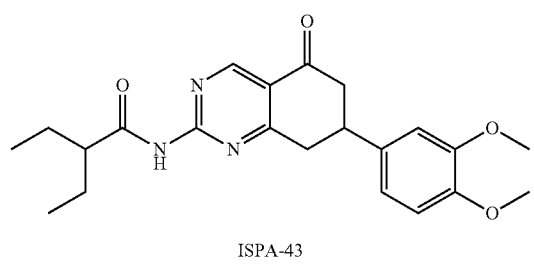

ISPA-43

Sorbitol synchronizations with 4 μM ISPA-43 were then applied to the clag3.1-expressing 7C20 culture and achieved robust reverse selection: the surviving parasites exhibited both low ISPA-28 affinity and a reversed clag3 expression profile. Thus, inhibitors can be used in purifying selections of either clag3 gene. Because ISPA-28 affinity can be reduced either through drift without selective pressure or by selection for the alternate paralog with an inhibitor having reversed specificity, these studies alleviate concerns about indirect effects of exposure to sorbitol or individual inhibitors.

A stable parasite mutant with altered PSAC selectivity, gating, and pharmacology was recently generated by in vitro selection of HB3 with leupeptin (Lisk et al., $Antimicrob.$ $Agents$ $Chemother$, 52: 2346-54 (2008)). Clag3 genes from this mutant, HB3-leuR1, were sequenced and a point mutation was identified within its clag3.2 gene that changed the conserved A1210 to a threonine, consistent with a central role of clag3 genes in solute uptake. HB3-leuR1 silenced its unmodified clag3.1 and preferentially expressed the mutated clag3.2 (expression ratio of 19.2±1.5), as required for a direct effect on PSAC behavior. Without being bound by a particular theory or mechanism, it is believed that because this mutation is within a predicted transmembrane domain, it may directly account for the observed changes in channel gating and selectivity.

Example 6

This example demonstrates that clag3 products are exposed at the host erythrocyte surface.

To directly contribute to PSAC activity, it is believed that at least some of the clag3 product would associate with the host membrane, presumably as an integral membrane protein. Polyclonal antibodies were therefore raised to a carboxy-terminal recombinant fragment conserved between the two clag3 products. Confocal microscopy with this antibody confirmed reports localizing these proteins to the host cytosol and possibly the erythrocyte membrane as well as within rhoptries of invasive merozoites (Vincensini et al., $Mol.$ $Biochem.$ $Parasitol.$, 160: 81-89 (2008)). To obtain more conclusive evidence, immunoblotting was used to examine susceptibility of these proteins to extracellular protease. Without protease treatment, a single ~160 kDa band was detected in whole-cell lysates, consistent with the expected size of clag3 products. Treatment with pronase E under conditions designed to prevent digestion of intracellular proteins reduced the amount of the full-length protein and revealed a 35 kDa hydrolysis fragment. In contrast, a monoclonal antibody against KAHRP, a parasite protein that interacts with the host membrane cytoskeleton but is not exposed (Kilejian et al., $Mol.$ $Biochem.$ $Parasitol.$, 44, 175-81 (1991)), confirmed that intracellular proteins are resistant to hydrolysis under these conditions. As reported for another protease (Baumeister et al., $Mol.$ $Microbiol.$, 60: 493-04 (2006)), pronase E treatment significantly reduced PSAC-mediated sorbitol uptake; this effect was sensitive to protease inhibitors, suggesting that proteolysis at one or more exposed sites interferes with transport.

Ultracentrifugation of infected cell lysates revealed that the clag3 product is fully membrane-associated; a fraction could however be liberated by treatment with $Na_2CO_3$, which strips membranes of peripheral proteins (Fujiki et al., $J.$ $Cell$ $Biol.$, 93: 97-102 (1982)). Because this fraction was protease insensitive, it reflects an intracellular pool of clag3 product loosely associated with membranes. The C-terminal hydrolysis fragment was present only in the carbonate-resistant insoluble fraction, indicating an integral membrane protein.

Because the polyclonal antibodies might cross-react with clag products from other chromosomes, protease sensitivity was next examined in $HB3^{3rec}$, whose chimeric clag3 transgene encodes a C-terminal FLAG tag. Anti-FLAG antibody recognized a single integral membrane protein in $HB3^{3rec}$ and no proteins from the parental HB3 line, indicating specificity for the recombinant gene product. Treatment with pronase E prior to cell lysis and fractionation revealed a hydrolysis fragment indistinguishable from that seen with the antibody raised against the native protein's C-terminus.

The following procedures were followed for the experiments described in Examples 7-10:

Parasite Cultivation, Design of PLM, and Growth Inhibition Studies

Asexual stage $P.$ $falciparum$ laboratory lines were propagated by standard methods in RPMI 1640 supplemented with 25 mM HEPES, 31 mM $NHCO_3$, 0.37 mM hypoxanthine, 10 μg/mL gentamicin, and 10% pooled human serum. PLM is based on this standard medium and was designed after surveying parasite growth in media lacking individual constituents with known PSAC permeability: hypoxanthine, calcium panthothenate, and the amino acids Cys, Glu, Gln, Ile, Met, Pro, and Tyr (Saliba et al., $J.$ $Biol.$ $Chem.$, 273: 10190-10195 (1998)). PLM contained reduced concentrations of isoleucine (11.4 μM), glutamine (102 μM), and hypoxanthine (3.01 μM); human serum was exhaustively dialyzed against distilled $H_2O$ prior to supplementation in this medium.

Growth inhibition experiments were quantified using a SYBR Green I-based fluorescence assay for parasite nucleic acid in 96-well format, as described previously (Pillai et al., $Mol.$ $Pharmocol.$, 77: 724-733 (2010)). Ring-stage synchronized cultures were seeded at 1% parasitemia and 2% hematocrit in standard medium or PLM and maintained for 72 h at 37° C. in 5% $O_2$, 5% $CO_2$ without media change. Cultures were then lysed in 20 mM Tris, 10 mM EDTA, 0.016% saponin, and 1.6% triton X100, pH 7.5 with SYBR Green I at twice the manufacture's recommended concentration (Invitrogen, Carlsbad, Calif.). After a 45 min incubation, parasite DNA content was quantified by measuring fluorescence (excitation/emission wavelengths, 485/528 nm). For each inhibitor concentration, the mean of triplicate measurements was calculated after subtraction of background fluorescence from matched cultures killed by 20 μM chloroquine. Growth inhibition studies with the $HB3^{3rec}$ parasite were performed after transport-based selection with ISPA-28 to achieve expression of the chimeric clag3 gene generated by allelic, exchange transfection.

Transport Inhibition Assays

Inhibitor affinity for PSAC block was determined using a quantitative transmittance assay based on osmotic lysis of infected cells in sorbitol (Wagner et al., $Biophys.$ $J.$, 84: 116-123 (2003)). Parasite cultures were enriched at the trophozoite stage using the Percoll-sorbitol method, washed, and resuspended at 37° C. and 0.15% hematocrit in 280 mM sorbitol, 20 mM Na-HEPES, 0.1 mg/ml BSA, pH 7.4 with indicated concentrations of inhibitors. PSAC-mediated sorbitol uptake produces osmotic lysis, which was continuously tracked by measuring transmittance of 700 nm light through the cell suspension (DU640 spectrophotometer with Peltier temperature control, Beckman Coulter). Inhibitor dose responses were calculated from the time required to reach fractional lysis thresholds. ISPA-28 dose responses were fitted to the sum of two Langmuir isotherms (Eq/S1). Other inhibitors had dose responses that are adequately fitted by a single Langmuir isotherm.

To examine possible inhibitor metabolism in parasite culture, Dd2 parasites were cultivated in standard media with 40 µM ISPA-28 at 37° C. for 72 h. After centrifugation, the culture supernatant was used as a source of ISPA-28 for comparison to freshly-prepared compound in transport inhibition studies.

QTL Analysis

We sought genetic loci associated with ISPA-28 growth inhibitory efficacy in the Dd2×HB3 genetic cross (Wellems et al., *Nature*, 345: 253-255 (1990)) using 448 previously selected polymorphic markers that distinguish the Dd2 and HB3 parental lines (Nguitragool et al., *Cell*, 145: 665-677 (2011)), QTL analysis was performed using R/qtl software (freely available at http://www.rqtl.org/) as described (Broman et al., *Bioinformatics*, 19: 889-890 (2003)) and conditions suitable for the haploid asexual parasite. A P=0.5 significance threshold was estimated with permutation analysis. Growth inhibition data at 0.3 and 10 µM ISPA-28 identified the same locus reported with 3 µM ISPA-28. Additional QTL were sought with secondary scans by controlling for the clag3 locus.

Quantitative RT-PCR

Two-step real-time PCR was used to quantify clag gene expression using allele-specific primers developed previously (Nguitragool et al., *Cell*, 145: 665-677 (2011)). RNA was harvested from schizont-stage cultures with TRIzol reagent (Invitrogen), treated with DNase to remove residual genomic DNA contaminant, and used for reverse transcription (SuperScriptIII and oligo-dT priming, Invitrogen). Negative control reactions without reverse transcriptase confirmed there was no genomic DNA contamination. Real-time PCR was performed with QuantiTect SyBr Green PCR kit (Qiagen), the iCycler iQ multicolor real-time PCR system (Bio-Rad), and dug gene-specific primers. Serial dilution of parasite genomic DNA was used to construct the standard curve for each primer pair, PF7_0073 was used as a loading control as it is constitutively expressed. Transcript abundance for each clag gene was then determined from amplification kinetics.

PCR Studies for Clag3 Recombination

The clag3 locus of Dd2-PLM28 was characterized with genomic DNA and allele-specific primers: 3.1f (5'-GTG-CAATATATCAAAGTGTACATGCA-3') (SEQ ID NO: 68), 3.1r (5'-AAGAAAATAAATGCAAAACAAGTTAGA-3') (SEQ ID NO: 69), 3.2r (5'-GTTGAGTACGCACTAATAT-GTCAATTTG-3') (SEQ ID NO: 41), and 3.2r (5'-AAC-CATAACATTATCATATAIGTTAATTACAC-3') (SEQ ID NO: 42). cDNA prepared from schizontstage cultures was also used with these primers to examine expression of both native and chimeric clag3 genes.

Southern Blot

A clag3-specific probe was prepared by PCR amplification from Dd2 genomic DNA using 5'-ATTIA-CAAACAAAGAAGCTCAAGAGGA-3' (SEQ ID NO: 70) and 5'-TTTTCTATATCTTCATTTTCTTTAATTGTTC-3' (SEQ ID NO: 71) in the presence of Digoxygenin (DIG)-dUTP (Roche). Probe specificity was confirmed by blotting against full-length PCR amplicons of the five clag genes generated from Dd2 genomic DNA with primers.

Genomic DNA was digested with indicated restriction enzymes (New England BioLabs), subjected to electrophoresis in 0.7% agarose, acid depurinated, transferred and crosslinked to Nylon membranes. The blot was then hybridized overnight at 39° C. with the above DIG-labeled probe in DIG Easy Hyb (Roche), and washed with low and high stringency buffers (2×SSC, 0.1% SDS, 23° C. followed by 1×SSC, 0.5% SDS, 50° C.) prior to DIG immunodetection according to the manufacturer's instructions.

Mammalian Cytotoxicity

Cytotoxicity of PSAC inhibitors was measured with human HeLa cells (ATCC# CLL-2) in 96-well plates at 4000 cells/well. Cultures were incubated with each inhibitor at 37° C. for 72 h in Minimal Essential Medium (Gibco/Invitrogen, Carlsbad, Calif.) supplemented with 10% fetal calf serum. Cell viability was quantified using the vital stain MTS [3-(4,5-dimethylthiazol-2-yl)-5-(3-carboxymethony-phenol)-2-(4-sulfophenyl)-2H-tetrazolium, inner salt], as described (Marshall et al., *Growth Regul.*, 5: 69-84 (1995)). The reported $CC_{50}$ value is the concentration of an inhibitor that reduces conversion of MTS formazan by 50%.

Example 7

This example demonstrates that ISPA-28 kills Dd2 cells in vitro when nutrient availability in the media is reduced.

ISPA-28 blocks PSAC on Dd2-infected cells with high affinity and has only weak activity against channels from HB3 parasites ($K_{0.5}$ of 56±5 nM and 43±2 µM, respectively) (Nguitragool et al., *Cell*, 145: 665-677 (2011)). If channel activity serves a role in the growth of the intracellular parasite, this small molecule inhibitor would be expected to interfere with propagation of Dd2 cultures but spare those of HB3. The initial in vitro parasite growth studies revealed an insignificant difference with both parasite lines exhibiting sustained growth in RPMI-based media despite high ISPA-28 concentrations ($IC_{50}$ values >40 µM each, P=0.35 for a difference).

It was determined that ISPA-28 efficacy against Dd2 channels is not compromised by metabolism of the inhibitor under in vitro culture conditions. ISPA-28 is also not significantly adsorbed by serum protein or lipids, a phenomenon known to reduce activity of some. PSAC inhibitors and many therapeutics (Matsuhisa et al., *Chem. Engineering J.*, 34: B21-B27 (1987)). Thus, ISPA-28 does not to inhibit the growth of Dd2 parasites under standard in vitro culture conditions.

One possibility is that channel activity is involved in the survival of malaria parasites, but that the low level transport remaining in the presence of inhibitor adequately meets parasite demands under standard in vitro culture conditions. Consistent with this, sustained channel-mediated uptake in Dd2-infected erythrocytes even with high ISPA-28 concentrations was observed. Significantly less residual uptake was observed with compound (31), a broad spectrum PSAC inhibitor with a comparable inhibitory $K_{0.5}$ value for Dd2 channels (Pillai et al., *Mol. Pharmacol.*, 77: 724-733 (2010)). ($P<10_{-4}$ for comparison of these inhibitors at 10 µM). The unexpected difference in residual channel activity with these inhibitors may account for their differing efficacies against in vitro parasite growth ($IC_{50}$ values of ~50 µM and 4.7 µM, respectively; Table 5).

TABLE 5

| Compound Name | Structure | Transport inhibition $K_{0.5}$, nM | RPMI growth $IC_{50}$, μM | PLM growth $IC_{50}$, μM | $IC_{50}$ ratio |
|---|---|---|---|---|---|
| furosemide | 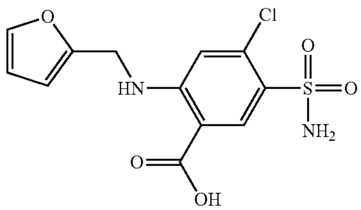 [SMILES: NS(=O)(=O)c1cc(C(=O)O)c(NCc2ccco2)cc1Cl] | 2700 | >200 | 21 | >9.5 |
| dantrolene | 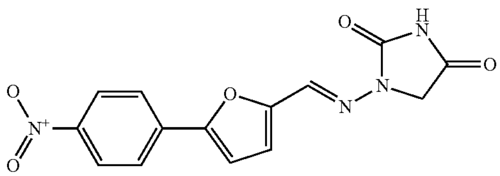 | 1200 | 42 | 3.8 | 18 |
| (24) | 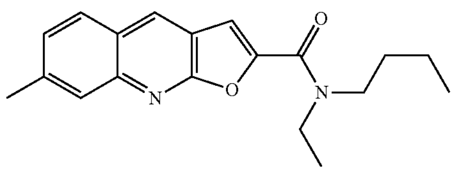 | 87 | 23 | 0.27 | 114 |
| (25) | 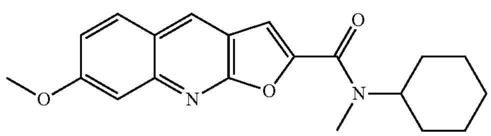 | 33 | 15 | 0.17 | 86 |
| (280) | 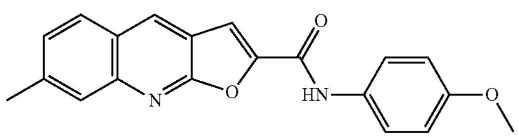 | 6 | 18 | 0.23 | 270 |
| (31) | 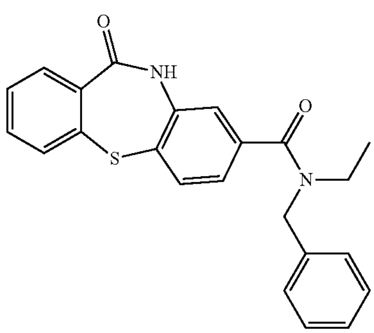 | 84 | 4.7 | 0.41 | 15 |

TABLE 5-continued

| Compound Name | Structure | Transport inhibition $K_{0.5}$, nM | RPMI growth $IC_{50}$, μM | PLM growth $IC_{50}$, μM | $IC_{50}$ ratio |
|---|---|---|---|---|---|
| (3) (TP-52) | 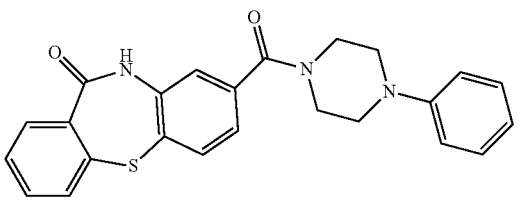 | 25 | 7.3 | 0.19 | 38 |
| Cpd 80 | 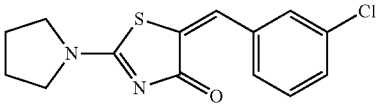 [SMILES: O=C1N=C(N2CCCC2)S/C1=C/c1cccc(Cl)c1] | 44 | 12.5 | 0.17 | 130 |
| Cpd 50 | 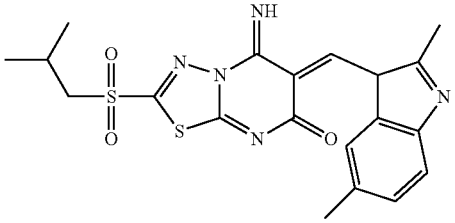 [SMILES: CC1=Nc2ccc(C)cc2C1/C=C1/C(=N)N2N=C(S(=O)(=O)CC(C)C)SC2=NC1=O] | 81 | >30 | 2.0 | >15 |
| ISG-21 | 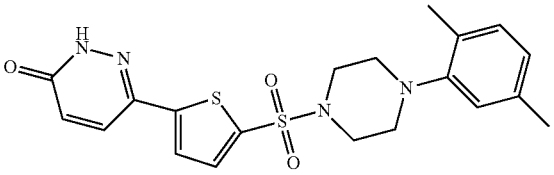 [SMILES: Cc1ccc(C)c(N2CCN(S(=O)(=O)c3ccc(-c4ccc(=O)[nH]n4)s3)CC2)c1] | 2.6 | 1.5 | 0.002 | 800 |
| chloroquine | | inactive | 0.22 | 0.34 | 0.67 |
| mefloquine | | inactive | 0.022 | 0.033 | 0.66 |
| artemisinin | | inactive | 0.018 | 0.026 | 0.66 |

Without being bound to a particular theory or mechanism, it is believed that incomplete block with high ISPA-28 concentrations despite a low $K_{0.5}$ value for Dd2 channels suggests a complex mechanism of inhibition. While dantrolene and furosemide dose responses are adequately fitted by the equation that assumes a stoichiometry for inhibitor and channel molecules, the ISPA-28 dose response was not well fit. An improved fit was obtained with a two-component Langmuir equation. Because this two-component equation is compatible with several possible mechanisms, the ISPA-28 stoichiometry and precise mode of channel block has not yet been determined.

Without being bound by a particular theory or mechanism, it is believed that if PSAC functions in nutrient acquisition for the intracellular parasite (Desai et al., Nature, 406: 1001-1005 (2000)), then the incomplete inhibition by ISPA-28 may permit adequate nutrient uptake. Many nutrients are present at supraphysiological concentrations in the general purpose RPMI 1640 medium (Sato et al., Curr. Protoc. Cell Biol., 1: Unit1.2 (2001)). The large inward concentration gradient for nutrients in this medium could sustain parasite nutrient uptake despite near-complete channel block. Nutrients with PSAC-mediated uptake were surveyed and isoleucine, glutamine, and hypoxanthine were selected because their isolated removal from media adversely affected parasite cultures. Isoleucine and glutamine dose responses revealed that both could be reduced by >90% with negligible effects on propagation of either HB3 or Dd2, consistent with nutrient excess in standard media. Threshold concentrations of these amino acids as well as of hypoxanthine, a purine with high PSAC permeability, were selected (Gem et al., Adv. Exp. Med. Biol., 309A: 169-172 (1991); Asahi et al. Parasitology, 113: 19-23 (1996)). To reduce the inward gradient for nutrient uptake, a PSAC-limiting medium (PLM) was prepared that uses these threshold values while following the RPMI 1640 formulation for all other solutes. Without being bound by a particular theory or mechanism, it is believed that the reduced nutrient content of the PLM medium more closely mimics the nutrient availability under in vivo physiological conditions as compared to RPMI 1640 medium. Both Dd2 and HB3 parasites could be propagated continuously in PLM (>2 weeks), though at somewhat reduced rates. It was observed that cultures with low parasitemias grew well in PLM, but that rates decreased with higher parasite burden, consistent with nutrient limitation and competition between infected cells in culture.

Figure 3A:
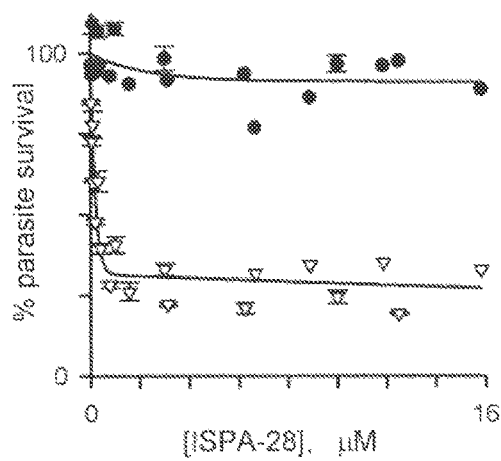
FIG. 3A is a graph showing % survival of Dd2 (open triangles) or HB3 (filled circles) in PLM medium as a function of ISPA-28 concentration ($\mu$M). Solid lines represent the best fits to a two-component exponential decay.

In contrast to the poor ISPA-28 efficacy against parasite growth in the standard RPM 1640 medium, studies using PLM revealed potent killing of Dd2 parasites and continued weak activity against HB3 ($I_{C50}$ values of 0.66±0.20 μM and 52±19 μM, respectively; P<10-4; FIG. 3A). Although there is a nonlinear relationship between nutrient uptake and parasite growth, these $I_{C50}$ values are in reasonable agreement with the transport $_{K0.5}$ values for PSAC block by ISPA-28.

Example 8

This example demonstrates the ISPA-28 growth inhibition phenotype in the progeny of a Dd2×HB3 genetic cross.

Figure 3B:
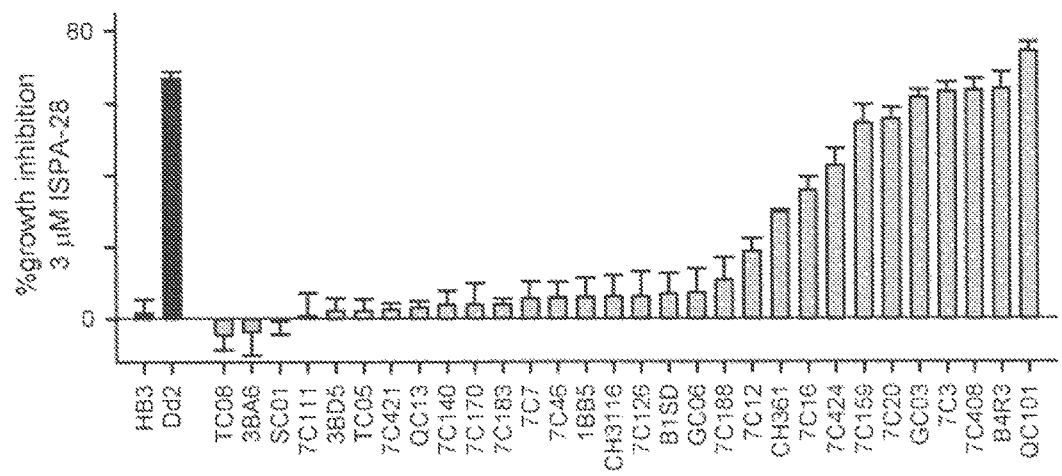
FIG. 3B is a graph showing mean±SEM % parasite growth inhibition by 3 $\mu$M ISPA-28 for indicated parental lines and progeny clones.

Linkage analysis using an independent transport phenotype and this genetic cross have recently implicated two clag3 genes from parasite chromosome 3 in PSAC-mediated solute uptake at the host membrane (Nguitragool et al., Cell, 145: 665-677 (2011)). Here, the growth inhibition studies revealed a broad range of ISPA-28 efficacies for progeny clones, with many progeny resembling one or the other parent. Because HB3 and some progeny had high growth $IC_{50}$ values that could not be precisely estimated, linkage analysis was performed using growth inhibition at 3 μM ISPA-28, a concentration that optimally distinguishes the parental phenotypes (FIG. 3B). This analysis identified a primary association of ISPA-28 growth inhibition with the clag3 locus, providing evidence for a role of this locus in inhibition of both solute transport and parasite killing by ISPA-28. Additional contributing peaks were sought by removing the effects of the clag3 locus; this approach did not identify other statistically significant genomic loci.

The mapped locus is at the proximal end of the parasite chromosome 3 and contains approximately 40 genes. To determine whether clag3 genes are responsible for ISPA-28 mediated killing, growth inhibition studies were performed with HB3$^{3rec}$, a parasite clone generated by allelic exchange transfection of HB3 to replace the 3' end of the native clag3.2 gene with the corresponding fragment from the clag3.1 of Dd2. When this chimeric gene is expressed, HB3$^{3rec}$ exhibits high affinity inhibition by ISPA-28 ($K_{0.5}$ of 51±9 nM, P=0.88 for no difference from Dd2) (Nguitragool et al., Cell, 145: 665-677 (2011)). Here, HB3$^{3rec}$ was used in growth inhibition studies with PLM and it was found that it is sensitive to ISPA-28 at levels matching Dd2. Because HB3$^{3rec}$ is otherwise isogenic with the resistant HB3 line, this finding indicates that ISPA-28 kills parasites primarily via action on the clag3 product and associated channel activity. Furthermore, the requirement for nutrient restriction to detect ISPA-28 mediated killing supports a role of PSAC in parasite nutrient acquisition.

Example 9

This example demonstrates the selection of resistant clag3 alleles though ISPA-28 mediated killing.

Most laboratory parasite lines carry two copies of clag3 genes, both on the Watson strand of the chromosome 3 locus. Epigenetic mechanisms control expression of these genes with individual parasites preferentially expressing one of the two alleles. Upon asexual replication, most daughter parasites continue to express the same allele, but a few undergo switching and express the other allele. In vivo, gene switching is used by malaria parasites and other pathogens to evade host immune responses against crucial surface-exposed antigens.

ISPA-28 was previously used to examine clag3 gene switching (Nguitragool et al., Cell, 145: 665-677 (2011)). This compound is a potent and specific inhibitor of channels associated with expression of the Dd2 clag3.1 gene; it has little or no activity against channels formed by expression of Dd2 clag3.2 or of either clag3 in unrelated parasite lines. The ISPA-28 binding site was delimited to the C-terminus of the clag3.1 product; a short hypervariable domain within this region is exposed at the erythrocyte surface and may define the ISPA-28 binding pocket. ISPA-28 was used to select for cells expressing the Dd2 clag3.1 allele through osmotic lysis in solutions containing ISPA-28 and sorbitol, a sugar alcohol with high PSAC permeability. Sorbitol selects for this allele because osmotic lysis eliminates infected cells whose channels are not blocked by ISPA-28. Of note, these selections were performed on three progeny clones inheriting the Dd2 clag3 locus, but not on Dd2 as this parental line already expresses clag3.1 exclusively. These selections were without effect on HB3 or progeny clones that inherit its clag3 locus because neither of the two HB3 alleles encodes high affinity ISPA-28 inhibition.

Figure 4A:
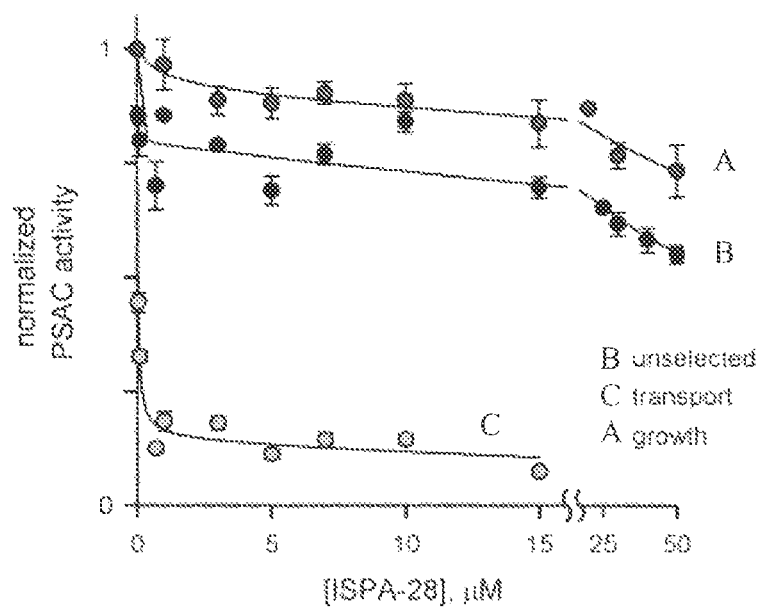
FIG. 4A is a graph showing mean±SEM ISPA-28 dose responses for PSAC inhibition before (B) and after transport selection of the 7C20 line (C) followed by PLM growth selection (A).
Figure 4B:
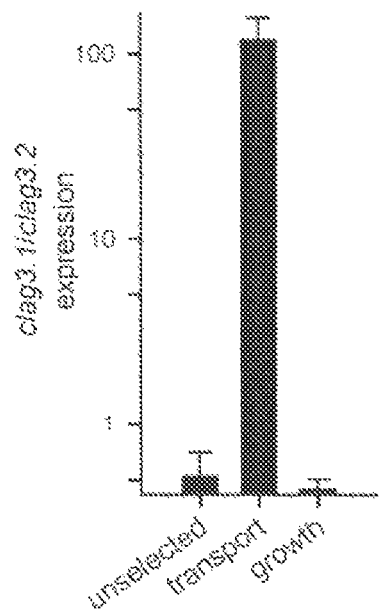
FIG. 4B is a graph showing expression ratio for the two clag3 alleles clag3.1 and clag3.2 before (unselected) and after (transport) selection of the 7C20 line followed by PLM growth selection (growth). Bars represent mean±SEM of replicates from 2-4 separate trials each.

Here, it was hypothesized that in vitro growth inhibition by ISPA-28 may also select for cells expressing individual clag3 genes. Without being bound by a particular theory or mechanism, it is believed that while sorbitol-induced osmotic lysis selects for cells that express the ISPA-28 sensitive clag3.1, growth inhibition in PLM should favor cells expressing the resistant clag3.2 allele because only parasites whose channels are not blocked by ISPA-28 will meet their nutrient demands. The progeny clone 7C20, which carries the clag3 locus and expresses both alleles in unselected cultures (FIGS. 4A-4B), was examined. After selection with osmotic lysis in sorbitol and ISPA-28, surviving parasites had PSAC inhibitor affinity matching the Dd2 parent and predominantly expressed the clag3.1 allele. The culture was then propagated in PLM containing 5 μM ISPA-28 for a total of 10 days; microscopic examination of smears during this treatment revealed near complete sterilization of the culture. Transport studies on parasites surviving this second treatment revealed a marked reduction in ISPA-28 affinity, indicating that in vitro propagation with PSAC inhibitors can be used to select for altered channel phenotypes. RT-PCR confirmed strong negative selection against clag3.1 to yield a parasite population that preferentially expresses clag3.2. There were also modest changes in expression of clag genes on other chromosomes, suggesting that these paralogs may also contribute to PSAC activity. The opposing effects of ISPA-28 on in vitro growth inhibition and on susceptibility to transport-induced osmotic lysis permit purifying selections of either clag3 allele and reveal a strict correlation with channel phenotype.

Surprisingly, the Dd2 parental line retains exclusive expression of clag3.1 in unselected cultures despite being isogenic with 7C20 at the clag3 locus (Nguitragool et al., Cell, 145: 665-677 (2011)). To explore possible mechanisms, it was sought to select Dd2 parasites expressing the alternate clag3.2 allele. Transport selection was tried using osmotic lysis with ISPA-43, a structurally distinct PSAC inhibitor with 10-fold higher affinity for channels formed by expression of the Dd2 clag3.2 than of clag3.1. Although this approach has been successfully used to select for 7C20 parasites expressing clag3.2 (Nguitragool et al., Cell, 145: 665-677 (2011), it was insufficient to affect channel phenotype in Dd2 parasites despite repeated selections over 4 months.

Figure 5A:
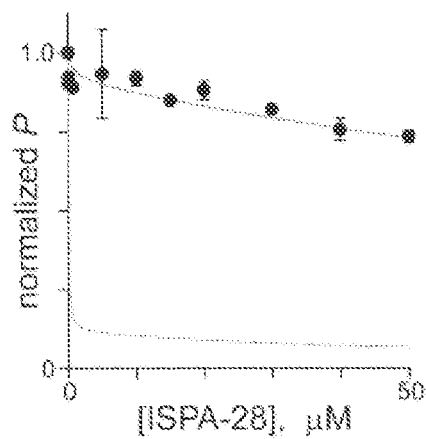
FIG. 5A is a graph showing ISPA-28 dose response for PSAC inhibition in the Dd2-PLM28 line (black circles, mean±SEM of up to 5 measurements each). Solid lines reflect the dose responses for clag3.1 and clag3.2 expression in 7C20 (bottom and top lines, respectively).

Negative selection was attempted with growth inhibition in PLM containing ISPA-28. After 2 cycles of drug pressure with 5 μM ISPA-28 for a total of 17 days, resistant cells were identified and characterized after limiting dilution to obtain the clone Dd2-PLM28. Consistent with killing primarily via PSAC inhibition, transport studies using this resistant clone revealed a marked reduction in inhibitor affinity (FIG. 5A). Although the ISPA-28 dose response quantitatively matched that of 7C20 parasites after identical PLM-based selection (upper solid line, FIG. 5A), full length clag3.2 transcript was still undetectable, excluding the simple prediction of gene switching. Spontaneous recombination between the two clag3 genes was considered, and a chimeric clag3 transcript was identified using a forward clag3.1 primer and a reverse clag3.2 primer; PCR confirmed that this chimera is present in the selected parasite's genome hut absent from the original Dd2 line. Southern blotting with a clag3 specific probe detected throe discrete bands in the selected clone but only the expected two bands in unselected Dd2 parasites, implicating a recombination event to produce three clag3 genes in Dd2-PLM28. The size of the new band, ~16 kb, is consistent with homologous recombination between clag3.1 and clag3.2 in Dd2-PLM28. DNA sequencing indicated that the chimeric gene derives its 5' untranslated region and the first ~70% of the gene from clag3.1. After a crossover between single nucleotide polymorphisms at 3680 and 3965 bp from the start codon, the gene carries the 3' end of clag3.2. Thus, the chimeric gene is driven by the clag3.1 promoter, but encodes a protein with the C-terminal variable domain of clag3.2 This altered C-terminus accounts for the reduced ISPA-28 efficacy against nutrient uptake and, hence, survival of this clone in the selection. Without being bound by a particular theory or mechanism, it is believed that the proposed homologous recombination also produces a parasite having a single clag3 gene and high ISPA-28 affinity, but that recombinant is not expected to survive growth inhibition selection in PLM with ISPA-28.

Figure 5B:
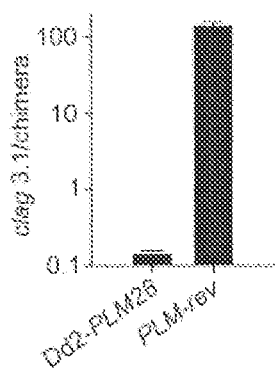
FIG. 5B is a graph showing the ratio quantifying relative expression of clag3 and the chimeric gene in Dd2-PLM28 before and after transport-based selection for clag3.1 using ISPA-28 (PLM28-rev) presented on a log scale.

Quantitative RT-PCR was then used to examine transcription of clag genes in Dd2-PLM28 and found that the chimeric gene is preferentially expressed (8.9±1.3 fold greater than clag3.1, $P<0.002$). Transport-based selection in sorbitol with ISPA-28 was used to examine whether Dd2-PLM28 can undergo expression switching. This second selection yielded parasites that express the native clag3.1 almost exclusively (PLM-rev, FIG. 5B). Transport studies revealed an ISPA-28 dose response identical to that of the original Dd2 line, as expected. Thus, the new chimeric clag3 gene can undergo epigenetic silencing and switching with clag3.1. DNA sequencing of the gene's promoter region did not reveal any mutations relative to that of 7C20.

Without being bound by a particular theory or mechanism, it is believed that recombination between the two clag3 genes occurs with relative ease, consistent with reports of frequent recombination events in the parasite's subtelomeric regions (Freitas-Junior et al., Nature, 407: 1018-22 (2000)). It is also believed that such recombination events may serve to increase diversity in PSAC phenotypes, apparent here as affording survival of a parasite with three clag3 genes under selective pressure.

Example 10

This example demonstrates the comparison of growth inhibitory effects of PSAC inhibitors in PLM and standard media.

Furosemide and dantrolene are known non-specific inhibitors with relatively low PSAC affinity. These compounds are also adsorbed by serum, but are approved therapeutics in other human diseases. They are only weakly effective against parasite growth in standard medium, but have significantly improved activity in PLM. Eight high affinity PSAC inhibitors from 5 distinct scaffolds recently identified by high-throughput screening were also tested (Pillai et al., Mol. Pharmacol., 77: 724-733 (2010)). Each exhibited significantly improved potency when nutrient concentrations are reduced, strengthening the evidence for the channel's role in nutrient acquisition. The extent of improved efficacy was variable, but many compounds exhibited a >100-fold improvement in parasite killing upon nutrient restriction ($IC_{50}$ ratio, Table S). Factors such as the stoichiometry of inhibitor:channel interaction and resultant changes in the concentration dependence of channel block, compound stability in culture, and adsorption by serum may influence this ratio.

To explore therapeutic potential, HeLa cell cytotoxicity was examined in vitro. Several potent PSAC inhibitors were found to be nontoxic and highly specific for parasite killing (Table 6).

TABLE 6

| PSAC Inhibitor | HeLa cell $CC_{50}$, μM | specificity (HeLa $CC_{50}$/ parasite PLM $IC_{50}$) |
|---|---|---|
| (24) | 30 | 110 |
| (280) | >100 | >430 |
| (31) | >100 | >240 |
| (3) | >100 | >530 |
| Cpd 50 | >100 | >50 |
| ISG-21 | 86 | 43,000 |

Finally, in vitro growth inhibition experiments were performed with chloroquine, mefloquine, and artemisinin, approved antimalarial drugs that work at unrelated targets within the intracellular parasite. These drugs do not inhibit PSAC-mediated solute uptake. In contrast to improved killing by PAC inhibitors, these drugs were modestly less effective in PLM than in RPMI (Table 5), excluding non-specific effects of modified in vitro growth conditions. Without being bound by a particular theory or mechanism, it is believed that the robust improvement in parasite killing for PSAC inhibitors upon nutrient restriction is in contrast to the effect on existing antimalarial drugs and, therefore, implicates a novel mechanism of action. Because both isolate-specific and broad spectrum PSAC inhibitors exhibit improved efficacy in PLM, these studies provide experimental evidence for a role of PSAC in nutrient uptake by the intracellular parasite.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value failing within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating malaria in an animal comprising administering an effective amount of a compound of formula (I) to the animal:

$$Q-Y-R^1-R^2 \qquad (I),$$

wherein:

Q is a heterocyclic group fused to a heterocyclic amido group, which is optionally substituted with one or more substituents selected from the group consisting of halo, hydroxy, mercapto, alkoxy, alkylthio, nitro, cyano, amino, alkyl, aryl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

Y is S;

$R^1$ is benzo fused heterocyclyl, which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

R² is heterocyclyl carbonylamino, which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

or a pharmaceutically acceptable salt thereof.

2. A method of inhibiting a plasmodial surface anion channel of a parasite in an animal comprising administering an effective amount of a compound of formula (I) to the animal:

Q-Y—R¹—R²           (I), wherein:

Q is a heterocyclic group fused to a heterocyclic amido group, which is optionally substituted with one or more substituents selected from the group consisting of halo, hydroxy, mercapto, alkoxy, alkylthio, nitro, cyano, amino, alkyl, aryl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

Y is S;

R¹ is benzo fused heterocyclyl, which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

R² is heterocyclyl carbonylamino, which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxy, carboxyalkyl, alkylcarbonyl, alkoxycarbonyl, aminocarbonyl, ureido, and formyl;

or a pharmaceutically acceptable salt thereof.

3. The method according to claim 1, wherein R¹ is benzothiazolyl, which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxyalkyl, alkylcarbonyl, alkoxycarbonyl, aminocarbonyl, ureido, and formyl.

4. The method according to claim 1, wherein R² is thiophenylcarbonylamino, which is optionally substituted with one or more substituents selected from the group consisting of halo, hydroxy, mercapto, alkoxy, alkylthio, nitro, cyano, amino, alkyl, hydroxyalkyl, haloalkyl, cyanoalkyl, aminoalkyl, alkylamino, dialkylamino, carboxyalkyl, alkylcarbonyl, alkoxycarbonyl, aminocarbonyl, ureido, and formyl.

5. The method according to claim 1, wherein the compound is:

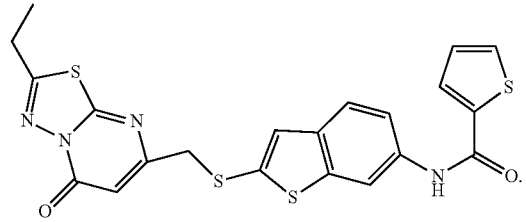

ISG-28

6. The method according to claim 1, wherein Y is S.
7. The method according to claim 6, wherein Q is

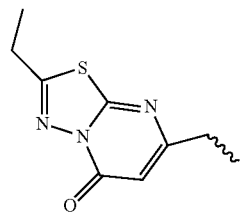

8. The method according to claim 6, wherein R¹ is

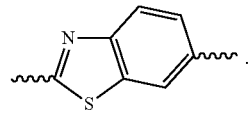

9. The method according to claim 6, wherein R² is

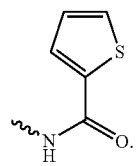

10. The method according to claim 1, further comprising administering at least one other antimalarial compound to the animal.

11. The method according to claim 10, wherein the at least one other antimalarial compound is selected from the group consisting of:

a) a compound of formula II:

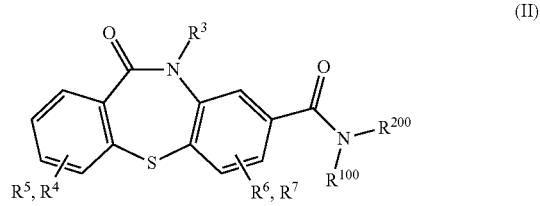

(II)

wherein R¹⁰⁰ is hydrogen or alkyl and R²⁰⁰ is arylalkyl, optionally substituted on the aryl with one or more substituents selected from the group consisting of halo, hydroxyl, nitro, cyano, amino, alkyl, aminoalkyl, alkylamino, alkylcarbonyl, alkoxycarbonyl, aminocarbonyl, and formyl; or $R^{200}$ is a group of formula (III):

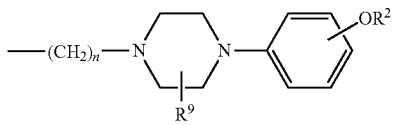

(III)

wherein n=0 to 6;
or $R^{100}$ and $R^{200}$ together with the N to which they are attached form a heterocycle of formula IV:

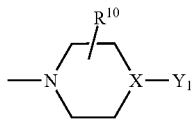

(IV)

wherein X is N or CH; and
$Y_1$ is aryl, alkylaryl, dialkylaryl, arylalkyl, alkoxyaryl, or heterocyclic, optionally substituted with one or more substituents selected from the group consisting of halo, hydroxyl, nitro, cyano, amino, aminoalkyl, alkylamino, alkylcarbonyl, alkoxycarbonyl, aminocarbonyl, and formyl; and
$R^3$-$R^{10}$ are hydrogen or alkyl; or a pharmaceutically acceptable salt thereof;
(b) a compound of formula V:

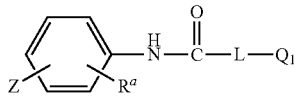

(V)

wherein
Z is a group having one or more 4-7 membered rings, wherein at least one of the rings has at least one heteroatom selected from the group consisting of O, S, and N; and when two or more 4-7 membered rings are present, the rings may be fused or unfused; wherein the rings are optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl;
$R^a$ is hydrogen, alkyl, or alkoxy;
L is a bond, alkyl, alkoxy, $(CH_2)_r$, or $(CH_2O)_s$, wherein r and s are independently 1 to 6;
$Q_1$ is a heterocyclic group, an aryl group, or an heterocyclyl aryl group, each of which is optionally substituted with one or more substituents selected from the group consisting of halo, hydroxy, alkoxy, nitro, cyano, amino, alkyl, aminoalkyl, alkylamino, alkylcarbonyl, alkoxycarbonyl, aminocarbonyl, and formyl; and
when L is alkyl or alkoxy, $Q_1$ is absent;
or a pharmaceutically acceptable salt thereof; and
(c) a compound of formula VI:

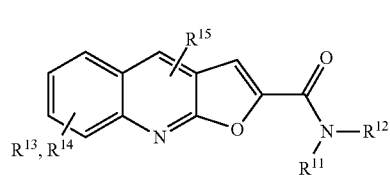

(VI)

wherein $R^{11}$ and $R^{12}$ are independently hydrogen, alkyl, cycloalkyl, or aryl which is optionally substituted with one or more substituents selected from the group consisting of alkyl, alkoxy, halo, hydroxy, nitro, cyano, amino, alkylamino, aminoalkyl, alkylcarbonyl, alkoxycarbonyl, aminocarbonyl, and formyl;
$R^{13}$-$R^{15}$ are independently selected from the group consisting of alkyl, halo, alkoxy, hydroxy, nitro, cyano, amino, alkylamino, aminoalkyl, alkylcarbonyl, alkoxycarbonyl, aminocarbonyl, and formyl;
or a pharmaceutically acceptable salt thereof.

12. The method according to claim 1, wherein the animal is a human.

13. The method according to claim 1, wherein the compound inhibits growth of *P. falciparum* Dd2.

* * * * *